US008110201B2

(12) United States Patent
Skeiky et al.

(10) Patent No.: US 8,110,201 B2
(45) Date of Patent: Feb. 7, 2012

(54) FUSION PROTEINS OF MYCOBACTERIUM TUBERCULOSIS

(75) Inventors: Yasir Skeiky, Bellevue, WA (US); Jeff Guderian, Lynwood, WA (US); Steven Reed, Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 12/698,976

(22) Filed: Feb. 2, 2010

(65) Prior Publication Data

US 2010/0183677 A1 Jul. 22, 2010

Related U.S. Application Data

(60) Continuation of application No. 11/982,179, filed on Oct. 31, 2007, now Pat. No. 7,691,993, which is a continuation of application No. 11/342,364, filed on Jan. 26, 2006, now Pat. No. 7,678,375, which is a division of application No. 10/369,983, filed on Feb. 18, 2003, now Pat. No. 7,026,465.

(60) Provisional application No. 60/357,351, filed on Feb. 15, 2002.

(51) Int. Cl.
*A61K 39/04* (2006.01)
*A61K 39/02* (2006.01)
*A61K 39/00* (2006.01)

(52) U.S. Cl. ............... 424/248.1; 424/184.1; 424/185.1; 424/190.1; 424/192.1; 424/234.1; 530/300; 530/350; 536/23.1; 536/23.7

(58) Field of Classification Search .............. 424/184.1, 424/185.1, 190.1, 192.1, 234.1, 248.1; 530/300, 530/350; 536/23.1, 23.7
See application file for complete search history.

(56) References Cited

U.S. PATENT DOCUMENTS

| | | | |
|---|---|---|---|
| 3,943,119 | A | 3/1976 | Tsumita et al. |
| 4,235,877 | A | 11/1980 | Fullerton |
| 4,436,727 | A | 3/1984 | Ribi |
| 4,603,112 | A | 7/1986 | Paoletti et al. |
| 4,689,397 | A | 8/1987 | Shinnick et al. |
| 4,751,180 | A | 6/1988 | Cousens et al. |
| 4,769,330 | A | 9/1988 | Paoletti et al. |
| 4,777,127 | A | 10/1988 | Suni et al. |
| 4,866,034 | A | 9/1989 | Ribi |
| 4,876,089 | A | 10/1989 | Luciw et al. |
| 4,877,611 | A | 10/1989 | Cantrell |
| 4,879,213 | A | 11/1989 | Fox et al. |
| 4,897,268 | A | 1/1990 | Tice et al. |
| 4,912,094 | A | 3/1990 | Myers et al. |
| 4,935,233 | A | 6/1990 | Bell et al. |
| 4,946,778 | A | 8/1990 | Ladner et al. |
| 4,952,395 | A | 8/1990 | Shinnick et al. |
| 5,108,745 | A | 4/1992 | Horwitz |
| 5,145,684 | A | 9/1992 | Liversidge et al. |
| 5,240,856 | A | 8/1993 | Goffe et al. |
| 5,330,754 | A | 7/1994 | Kapoor et al. |
| 5,466,468 | A | 11/1995 | Schneider et al. |
| 5,478,726 | A | 12/1995 | Shinnick et al. |
| 5,504,005 | A | 4/1996 | Bloom et al. |
| 5,543,158 | A | 8/1996 | Gref et al. |
| 5,565,213 | A | 10/1996 | Nakamori et al. |
| 5,567,434 | A | 10/1996 | Szoka |
| 5,580,579 | A | 12/1996 | Ruddy et al. |
| 5,583,112 | A | 12/1996 | Kensil et al. |
| 5,599,545 | A | 2/1997 | Stanford et al. |
| 5,616,500 | A | 4/1997 | Steinert et al. |
| 5,639,653 | A | 6/1997 | Bloom et al. |
| 5,714,593 | A | 2/1998 | Laqueyrerie et al. |
| 5,780,045 | A | 7/1998 | McQuinn |
| 5,783,386 | A | 7/1998 | Jacobs, Jr. et al. |
| 5,795,587 | A | 8/1998 | Gao et al. |
| 5,804,212 | A | 9/1998 | Illum |
| 5,811,128 | A | 9/1998 | Tice et al. |
| 5,814,344 | A | 9/1998 | Tice et al. |
| 5,817,473 | A | 10/1998 | Das et al. |
| 5,820,883 | A | 10/1998 | Tice et al. |
| 5,853,763 | A | 12/1998 | Tice et al. |
| 5,856,462 | A | 1/1999 | Agrawal |
| 5,928,647 | A | 7/1999 | Rock |
| 5,942,252 | A | 8/1999 | Tice et al. |
| 5,955,077 | A | 9/1999 | Andersen et al. |
| 5,985,287 | A | 11/1999 | Tan et al. |
| 6,001,361 | A | 12/1999 | Tan et al. |
| 6,034,218 | A | 3/2000 | Reed et al. |
| 6,037,135 | A | 3/2000 | Kubo et al. |
| 6,113,918 | A | 9/2000 | Johnson et al. |
| 6,290,969 | B1 | 9/2001 | Reed et al. |
| 6,338,852 | B1 | 1/2002 | Reed et al. |
| 6,350,456 | B1 | 2/2002 | Reed et al. |

(Continued)

FOREIGN PATENT DOCUMENTS

EP 345242 12/1989

(Continued)

OTHER PUBLICATIONS

Girard, M.P., et al., Vaccine, vol. 23, pp. 5725-5731, 2005.*
Orme, I.M., Vaccine, vol. 24, pp. 2-19, 2006.*
Altschul, et al., "Gapped Blast and PSI-Blast: a new generation of protein database search programs,"Nuc. Acids Res. (25):3389-3402 (1977).
Barnes, et al., "Immunoreactivity of a 10-kDa Antigen of *Mycobacterium tuberculosis*," J. of Immunology 148(6):1835-1840 (1992).
Barrera, et al., Humoral Response to *Mycobacterium tuberculosis* in Patients with Human Immunodeficienty Virus Infection Tuberde and Lung Disease 73(4):187-91 (1992).

(Continued)

*Primary Examiner* — Rodney P. Swartz
(74) *Attorney, Agent, or Firm* — Convergent Law Group LLP

(57) ABSTRACT

The present invention relates to compositions and fusion proteins containing at least two *Mycobacterium* sp. antigens, and nucleic acids encoding such compositions and fusion proteins. The compositions of the invention increase serological sensitivity of sera from individuals infected with tuberculosis, and methods for their use in the diagnosis, treatment, and prevention of tuberculosis infection.

11 Claims, 43 Drawing Sheets

U.S. PATENT DOCUMENTS

| | | | |
|---|---|---|---|
| 6,355,257 | B1 | 3/2002 | Johnson et al. |
| 6,458,366 | B1 | 10/2002 | Reed et al. |
| 6,465,633 | B1 | 10/2002 | Skeiky |
| 6,544,522 | B1 | 4/2003 | Skeiky et al. |
| 6,555,653 | B2 | 4/2003 | Alderson et al. |
| 6,592,877 | B1 | 7/2003 | Reed et al. |
| 6,613,881 | B1 | 9/2003 | Alderson et al. |
| 6,627,198 | B2 | 9/2003 | Reed et al. |
| 6,949,246 | B2 | 9/2005 | Reed et al. |
| 6,962,710 | B2 | 11/2005 | Reed et al. |
| 6,977,069 | B2 | 12/2005 | Reed et al. |
| 7,026,465 | B2 | 4/2006 | Skeiky et al. |
| 7,064,195 | B2 | 6/2006 | Skeiky et al. |
| 7,083,796 | B2 | 8/2006 | Skeiky et al. |
| 7,087,713 | B2 | 8/2006 | Campos-Neto et al. |
| 7,122,196 | B2 | 10/2006 | Reed et al. |
| 7,186,412 | B1 | 3/2007 | Skeiky et al. |
| 7,261,897 | B2 | 8/2007 | Skeiky et al. |
| 7,311,922 | B1 | 12/2007 | Skeiky et al. |
| 7,335,369 | B2 | 2/2008 | Reed et al. |
| 7,678,375 | B2 | 3/2010 | Skeiky et al. |
| 7,691,993 | B2 | 4/2010 | Skeiky et al. |
| 2006/0193876 | A1 | 8/2006 | Skeiky et al. |
| 2007/0054336 | A1 | 3/2007 | Campos-Neto et al. |
| 2007/0141087 | A1 | 6/2007 | Reed et al. |
| 2008/0176798 | A1 | 7/2008 | Campos-Neto et al. |
| 2008/0199405 | A1 | 8/2008 | Reed et al. |
| 2008/0269151 | A1 | 10/2008 | Skeiky et al. |
| 2008/0317716 | A1 | 12/2008 | Skeiky et al. |
| 2009/0017077 | A1 | 1/2009 | Reed et al. |
| 2009/0018095 | A1 | 1/2009 | Skeiky et al. |
| 2009/0022742 | A1 | 1/2009 | Campos-Neto et al. |
| 2009/0281168 | A1 | 11/2009 | Reed et al. |
| 2009/0306195 | A1 | 12/2009 | Skeiky et al. |
| 2010/0015096 | A1 | 1/2010 | Skeiky et al. |
| 2010/0183657 | A1 | 7/2010 | Skeiky et al. |

FOREIGN PATENT DOCUMENTS

| | | |
|---|---|---|
| EP | 419355 | 3/1991 |
| EP | 519218 | 12/1992 |
| FR | 2244539 | 4/1975 |
| FR | 2265402 | 10/1975 |
| GB | 2200651 | 8/1988 |
| GB | 2298862 | 9/1996 |
| HU | 158035 | 3/1971 |
| RU | 2024021 | 11/1994 |
| WO | WO 88/05823 | 8/1988 |
| WO | WO 88/06591 | 9/1988 |
| WO | WO 89/01973 | 3/1989 |
| WO | WO 89/06280 | 7/1989 |
| WO | WO 91/02805 | 3/1991 |
| WO | WO 91/04272 | 4/1991 |
| WO | WO 91/14448 | 10/1991 |
| WO | WO 91/18926 | 12/1991 |
| WO | WO 92/04049 | 3/1992 |
| WO | WO 92/07243 | 4/1992 |
| WO | WO 92/14154 | 8/1992 |
| WO | WO 92/14823 | 9/1992 |
| WO | WO 92/16628 | 10/1992 |
| WO | WO 92/21697 | 12/1992 |
| WO | WO 92/21758 | 12/1992 |
| WO | WO 94/00153 | 1/1994 |
| WO | WO 94/00228 | 1/1994 |
| WO | WO 94/00492 | 1/1994 |
| WO | WO 94/00493 | 1/1994 |
| WO | WO 94/14069 | 6/1994 |
| WO | WO 94/20078 | 9/1994 |
| WO | WO 94/23701 | 10/1994 |
| WO | WO 95/01440 | 1/1995 |
| WO | WO 95/01441 | 1/1995 |
| WO | WO 95/14713 | 6/1995 |
| WO | WO 95/17210 | 6/1995 |
| WO | WO 95/17511 | 6/1995 |
| WO | WO 95/31216 | 11/1995 |
| WO | WO 96/02555 | 2/1996 |
| WO | WO 96/06638 | 3/1996 |
| WO | WO 96/15241 | 5/1996 |
| WO | WO 96/23885 | 8/1996 |
| WO | WO 96/28551 | 9/1996 |
| WO | WO 96/33739 | 10/1996 |
| WO | WO 96/38591 | 12/1996 |
| WO | WO 97/09428 | 3/1997 |
| WO | WO 97/09428 A2 | 3/1997 |
| WO | WO 97/09429 | 3/1997 |
| WO | WO 97/09429 A2 | 3/1997 |
| WO | WO 97/24447 | 10/1997 |
| WO | WO 98/07868 | 2/1998 |
| WO | WO 98/16645 A2 | 4/1998 |
| WO | WO 98/16646 A2 | 4/1998 |
| WO | WO 98/44119 | 10/1998 |
| WO | WO 98/53075 A2 | 11/1998 |
| WO | WO 98/53076 | 11/1998 |
| WO | WO 99/09186 | 2/1999 |
| WO | WO99/33488 | 7/1999 |
| WO | WO 99/42076 A2 | 8/1999 |
| WO | WO 99/42118 A2 | 8/1999 |
| WO | WO/99/51748 | 10/1999 |
| WO | WO 99/51748 A2 | 10/1999 |
| WO | WO 99/51748 A3 | 10/1999 |
| WO | WO 99/52549 | 10/1999 |
| WO | WO 00/09159 | 2/2000 |
| WO | WO 01/24820 | 4/2001 |
| WO | WO 01/34802 | 5/2001 |
| WO | WO 01/34803 | 5/2001 |
| WO | WO 01/51633 | 7/2001 |
| WO | WO 01/62893 A2 | 8/2001 |
| WO | WO 01/73032 | 10/2001 |
| WO | WO 01/90152 | 11/2001 |
| WO | WO 01/98460 | 12/2001 |
| WO | WO 2005/076101 | 8/2005 |
| WO | WO 2008/107370 | 9/2008 |

OTHER PUBLICATIONS

Batzer, et al., "Enhances evolutionary PCR using oligonucleotides with inosine at the 3' terminus" Nuc. Acids Res. 19:5081 (1991).

Berkner, "Development of Adenovirus Vectors for the Expression of Heterologous Genes," Biotechniques 6:616-627 (1988).

Boesen et al., "Human T-Cell Responses to Secreted Antigen Fractions of *Mycobacterium tuberculosis*," Infection and Immunity 63(4):1491-1497 (1995).

Borremans et al., "Cloning, Sequencing Determination, and Expression of a 32-Kilodalton-Protein Gene of *Mycobacterium tuberculosis*," Infection and Immunity 57(10):3123-3130 (1989).

Bowie, et al., "Deciphering the Message of Protein Sequences: Tolerance to Amino Acid Substitutions" Science 257:1306-10 (1990).

Brandt, et al. "ESAT-6 subunit vaccination against *Mycobacterium tuberculosis*," Infection and Immunity 68(2):791-795 (2000).

Brandt, et al. "The Protective Effect of the Mycobacterium bovis BCG Vaccine is Increased by Coadministration with the *Mycobacterium tuberculosis* 72-Kilodalton Fusion Polyprotein Mtb72F in *M. tuberculosis*-Infected Guinea Pigs" Infection and Immunity 72(11):6622-32 (2004).

Burgess, et al. "Possible Dissociation of the Heparin-binding and Mitogenic Activities of Heparin-Binding (Acidic Fibroblast) Growth Factor-1 from its Receptor-binding Activities by Site-Directed Mutagenesis of a Single Lysine Residue" J. Cell. Biol. 111:2129-2138 (1990).

Cameron, et al., "Identification and characterization of a putative serine protease expressed in vivo by *Mycobacterium avium* subsp. *Paratuberculosisi*," Microbiology 140( 8):1977-1982 (1994).

Campos-Neto, et al., "Cutting Edge: CD40 Ligand Is Not Essential for the Development of Cell-Mediated Immunity and Resistance to *Mycobacterium tuberculosis*," J. Immunol.160(5): 2037-2041 (1988).

Carter and Wells, "Dissecting the catalytic triad of a serine protease," Nature 332: 564-568 (1988).

Carter, "Peptide Analysis Protocols," Methods in Molecular Biology, Chapter 1.1, 36:193-206 (1994).

Chaitra, et al., "Defining putative T cell epitopes from PE and PPE families of protein of *M. tuberculosis* with vaccine potential" Vaccine 23(10):1265-72 (2005).

Chaitra, et al., "HLAA0201-restricted cytotoxic T-cell epitopes in three PE/PPE family proteins of *M. tuberculosis*" Scand. J. of Immunology 67(4):411-17 (2008).
Chan and Kaufmann, Tuberculosis: Pathogenesis, Protection and Control, Chap. 24, ASM Press (1994).
Chen, et al., "T Cells for Tumor Therapy can be Obtained from Antigen-loaded Sponge Implants" Cancer Res. 54: 1065-1070 (1994).
Cirillo, et al., "Isolation and characterization of the aspartokinase and aspartate semialdehyde dehydrogenase operon from mycobacteria," Molecular Microbiology 11(4): 629-639 (1994).
Cohen, "Naked DNA Points Way to Vaccines" Science 259: 1691-1692 (1993).
Colbere-Garapin, et al., "A New Dominant Hybrid Selective Marker for Higher Eucaryotic Cells," J. Mol. Biol. 150:1-14 (1981).
Coler, et al. "Molecular cloning and immunologic reactivity of a novel low molecular mass antigen for *Mycobacterium tuberculosis*," J. Immunol. 161(5):2356-2364 (1998).
Collins, "New Generation of tuberculosis vaccines," Clinical Microbioloogy Newsletter 23 (3):17-23 (2001).
Coombes, et al., "Single dose, polymeric, microparticle-based vaccines: the influence of formulation conditions on the magnitude and duration of the immune response to a protein antigen," Vaccine 14: 1429-1438 (1996).
Coruzzi, et al., "Tissue-specific and light-regulated expression of a pea nuclear gene encoding the small subunit of ribulose-1,5-biphosphate carboxylase," EMBO 3: 1671-1680 (1984).
Creighton, Protein Structure: A Practical Approach, pp. 184-186 (1989).
Creighton, Proteins: Structures and Molecular Properties, pp. 314-315 (1984).
Daleine, et al., "Preliminary evaluation of a *Mycobacterium tuberculosis* lpoligosaccharide (Los) antigen in the serological diagnosis of tuberculosis in HIV seropositive and seronegative patients," Tuberde and Lung Disease, 76( 3): 234-39 (1995).
Devereaux, et al., "A Comprehensive System of Sequence Analysis Tools for the VAX," Nuc. Acids Res. 12: 387-395 (1984).
Dillon, et al., "Molecular Characterization and Human T-Cell Responses to a Member of Novel *Mycobacterium tuberculosis* mtb39 Gene Family," Infection and Immunity 67( 6): 2941-2950 (1999).
Doran, et al., "Characertisation of a Novel Repetitive DNA sequence from *Mycrobacerium bovis*," FEMS Microbiology Letters 96: 179-186 (1992).
Eiglmeier, et al., "Use of an ordered cosmid library to deduce the genomic organization of *Mycobacterium leprae*," Mol. Microbiol. 7(2):197-206 (1993).
Fifis, et al., "Purification and Characterization of Major Antigens from a *Mycobacterium bovis* Culture Filtrate," Infection and Immunity 59(3):800-807 (1991).
Fisher-Hoch, et al., "Protection of rhesus monkey from fatal Lassa fever by vaccination with a recombinant vaccinia virus containing the Lassa virus glycoprotein gene" PNAS USA 86: 317- 321 (1989).
Flexner, et al., "Vaccinia Virus Expression Vectors" Vaccine 8:17-21 (1989).
Flexner, "Attenuation and immugenicity in primates of vaccinia virus recombinants expression human interleukin-2," Ann. NY. Acad. Sci. 569: 86-103 (1989).
Flynn, et al., "An essential Role for Interferon γ in Resistance to *Mycobacterium tuberculosis* Infection," J. of Experimental Medicine 178: 2249-2254 (1993).
Fsihi, et al. "The *Mycrobacterium leprae* genome: systematic sequence ananlysis indentifies key catabolic enzymes, ATP-dependaent transport system and a novel PolA locus associated with genomic variability," Molecular Microbiology 16(5):909-919 (1995).
Garcia, "Nucleotide Sequence and Expression of *pneumococcal* autolysin gene from its own promoter in *E. Coli*," Gene (43):265-292 (1986).
Geysen, et al. "Cognitive features of continuous antigenic determinants," J. Mol. Recognition 1:32-41 (1988).
Seq_Compugen_P95243, 1997.
Seq_Compugen_P96361, 1997.
Seq_Compugen_P95012, 1997.
Seq_Compugen_Q49722, 1996.
Seq_EMBL_X84741-Mycrobacteriumbovis BCG IS1081 DNA Sequence, Van Soolingen, D.
Seq_NCBI_CAA17362.
U.S Appl. No. 09/724,685, filed Oct. 11, 1996.
First Office Action for U.S. Appl. No. 08/658,800.
Second Office Action for U.S. Appl. No. 08/658,800.
First Office Action for U.S. Appl. No. 08/659,683.
Second Office Action for U.S. Appl. No. 08/659,683.
First Office Action for U.S. Appl. No. 08/680,573.
Second Office Action for U.S. Appl. No. 08/680,573.
First Office Action for U.S. Appl. No. 08/680,574.
Second Office Action for U.S. Appl. No. 08/680,574.
First Office Action for U.S. Appl. No. 08/729,622.
Second Office Action for U.S. Appl. No. 08/729,622.
First Office Action for U.S. Appl. No. 08/730,510.
First Office Action for U.S. Appl. No. 08/818,111.
Second Office Action for U.S. Appl. No. 08/818,111.
First Office Action for U.S. Appl. No. 08/942,578.
First Office Action for U.S. Appl. No. 09/056,556.
Second Office Action for U.S. Appl. No. 09/056,556.
First Office Action for U.S. Appl. No. 09/072,967.
First Office Action for U.S. Appl. No. 09/073,009.
Second Office Action for U.S. Appl. No. 09/073,009.
Third Office Action for U.S. Appl. No. 07/073,009.
Fourth Office Action for U.S. Appl. No. 09/073,009.
First Office Action for U.S. Appl. No. 09/073,010.
Second Office Action for U.S. Appl. No. 09/073,010.
Third Office Action for U.S. Appl. No. 09/073,010.
Office Action for U.S. Appl. No. 08/730,510.
Office Action for U.S. Appl. No. 09/470,191.
First Office Action for U.S. Appl. No. 09/072,596.
Goodman-Smitkoff, et al., "Defining minimal requirements for antibody production to peptide antigens," Vaccine 8: 257-262 (1990).
Grant, et al., "Expression and Secretion Vectors for Yeast," Methods Enzymol. 153: 516-544 (1987).
Greenspan and Di Cera, "Defining epitopes: Its not as easy as it seems," Nature Biotechnology 17: 936-937 (1999).
Greenway, et al., "Enhancement of protective immune responses to Venezuelan equine encephalitis (VEE) virus with microencapsulated vaccine," Vaccine 13:1411-1420 (1995).
Griffin, et al., "Animal Models of Protective Immunity in Tuberculosis to Evaluate Candidate Vaccines;" Trends in Microbiology 3(11): 418-423 (1995).
Guzman, et al., "Efficient Gene Transfer into Myocardium by Direct Injection of Adenovirus," Cir. Res. 73: 1202-1207 (1993).
Harrison's Principles of Internal Medicine, vol. 1, pp. 1004-1014 (1998).
Harrison's Principles of Internal Medicine, vol. 1, pp. 1019-1023 (1998).
Hartman and Mulligan, "Two dominant-acting selectable markers for gene transfer studies in mammalian cells," PNAS USA 85: 8047-51 (1988).
Hendrickson, et al., "Mass Spectrometric Identification of Mtb81, A Novel Serological Marker for Tuberculosis," J. Clin. Microbiol 38(6):2354-2361 (2000).
Higgins and Sharp, "Fast and sensitive multiple sequence alignments on a microcomputer," Cabios 5:151-153 (1989).
Hobbs, McGraw Hill Yearbook of Science and Technology, pp. 191-196 (1992).
Horn, et al., "Synthesis of oligonucleotides on cellulose," Nucl. Acids Res. Symposia Series, pp. 225-232 (1980).
Horwitz et al., "Protective immunity against tuberculosis induced by vaccination with major extracellular protein of Mycobacterium tuberculosis," PNAS USA 92:1530-1534 (1995).
Jacobs, "Advances in mycobacterial genetics: new promises for old diseases," Immunobiology 184(2-3):147-156 (1992).
Jurcevic, et al., "T cell responses to a mixture of Mycobacterium tuberculosis peptide with complementary HLA-DR binding profiles," Clinical and Experimental Immunology 105(3): 416-421 (1996).
Kadival, et al. "Radioimmunoassay of tuberculous antigen," Indian J. Med. Res. 75:765-770 (1982).

Kalinowski, et al., "Genetic and biochemical analysis of the aspartokinase from *Corynebacterium glutamicum*," Molecular Microbiology 5:1197-1204 (1991).
Kass-Eisler, et al., "Quantitative determination of Adenoviral-mediated gene delivery to rat cardiac myocytes in vitro and in vivo," PNAS USA 90:11498-11502 (1993).
Karlin and Altschul, "Applications and statistics for multiple high-scoring segments in molecular sequences," PNAS USA 90: 5873-5787 (1993).
Kaufmann, et al., "Vaccination against tuberculosis and leprosy," Immunobiology 184(2-3): 208-229 (1992).
Khanolkar-Young, et al., "Results of the Third Immunology of Tuberculosis Anitmycobacterial Monoclonal Antibody Workshop" Infection and Immunity 60(9):3925-927 (1992).
Kohler and Milstein, "Continuous cultures of fused cells secreting antibodies of predefined sequence," Nature 256:495-497 (1975).
Kolls, "Prolonged and effective blockade of TNF activity through Adenoviral-mediated gene transfer," PNAS USA 91: 215-219 (1994).
Kozak, "Comparison of Initiation of Protein Synthesis in Procaryotes, Eucaryotes, and Organelles;" Microbiological Review, pp. 1-45 (1983).
Kroll, et al., "A Multifunctional Prokaryotic Protein Expression System: Overproduction, Affinity Purification, and Selective Detection," DNA Cell Biol. 12:441-453 (1993).
Labouesse, et al., "Conformational changes in enzyme catalysis," Biochemistry 48:2137-2145 (1962).
Launois, et al., "T-Cell Epitope Mapping of the Major Secreted Mycobacterial Antigen AG85A in Tuberculosis and Leprosy," Infection and Immunity 62:3679-87 (1994).
Lazar, et al., "Transforming Growth Factor-alpha Mutation of Aspartic Acid 47 and Leucine 48 results in Different Biological Activities" Mol. Cell. Biol. 8(3):1247-1252 (1988).
Leao, et al., "Immunological and functional characterization of proteins of the Mycobacterium tuberculosis antigen 85 complex using synthetic peptides," J. Gen. Microbiol. 139:1543-1549 (1993).
Lee, et al. "Characterization of the Major Membrane Protein of Virulent Mycobacterium tuberculosis," Infection and Immunity 60:2066-2074 (1992).
Lerner, et al., "Cloning and structure of the *Bacillus subtilis* aspartate transcarbamylas gene (pyrB)," J. Biol. Chem. 261(24):11156-11165 (1986).
Lewin, Genes IV, Oxford University Press, pp. 124-126 (1990).
Lewinsohn, et al., "Characterization of HumanCD8+ T Cells Reactive with Mycrobacterium tuberculosis-infected Antigen-presenting Cells," J. Exp. Med. 187(10):1633-1640 (1998).
Li, et al., "Important Role of the Amino Acid Attached to tRNA in Formylation and in Initiation of Protein Synthesis in *Escherichia coli*," J. Biol. Chem., 271:1022-1028 (1996).
Ljungqvist, et al., "Antibody Responses Against Mycobacterium Tuberculosis in 11 Strains of Inbred Mice Novel Monoclonal Antibody Specificities Generated by Fusions Using Spleens from BALB B10 and CBA-J Mice," Infections and Immunity 56(8):1994-98 (1988).
Logan and Shenk, "Advenovirus tripartite leader sequence enhances translation of mRNAs late after infection," PNAS USA 81: 365-3659 (1984).
Lowrie, et al., "Towards a DNA vaccine against tuberculosis," Vaccine 12(16):1537-1540 (1994).
Lowy, et al., "Isolation of transforming DNA: Cloning the Hamster aprt Gene," Cell 22:817-23 (1990).
Maddox, et al., "Elevated Serum Levels in Human Pregnancy of a Molecule Immunochemically similar to Eosinophil Granule Major Basic Protein," J. Exp. Med. 158:1211-1216 (1983).
Mahairas, et al., "Molecular Analysis of Genetic Differences Between *Mycrobacterium bovis* BCG and Virulent M. bovis," J. of Bacteriology 178(5): 1274-1282 (1996).
Mahvi, et al., "DNA Cancer Vaccines—A Gene Gun Approach," Imm. and Cell Bio. 75: 456-460 (1997).
Manca, et al., "Molecular cloning, purification, and serological characterization of MPT63, a novel antigen secreted by *Mycobacterium tuberculosis*," Infection and Immunity 65(1):16-23 (1997).
Maratea,et al., "Deletion and fusion analysis of phage phi-X-174 lysis gene E," Gene 40:39-46 (1985).
Mathur and Kolttukudy, "Molecular cloning and sequencing of the gene for mycocerosic acid synthase, a novel falty acid elongating multifunctional enzyme, from *Mycobacterium tuberculosis* var. bovis *Bacillus* Calmette-Guerin," J. Biol. Chem. 267:19388-19395 (1992).
Matsumoto, et al., "Cloning and Sequencing of a Unique Antigen MPT70 from *Mycobacterium tuberculosis* H37Rv and Expression in BCG Using *E. coli*-Mycobacteria Shuttle Vector," Scand. J. Immunol. 41:281-287 (1995).
Moos, Isolation of Proteins for Microsequence Analysis, Current Protocols in Molecular Biology, pp. 10.19.1-10.19.12 (2000).
Mosmann and Coffan, "Th1 and TH2 Cells: Different Patterns of Lymphokine Secretion Lead to Different Functional Properties," Ann. Rev. Immunol. 7:145-173 (1989).
Murphy, et al., "Genetic construction, expression and melanoma-selective cytotoxicity of a diphtheria toxin-related alpha-melanocyte stimulating hormone fusion protein," PNAS USA 83: 8258-8262 (1986).
Nagai, et al., "Isolation and Partial Characterization of Major Protein Antigens in the Culture Fluid of *Mycobacterium tuberculosis*," Infection and Immunity 59(1):372-382 (1991).
Vekemans et al., "Immune Responses to Mycobacterial Antigens in the Gambian Populalion,", Infection and Immunity 72(1):381-88 (2004).
Von Eschen, et al., "The candidate tuberculosis vaccine Mtb72F/AS02A," Human Vaccines 5(7):475-82 (2009).
Vega-Lopez, et al., "Sequence and immunological characterization of a serine-rich antigen from *Mycobacterium leprae*," Infection and Immunity 61(5):2145-2153 (1993).
Vordemeier, et al., "Synthetic delivery system for tuberculosis vaccines: immunological evaluation of the *M. tuberculosis* 38 kDa protein entrapped in biodegradable PLG microparticles," Vaccine 13(16):1576-1582 (1995).
Wallis, et al., "Identification of Antigens of *Mycobacterium tuberculosis* Using Human Monoclonal Antibodies," J. Clin. Invest. 84:214-219 (1989).
Wang, et al., "Tuberculosis Vaccines: Past, Present and Future," Expert Rev. Vaccines 1(3):341-54 (2002).
Wang, et al., "A novel method for increasing the expression level of recombinant proteins," Protein Expression and Purification 30(1):124-133 (2003).
Webb, et al., "Molecular Cloning, Expression and Immunogenicity of MTB12," Infection & Immunity 66(9):4208-4214 (1998).
Wiegeshaus, et al., "Evaluation of the protective potency of new tuberculosis vaccines," Reviews of Infectious Diseases 11(Suppl. 2):5484-5490 (1989).
Wieles, et al., "Characterization of a *Mycobacterium leprae* Antigen Related to the Secreted *Mycobacterium tuberculosis* Protein MPT32," Infection and Immunity 62(1):252-258 (1994).
Wigler, et al., "Transformation of mammalian cells with an amplifiable dominant-acting gene," PNAS USA 77:3567-70 (1980).
Wiker and Harboe, "The Antigen 85 Complex: a Major Secretion Product of *Mycobacterium tuberculosis*," Microbiological Reviews 56(4):648-661 (1992).
Winter, "The Expression of Heat Shock Proteins and Cognate Genes During Plant Development," Results Probl. Cell Differ. 17: 85-105 (1991).
Yamaguchi, et al., "Cloning and Characterization of the Gene for Immunogenic Protein MPB64 of *Mycobacterium bovis* BDG," Infection and Immunity 57(1):283-288 (1989).
Young, et al., "Screening of a Recombinant Mycobacterial DNA Library with Polyclonal Antiserum and Molecular Weight Analysis of Expressed Antigens," Infection and Immunity 55(6):1421-1425 (1987).
Zimmerman, et al. "Immunization with peptide heteroconjugates primes a T helper cell type 1-associated antibody (IgG2a) response that recognizes the native epitope on the 38-kDa protein of *Mycobacterium tuberculosis*," Vaccine Res. 5(2):103-118 (1996).
Zitvogel, et al., "Eradiation of established murine tumors using a novel cell-free vaccine: dedritic cell-derived exosomes," Nature Med. 4:594-600 (1998).

Seq_NCBI_AF2122897, 1 page.
Seq_XP002416348_CDC1551, 2 pages.
Seq_NCBI AD000020 gi: 1717739 Dec. 10, 1996, 10 pages.
Seq_NCBI_AL021930.1, 2 pages.
Seq_NCBI_AL021930, 17 pages.
Seq_Database EMBL_U34848 "*Mycobacterium bovis* deletion region 1, 6kDa early secretory antigenic target (esat6) gene".
Seq_Accession No. O05907, Database:stpremb119, publicly available Jul. 1, 1997.
Seq_Accession No. O05908, Database:stpremb119, publicly available Jul. 1, 1997.
Seq_EMBL_MTCY7H7Bc, Accession No. Z95557, May 20, 1997.
Seq_EMBL_MTCY24G1, Accession No. Z83858, Jan. 13, 1997.
Seq_MTCY19G5, Accession No. Z77826, Jul. 31, 1996.
Seq_EMBL_MTCY261, Accession No. Z97559, Jul. 10, 1997.
Seq_EMBL_Z78020, XP002224823.
Seq_EMBL_P41403, XP002224824.
Seq_EMBL_Q50596, XP002224822.
Seq_EMBL_Z17372, XP002224825.
Seq_EMBL_U90239, XP002224826.
Seq_EMBL_P97048, XP002224827.
Seq_Accession_No_AU077540.
Sep_EMBL_P15712, (Apr. 1, 1990) "PBP-1 from *M. tuberculosis*" XP002359448.
Seq_Uniprot_Q79FV1.
Seq_Uniprot_O06267.
Seq_Uniprot_P96364.
Seq_Uniprot_O05300.
Seq_Sequence Alignment_SEQ ID No. 163-Mycobacterium smegmatis (Cirillo et al.).
Seq_Sequence Alignment_*Corynebacterium glutamicum*.
Seq_Sequence alignment_Mycobacterium segmatis_P41403, created Nov. 1995.
Seq_NCBI_214801_Rv0287 [Mycobacterium tuberculosisi H37Rv]).
Seq_EMBL_Q7U0G8-Hypothetical Protein Mb1207c, Oct. 31, 2006 XP002416347.
Seq_EMBL_050430-Hypothetical Protein Mb1207c, Oct. 31, 2006, XP002416348.
Seq_Compugen_P95242, 1997.
Seq_Compugen_P96363, 1997.
Cole, et al. "Deciphering the biology of *Mycobacterium tuberculosis* from the complete genome sequence"; Nature, vol. 393, pp. 537-544 (Jun. 1998).
Content, et al., "The Genes Coding for the Antigen 85 Complexes of *Mycobacterium tuberculosis* and *Mycobacterium bovis* BCG Are Members of a Gene Family: Cloning, Sequence Determination, and Genomic Organization of the Gene Coding for Antigen 85-C of *M. tuberculosis*"; Infection and Immunity, vol. 59, No. 9, pp. 3205-3212 (Sep. 1991).
Verbon, et al., "The 14,000-Molecular-Weight Antigen of *Mycobacterium tuberculosis* Is Related to the Alpha-Crystallin Family of Low-Molecular-Weight Heat Shock Proteins"; Journal of Bacteriology, vol. 174, No. 4, pp. 1352-1359 (Feb. 1992).
Needleman and Wunsch, "A General Method Applicable to the Search for Similarities in the Amino Acid Sequence of Two Proteins," J. Mol. Biol. 48:443 (1970).
Newport, et al., "A Mutation in the Interferon-γ-Receptor Gene and Susceptibility to Mycobacterial Infection," New Eng. J. of Medicine 335(26):1941-1949 (1996).
Nosoh, et al., Protein Stability and Stabilization through Protein Engineering, chap. 7, p. 197 (1991).
Oettinger, et al., "Cloning and B-cell-epitope mapping of MPT64 from *Mycobacterium tuberculosis* H37Rv," Infection and Immunity 62(5):2058-2064 (1994).
Orme, "Prospects for new vaccines against tuberculosis," Trends in Microbiology 3(10):401-404 (1995).
Ortega, et al., "Single-step purification on DEAE-sephacel of recombinant polypeptides produced in *Escherichia coli*," Biotechnology 10:795-798 (1992).
Pal, et al., "Immunization with extracellular proteins of *Mycobacterium tuberculosis* induces cell-mediated immune responses and substantial protective immunity in a guinea pig model of pulmonary tuberculosis", Infection and Immunity 60(11):4781-4792 (1992).
Pancholi, et al., "Dendritic cells efficiently immunoselect mycobacterial-reactive T cells in human blood, including clonable antigen-reactive precursors," Immunology 76(2):217-224 (1992).
Parker, et al., "Targeted Gene Walking Polymerase Chain Reactions," Nuc. Acids Res. 19: 3055-60 (1991).
Paul, Fundamental Immunology, chap. 8, 243-247 (1993).
Philipp, et al., "An integrated map of the genome of the tubercle bacillus, *Mycobacterium tuberculosis* H37Rv, and comparison with *Mycobacterium leprae*," PNAS USA 93(7):3132-3137 (1996).
Porath, et al., "Immobilized Metal Ion Affinity Chromatography, " Proto Exp. Purif. 3:263-281 (1992).
Pouthier, et al., "Anti-A60 immunoglobulin G in the serodiagnosis of tuberculosis in HIV-seropositive and seronegative patients," AIDS 8(9):1277-80 (1994).
Reed, et al., "Tuberculosis vaccine development: from mouse to man," Microbes and Infection 7(5-6):992-31 (2005).
Reed, et al., "Defined tuberculosis vaccine, Mtb72F/ASO2A,evidence of protection in cynomolgus monkeys," PNAS 106(7):2301-06 (2009).
Rhodes, et al., "Transformations of Maize by the Electroporation of Embryos," Methods Mol. Biol. 55:121-131 (1995).
Rinke De Wit, et al., "A *Mycobacterium leprae*-specific gene encoding an immunologically recognized 45 kDa protein," Mol. Microbiol. 10(4):829-838 (1993).
Rinke De Wit, et al., "Mycobacteria contains two groEL genes: the second *Mycobacterium leprae* groEL gene is arranged in an operon with groES," Mol. Microbiol. 6(14):1995-2007 (1992).
Riveau, et al., "Synthetic peptide vaccines against peptides and biological mediators," Trends in Pharmacological Sciences 11:194-198 (1990).
Roberts, et al., "Prediction of HIV peptide epitopes by a novel algorithm," AIDS Research and Human Retroviruses 12:593-610 (1996).
Romain, et al., "Identification of a *Mycobacterium bovis* BCG 45/47-Kilodalton Antigen Complex, an Immunodominant Target for Antibody Response after Immunization with Living Bacteria," Infection and Immunity 61(2):742-750 (1993).
Romain, et al., "Isolation of a proline-rich mycobacterial protein eliciting delayed-type hypersensitivity reactions only in guinea pigs immunized with living mycobacteria," PNAS USA 90:5322-5326 (1993).
Romain, et al., "Preparation of Tuberculin Antigen L," Ann. Inst. Pasteur/Microbiol. 136B:235-248 (1985).
Romano, et al., "Immunogenicity and protective efficacy of tuberculosis subunit vaccines expression PPE44 (Rv2770c)," Vaccine, 26(48):6053-63 (2008).
Rolland, "From Genes to Gene Medicines: Recent Advances in Nonviral Gene Delivery," Crit. Rev. Therap. Drug Carrier Systems 15:143-198 (1998).
Rosenfeld, et al., "Adenovirus-Mediated Transfere of a Recombinant Alpha-1 Antitrypsin Gene to Lung Epithelium in Vivo," Science 252:431-434 (1991).
Rossolini, et al., "Use of deoxyinosine-containing primers versus degenerate primers," Mol. Cell. Probes 8:91-98 (1994).
Sanderson, et al., "Identification of a CD4+ T Cell-stimulating Antigen of Pathogenic Bacteria by Expression Cloning," J. Exp. Med. 182(6):1751-1757 (1995).
Sato, et al., "Immunostimulatory DNA Sequences Necessary for Effective Intradermal Gene Immunization," Science 273:352 (1996).
Scharf, et al., "Heat Stress Promoters and Transcription Factors," Results Probl. Cell Differ. 20:125-162 (1994).
Schorey, "A *Mycobacterium leprae* Gene Encoding a Fibronectin Binding Protein is Used for Efficient Invasion Epithelial Cells and Schwann Cells," Infection and Immunity 63(7):2652-2657 (1995).
Shinnick, "The 65-Kilodalton Antigen of *Mycobacterioum tuberculosis*," J. of Bacteriology 169(3): 1080-1088 (1987).
Singh, et al., "In Vitro Characterization of T Cells from Mycobacterium W-Vaccinated Mice," Infection and Immunity 60(1):257-263 (1992).

Sinha, et al., "Immunological properties of a 30 Kda secretory protein of *Mycobacterium tuberculosis* H37RA," Vaccine 15(6-7): 689-99 (1997).

Simonney, et al., "Analysis of the immunological humoral response to *Mycobacterium tuberculosis* glycolipid antigens (DAT, PGLTb1) for diagnosis of tuberculosis in HIV-seropositive and seronegative patients," Eur. J. of Clin. Microbiology and Infectious Disease 14(10):883-891 (1995).

Skeiky, et al., "Cloning Expression and Immunological Evaluation of Two Putative Secreted Serine Protease Antigens of *Mycrobactenum tuberculosis*," Infection and Immunity 67(8): 3998-4007 (1999).

Skeiky, et al., "LeIF:a recombinant leishmania protein that induces an IL-12 mediated Th cytokine profile," J. of Immunology 161: 6171-79 (1998).

Skeiky, et al., "Differential immune responses and protective efficacy induced by components of a tuberculosis polyprotein vaccine, Mtb72F, delivered as naked DNA or recombinant protein," J. of Immunology 172(12):7618-28 (2004).

Skorko-Glonek, "Comparison of the structure of wild-type HtrA heat shock protease and mutant HtrA proteins. A Fourier transform infrared spectroscopic study," JBC 270(19): 11140-11146 (1995).

Skuce, et al., "Discrimination of *M. tuberculosis* complex bacterial using novel VNTR-PCR targets," Microbiology 148(2):519-28 (2002).

Sorensen, et al., "Purification and characterization of a low-molecular-mass T-cell antigen secreted by *Mycobacterium tuberculosis*," Infection and Immunity 63(5): 1710-1717 (1995).

Stoute, et al., "A Preliminary Evaluation of a Recombinant Circumsporozoite Protein Vaccine Against Plasmodium Falciparum Malaria," New Engl. J. Med. 336:86-91 (1997).

St. Pierre, et al., "A refined vector system for the in vitro construction of single-copy transcriptional or translational fusions to lacZ," Gene169:65-68 (1996).

Timmerman and Levy, "Dendritic Cell Vaccines for Cancer Immunotherapy," Ann. Rev. Med 50: 507-529 (1999).

Triglia, et al., "A Procedure for In Vitro Amplification of DNA Sequences that Lie Outside the Boundaries of Known Sequences," Nucl. Acids Res. 16:8186 (1988).

Tsenova, et al. "Evaluation of the Mtb72F Polyprotein Vaccine in a Rabbit Model," Infection and Immunity 74(4):2922-401 (2006).

Ulmer, et al., "Heterologous Protection Against Influenze by Injection of DNA Encoding a Viral Protein," Science 259:1745-1749 (1993).

Van Pittius, et al., "Evolution and expansion of the *M. tuberculosis* PE and PPE multigene families and their association with the duplication of the ESAT-6 (esx) gene cluster regions," BML Evolutionary Biology 6(1):95 (2006).

Van Soolingen, et al., "Host-Mediated Modification of Pvull Restriction in *Mycobacterium tuberculosis*," J. of Bactreriology 178(1):78-84 (1996).

Langermans, et al., Protection of macaques against *Mycobacterium tuberculosis* infection by a subunit vaccine based on a fusion protein of antigen 85B and ESAT 6, Vaccine 23:2740-50 (2005).

Mustafa, et al., "Immunogenicity of *Mycobacterium tuberculosis* Antigens in *Mycobacterium bovis* BCG-Vaccinated and *M. bovis*-infected Cattie", Infection and Immunity 74(8)4565-72 (2006).

Reece, et al, "Skin Text Performed with Highly Purified *Mycobacterium tuberculosis* Recombinant Protein Triggers Tuberculin Shock in Infected Guinea Pigs," Infection and Immunity 73(6):3301-06 (2005).

Skeiky, et al., "T Cell Expression Cloning of a *Mycobacterium tuberculosis* Gene Encoding a Protective Antigen Associated with the Early Control of Infection," J. of Immunology 155:7140-49 (2000).

Skeiky, et al., "Protection of mice and guinea pigs against tuberculosis induced by immunization with a single *Mycobacterium tuberculosis* recombinant antigen, MTB41," Vaccine 23:3937-45 (2005).

Tanghe, et al., "Improved Immunogenicity and Protective Efficacy of a Tuberculosis DNA Vaccine Encoding Ag85 by Protein Boosting,"Infection and Immunity 69(5):3041-47 (2001).

Williams, et al., "Evaluation of vaccines in the EU TB Vaccine Cluster using a guinea pig aerosol infection model of tuberculosis," Tuberculosis 85:29-38 (2005).

Final Office Action for U.S. Appl. No. 11/801,112, 2011.

Office Action for U.S. Appl. No. 11/927,566, 2010.

Office Action for U.S. Appl. No. 11/978,786, 2011.

Advisory Action for U.S. Appl. No. 11/981,459, 2011.

Office Action for U.S. Appl. No. 12/490,272, 2011.

Office Action for U.S. Appl. No. 12/698,893, 2010.

Office Action for U.S. Appl. No. 12/698,976, 2010.

* cited by examiner

FIGURE 1

SEQ ID NO:1
SIZE: 2181
DNA--MTB32-MTB39F

```
CATATGCATC ACCATCACCA TCACGCCCCG CCGGCCTTGT CGCAGGACCG GTTCGCCGAC 60
TTCCCCGCGC TGCCCCTCGA CCCGTCCGCG ATGGTCGCCC AAGTGGGGCC ACAGGTGGTC 120
AACATCAACA CCAAACTGGG CTACAACAAC GCCGTGGGCG CCGGGACCGG CATCGTCATC 180
GATCCCAACG GTGTCGTGCT GACCAACAAC CACGTGATCG CGGGCGCCAC CGACATCAAT 240
GCGTTCAGCG TCGGCTCCGG CCAAACCTAC GGCGTCGATG TGGTCGGGTA TGACCGCACC 300
CAGGATGTCG CGGTGCTGCA GCTGCGCGGT GCCGGTGGCC TGCCGTCGGC GGCGATCGGT 360
GGCGGCGTCG CGGTTGGTGA GCCCGTCGTC GCGATGGGCA ACAGCGGTGG GCAGGGCGGA 420
ACGCCCCGTG CGGTGCCTGG CAGGGTGGTC GCGCTCGGCC AAACCGTGCA GGCGTCGGAT 480
TCGCTGACCG GTGCCGAAGA GACATTGAAC GGGTTGATCC AGTTCGATGC CGCGATCCAG 540
CCCGGTGATG CGGGCGGGCC CGTCGTCAAC GGCCTAGGAC AGGTGGTCGG TATGAACACG 600
GCCGCGTCCG ATAACTTCCA GCTGTCCCAG GGTGGGCAGG GATTCGCCAT TCCGATCGGG 660
CAGGCGATGG CGATCGCGGG CCAGATCCGA TCGGGTGGGG GGTCACCCAC CGTTCATATC 720
GGGCCTACCG CCTTCCTCGG CTTGGGTGTT GTCGACAACA ACGGCAACGG CGCACGAGTC 780
CAACGCGTGG TCGGGAGCGC TCCGGCGGCA AGTCTCGGCA TCTCCACCGG CGACGTGATC 840
ACCGCGGTCG ACGGCGCTCC GATCAACTCG GCCACCGCGA TGGCGGACGC GCTTAACGGG 900
CATCATCCCG GTGACGTCAT CTCGGTGACC TGGCAAACCA AGTCGGGCGG CACGCGTACA 960
GGGAACGTGA CATTGGCCGA GGGACCCCCG GCCGAATTCA TGGTGGATTT CGGGGCGTTA 1020
CCACCGGAGA TCAACTCCGC GAGGATGTAC GCCGGCCCGG GTTCGGCCTC GCTGGTGGCC 1080
GCGGCTCAGA TGTGGGACAG CGTGGCGAGT GACCTGTTTT CGGCCGCGTC GGCGTTTCAG 1140
TCGGTGGTCT GGGGTCTGAC GGTGGGGTCG TGGATAGGTT CGTCGGCGGG TCTGATGGTG 1200
GCGGCGGCCT CGCCGTATGT GGCGTGGATG AGCGTCACCG CGGGGCAGGC CGAGCTGACC 1260
GCCGCCCAGG TCCGGGTTGC TGCGGCGGCC TACGAGACGG CGTATGGGCT GACGGTGCCC 1320
CCGCCGGTGA TCGCCGAGAA CCGTGCTGAA CTGATGATTC TGATAGCGAC CAACCTCTTG 1380
GGGCAAAACA CCCCGGCGAT CGCGGTCAAC GAGGCCGAAT ACGGCGAGAT GTGGGCCCAA 1440
GACGCCGCCG CGATGTTTGG CTACGCCGCG GCGACGGCGA CGGCGACGGC GACGTTGCTG 1500
CCGTTCGAGG AGGCGCCGGA GATGACCAGC GCGGGTGGGC TCCTCGAGCA GGCCGCCGCG 1560
GTCGAGGAGG CCTCCGACAC CGCCGCGGCG AACCAGTTGA TGAACAATGT GCCCCAGGCG 1620
CTGCAACAGC TGGCCCAGCC CACGCAGGGC ACCACGCCTT CTTCCAAGCT GGGTGGCCTG 1680
TGGAAGACGG TCTCGCCGCA TCGGTCGCCG ATCAGCAACA TGGTGTCGAT GGCCAACAAC 1740
CACATGTCGA TGACCAACTC GGGTGTGTCG ATGACCAACA CCTTGAGCTC GATGTTGAAG 1800
GGCTTTGCTC CGGCGGCGGC CGCCCAGGCC GTGCAAACCG CGGCGCAAAA CGGGGTCCGG 1860
GCGATGAGCT CGCTGGGCAG CTCGCTGGGT TCTTCGGGTC TGGGCGGTGG GGTGGCCGCC 1920
AACTTGGGTC GGGCGGCCTC GGTCGGTTCG TTGTCGGTGC CGCAGGCCTG GGCCGCGGCC 1980
AACCAGGCAG TCACCCCGGC GGCGCGGGCG CTGCCGCTGA CCAGCCTGAC CAGCGCCGCG 2040
GAAAGAGGGC CCGGGCAGAT GCTGGGCGGG CTGCCGGTGG GGCAGATGGG CGCCAGGGCC 2100
GGTGGTGGGC TCAGTGGTGT GCTGCGTGTT CCACCGCGAC CCTATGTGAT GCCGCATTCT 2160
CCGGCAGCCG GCTAAGGATC C                                           2181
```

SEQ ID NO:2 FIG 2A
SIZE: 723
PRT--MTB32-MTB38F

Met His His His His His His Ala Pro Pro Ala Leu Ser Gln Asp Arg
5 10 15

Phe Ala Asp Phe Pro Ala Leu Pro Leu Asp Pro Ser Ala Met Val Ala
20 25 30

Gln Val Gly Pro Gln Val Val Asn Ile Asn Thr Lys Leu Gly Tyr Asn
35 40 45

Asn Ala Val Gly Ala Gly Thr Gly Ile Val Ile Asp Pro Asn Gly Val
50 55 60

Val Leu Thr Asn Asn His Val Ile Ala Gly Ala Thr Asp Ile Asn Ala
65 70 75 80

Phe Ser Val Gly Ser Gly Gln Thr Tyr Gly Val Asp Val Val Gly Tyr
85 90 95

Asp Arg Thr Gln Asp Val Ala Val Leu Gln Leu Arg Gly Ala Gly Gly
100 105 110

Leu Pro Ser Ala Ala Ile Gly Gly Gly Val Ala Val Gly Glu Pro Val
115 120 125

Val Ala Met Gly Asn Ser Gly Gly Gln Gly Gly Thr Pro Arg Ala Val
130 135 140

Pro Gly Arg Val Val Ala Leu Gly Gln Thr Val Gln Ala Ser Asp Ser
145 150 155 160

Leu Thr Gly Ala Glu Glu Thr Leu Asn Gly Leu Ile Gln Phe Asp Ala
165 170 175

Ala Ile Gln Pro Gly Asp Ala Gly Gly Pro Val Val Asn Gly Leu Gly
180 185 190

Gln Val Val Gly Met Asn Thr Ala Ala Ser Asp Asn Phe Gln Leu Ser
195 200 205

Gln Gly Gly Gln Gly Phe Ala Ile Pro Ile Gly Gln Ala Met Ala Ile
210 215 220

Ala Gly Gln Ile Arg Ser Gly Gly Gly Ser Pro Thr Val His Ile Gly
225 230 235 240

Pro Thr Ala Phe Leu Gly Leu Gly Val Val Asp Asn Asn Gly Asn Gly
245 250 255

Ala Arg Val Gln Arg Val Val Gly Ser Ala Pro Ala Ala Ser Leu Gly
260 265 270

Ile Ser Thr Gly Asp Val Ile Thr Ala Val Asp Gly Ala Pro Ile Asn
275 280 285

Ser Ala Thr Ala Met Ala Asp Ala Leu Asn Gly His His Pro Gly Asp
290 295 300

FIG 2B

Val Ile Ser Val Thr Trp Gln Thr Lys Ser Gly Gly Thr Arg Thr Gly
305 310 315 320

Asn Val Thr Leu Ala Glu Gly Pro Pro Ala Glu Phe Met Val Asp Phe
325 330 335

Gly Ala Leu Pro Pro Glu Ile Asn Ser Ala Arg Met Tyr Ala Gly Pro
340 345 350

Gly Ser Ala Ser Leu Val Ala Ala Ala Gln Met Trp Asp Ser Val Ala
355 360 365

Ser Asp Leu Phe Ser Ala Ala Ser Ala Phe Gln Ser Val Val Trp Gly
370 375 380

Leu Thr Val Gly Ser Trp Ile Gly Ser Ser Ala Gly Leu Met Val Ala
385 390 395 400

Ala Ala Ser Pro Tyr Val Ala Trp Met Ser Val Thr Ala Gly Gln Ala
405 410 415

Glu Leu Thr Ala Ala Gln Val Arg Val Ala Ala Ala Ala Tyr Glu Thr
420 425 430

Ala Tyr Gly Leu Thr Val Pro Pro Pro Val Ile Ala Glu Asn Arg Ala
435 440 445

Glu Leu Met Ile Leu Ile Ala Thr Asn Leu Leu Gly Gln Asn Thr Pro
450 455 460

Ala Ile Ala Val Asn Glu Ala Glu Tyr Gly Glu Met Trp Ala Gln Asp
465 470 475 480

Ala Ala Ala Met Phe Gly Tyr Ala Ala Ala Thr Ala Thr Ala Thr Ala
485 490 495

Thr Leu Leu Pro Phe Glu Glu Ala Pro Glu Met Thr Ser Ala Gly Gly
500 505 510

Leu Leu Glu Gln Ala Ala Ala Val Glu Glu Ala Ser Asp Thr Ala Ala
515 520 525

Ala Asn Gln Leu Met Asn Asn Val Pro Gln Ala Leu Gln Gln Leu Ala
530 535 540

Gln Pro Thr Gln Gly Thr Thr Pro Ser Ser Lys Leu Gly Gly Leu Trp
545 550 555 560

Lys Thr Val Ser Pro His Arg Ser Pro Ile Ser Asn Met Val Ser Met
565 570 575

Ala Asn Asn His Met Ser Met Thr Asn Ser Gly Val Ser Met Thr Asn
580 585 590

Thr Leu Ser Ser Met Leu Lys Gly Phe Ala Pro Ala Ala Ala Ala Gln
595 600 605

Ala Val Gln Thr Ala Ala Gln Asn Gly Val Arg Ala Met Ser Ser Leu
610 615 620

FIG 2C

Gly Ser Ser Leu Gly Ser Ser Gly Leu Gly Gly Gly Val Ala Ala Asn
625 630 635 640

Leu Gly Arg Ala Ala Ser Val Gly Ser Leu Ser Val Pro Gln Ala Trp
645 650 655

Ala Ala Ala Asn Gln Ala Val Thr Pro Ala Ala Arg Ala Leu Pro Leu
660 665 670

Thr Ser Leu Thr Ser Ala Ala Glu Arg Gly Pro Gly Gln Met Leu Gly
675 680 685

Gly Leu Pro Val Gly Gln Met Gly Ala Arg Ala Gly Gly Gly Leu Ser
690 695 700

Gly Val Leu Arg Val Pro Pro Arg Pro Tyr Val Met Pro His Ser Pro
705 710 715 720

Ala Ala Gly

FIGURE 3

SEQ ID NO:3
SIZE: 3030
DNA--MTB-102F

```
ATGCATCACC ATCACCATCA CGCCCCGCCG GCCTTGTCGC AGGACCGGTT CGCCGACTTC 60
CCCGCGCTGC CCCTCGACCC GTCCGCGATG GTCGCCCAAG TGGGGCCACA GGTGGTCAAC 120
ATCAACACCA AACTGGGCTA CAACAACGCC GTGGGCGCCG GGACCGGCAT CGTCATCGAT 180
CCCAACGGTG TCGTGCTGAC CAACAACCAC GTGATCGCGG GCGCCACCGA CATCAATGCG 240
TTCAGCGTCG GCTCCGGCCA AACCTACGGC GTCGATGTGG TCGGGTATGA CCGCACCCAG 300
GATGTCGCGG TGCTGCAGCT GCGCGGTGCC GGTGGCCTGC CGTCGGCGGC GATCGGTGGC 360
GGCGTCGCGG TTGGTGAGCC CGTCGTCGCG ATGGGCAACA GCGGTGGGCA GGGCGGAACG 420
CCCCGTGCGG TGCCTGGCAG GGTGGTCGCG CTCGGCCAAA CCGTGCAGGC GTCGGATTCG 480
CTGACCGGTG CCGAAGAGAC ATTGAACGGG TTGATCCAGT TCGATGCCGC GATCCAGCCC 540
GGTGATGCGG GCGGGCCCGT CGTCAACGGC CTAGGACAGG TGGTCGGTAT GAACACGGCC 600
GCGTCCGATA ACTTCCAGCT GTCCCAGGGT GGGCAGGGAT TCGCCATTCC GATCGGGCAG 660
GCGATGGCGA TCGCGGGCCA GATCCGATCG GGTGGGGGGT CACCCACCGT TCATATCGGG 720
CCTACCGCCT TCCTCGGCTT GGGTGTTGTC GACAACAACG GCAACGGCGC ACGAGTCCAA 780
CGCGTGGTCG GGAGCGCTCC GGCGGCAAGT CTCGGCATCT CCACCGGCGA CGTGATCACC 840
GCGGTCGACG GCGCTCCGAT CAACTCGGCC ACCGCGATGG CGGACGCGCT TAACGGGCAT 900
CATCCCGGTG ACGTCATCTC GGTGACCTGG CAAACCAAGT CGGGCGGCAC GCGTACAGGG 960
AACGTGACAT TGGCCGAGGG ACCCCCGGCC GAATTCATGG TGGATTTCGG GGCGTTACCA 1020
CCGGAGATCA ACTCCGCGAG GATGTACGCC GGCCCGGGTT CGGCCTCGCT GGTGGCCGCG 1080
GCTCAGATGT GGGACAGCGT GGCGAGTGAC CTGTTTTCGG CCGCGTCGGC GTTTCAGTCG 1140
GTGGTCTGGG GTCTGACGGT GGGGTCGTGG ATAGGTTCGT CGGCGGGTCT GATGGTGGCG 1200
GCGGCCTCGC CGTATGTGGC GTGGATGAGC GTCACCGCGG GGCAGGCCGA GCTGACCGCC 1260
GCCCAGGTCC GGGTTGCTGC GGCGGCCTAC GAGACGGCGT ATGGGCTGAC GGTGCCCCCG 1320
CCGGTGATCG CCGAGAACCG TGCTGAACTG ATGATTCTGA TAGCGACCAA CCTCTTGGGG 1380
CAAAACACCC CGGCGATCGC GGTCAACGAG GCCGAATACG GCGAGATGTG GGCCCAAGAC 1440
GCCGCCGCGA TGTTTGGCTA CGCCGCGGCG ACGGCGACGG CGACGGCGAC GTTGCTGCCG 1500
TTCGAGGAGG CGCCGGAGAT GACCAGCGCG GGTGGGCTCC TCGAGCAGGC CGCCGCGGTC 1560
GAGGAGGCCT CCGACACCGC CGCGGCGAAC CAGTTGATGA ACAATGTGCC CCAGGCGCTG 1620
CAACAGCTGG CCCAGCCCAC GCAGGGCACC ACGCCTTCTT CCAAGCTGGG TGGCCTGTGG 1680
AAGACGGTCT CGCCGCATCG GTCGCCGATC AGCAACATGG TGTCGATGGC CAACAACCAC 1740
ATGTCGATGA CCAACTCGGG TGTGTCGATG ACCAACACCT TGAGCTCGAT GTTGAAGGGC 1800
TTTGCTCCGG CGGCGGCCGC CCAGGCCGTG CAAACCGCGG CGCAAAACGG GGTCCGGGCG 1860
ATGAGCTCGC TGGGCAGCTC GCTGGGTTCT TCGGGTCTGG GCGGTGGGGT GGCCGCCAAC 1920
TTGGGTCGGG CGGCCTCGGT CGGTTCGTTG TCGGTGCCGC AGGCCTGGGC CGCGGCCAAC 1980
CAGGCAGTCA CCCCGGCGGC GCGGGCGCTG CCGCTGACCA GCCTGACCAG CGCCGCGGAA 2040
AGAGGGCCCG GGCAGATGCT GGGCGGGCTG CCGGTGGGGC AGATGGGCGC CAGGGCCGGT 2100
GGTGGGCTCA GTGGTGTGCT GCGTGTTCCG CCGCGACCCT ATGTGATGCC GCATTCTCCG 2160
GCAGCCGGCA AGCTTTTCTC CCGGCCGGGG CTGCCGGTCG AGTACCTGCA GGTGCCGTCG 2220
CCGTCGATGG GCCGCGACAT CAAGGTTCAG TTCCAGAGCG GTGGGAACAA CTCACCTGCG 2280
GTTTATCTGC TCGACGGCCT GCGCGCCCAA GACGACTACA ACGGCTGGGA TATCAACACC 2340
CCGGCGTTCG AGTGGTACTA CCAGTCGGGA CTGTCGATAG TCATGCCGGT CGGCGGGCAG 2400
TCCAGCTTCT ACAGCGACTG GTACAGCCCG GCCTGCGGTA AGGCTGGCTG CCAGACTTAC 2460
AAGTGGGAAA CCTTCCTGAC CAGCGAGCTG CCGCAATGGT TGTCCGCCAA CAGGGCCGTG 2520
AAGCCCACCG GCAGCGCTGC AATCGGCTTG TCGATGGCCG GCTCGTCGGC AATGATCTTG 2580
GCCGCCTACC ATCCCCAGCA GTTCATCTAC GCCGGCTCGC TGTCGGCCCT GCTGGACCCC 2640
TCTCAGGGGA TGGGGCCTAG CCTGATCGGC CTCGCGATGG GTGACGCCGG CGGTTACAAG 2700
GCCGCAGACA TGTGGGGTCC CTCGAGTGAC CCGGCATGGG AGCGCAACGA CCCTACGCAG 2760
CAGATCCCCA AGCTGGTCGC AAACAACACC CGGCTATGGG TTTATTGCGG GAACGGCACC 2820
CCGAACGAGT TGGGCGGTGC CAACATACCC GCCGAGTTCT TGGAGAACTT CGTTCGTAGC 2880
AGCAACCTGA AGTTCCAGGA TGCGTACAAC GCCGCGGGCG GGCACAACGC CGTGTTCAAC 2940
TTCCCGCCCA ACGGCACGCA CAGCTGGGAG TACTGGGGCG CTCAGCTCAA CGCCATGAAG 3000
GGTGACCTGC AGAGTTCGTT AGGCGCCGGC 3030
```

SEQ ID NO:4
SIZE: 1010
PRT--MTB102F

FIG 4A

Met His His His His His His Ala Pro Pro Ala Leu Ser Gln Asp Arg
5 10 15

Phe Ala Asp Phe Pro Ala Leu Pro Leu Asp Pro Ser Ala Met Val Ala
20 25 30

Gln Val Gly Pro Gln Val Val Asn Ile Asn Thr Lys Leu Gly Tyr Asn
35 40 45

Asn Ala Val Gly Ala Gly Thr Gly Ile Val Ile Asp Pro Asn Gly Val
50 55 60

Val Leu Thr Asn Asn His Val Ile Ala Gly Ala Thr Asp Ile Asn Ala
65 70 75 80

Phe Ser Val Gly Ser Gly Gln Thr Tyr Gly Val Asp Val Val Gly Tyr
85 90 95

Asp Arg Thr Gln Asp Val Ala Val Leu Gln Leu Arg Gly Ala Gly Gly
100 105 110

Leu Pro Ser Ala Ala Ile Gly Gly Gly Val Ala Val Gly Glu Pro Val
115 120 125

Val Ala Met Gly Asn Ser Gly Gly Gln Gly Gly Thr Pro Arg Ala Val
130 135 140

Pro Gly Arg Val Val Ala Leu Gly Gln Thr Val Gln Ala Ser Asp Ser
145 150 155 160

Leu Thr Gly Ala Glu Glu Thr Leu Asn Gly Leu Ile Gln Phe Asp Ala
165 170 175

Ala Ile Gln Pro Gly Asp Ala Gly Gly Pro Val Val Asn Gly Leu Gly
180 185 190

Gln Val Val Gly Met Asn Thr Ala Ala Ser Asp Asn Phe Gln Leu Ser
195 200 205

Gln Gly Gly Gln Gly Phe Ala Ile Pro Ile Gly Gln Ala Met Ala Ile
210 215 220

Ala Gly Gln Ile Arg Ser Gly Gly Gly Ser Pro Thr Val His Ile Gly
225 230 235 240

Pro Thr Ala Phe Leu Gly Leu Gly Val Val Asp Asn Asn Gly Asn Gly
245 250 255

Ala Arg Val Gln Arg Val Val Gly Ser Ala Pro Ala Ala Ser Leu Gly
260 265 270

Ile Ser Thr Gly Asp Val Ile Thr Ala Val Asp Gly Ala Pro Ile Asn
275 280 285

Ser Ala Thr Ala Met Ala Asp Ala Leu Asn Gly His His Pro Gly Asp
290 295 300

FIG 4B

Val Ile Ser Val Thr Trp Gln Thr Lys Ser Gly Gly Thr Arg Thr Gly
305 310 315 320

Asn Val Thr Leu Ala Glu Gly Pro Pro Ala Glu Phe Met Val Asp Phe
325 330 335

Gly Ala Leu Pro Pro Glu Ile Asn Ser Ala Arg Met Tyr Ala Gly Pro
340 345 350

Gly Ser Ala Ser Leu Val Ala Ala Ala Gln Met Trp Asp Ser Val Ala
355 360 365

Ser Asp Leu Phe Ser Ala Ala Ser Ala Phe Gln Ser Val Val Trp Gly
370 375 380

Leu Thr Val Gly Ser Trp Ile Gly Ser Ser Ala Gly Leu Met Val Ala
385 390 395 400

Ala Ala Ser Pro Tyr Val Ala Trp Met Ser Val Thr Ala Gly Gln Ala
405 410 415

Glu Leu Thr Ala Ala Gln Val Arg Val Ala Ala Ala Ala Tyr Glu Thr
420 425 430

Ala Tyr Gly Leu Thr Val Pro Pro Pro Val Ile Ala Glu Asn Arg Ala
435 440 445

Glu Leu Met Ile Leu Ile Ala Thr Asn Leu Leu Gly Gln Asn Thr Pro
450 455 460

Ala Ile Ala Val Asn Glu Ala Glu Tyr Gly Glu Met Trp Ala Gln Asp
465 470 475 480

Ala Ala Ala Met Phe Gly Tyr Ala Ala Ala Thr Ala Thr Ala Thr Ala
485 490 495

Thr Leu Leu Pro Phe Glu Glu Ala Pro Glu Met Thr Ser Ala Gly Gly
500 505 510

Leu Leu Glu Gln Ala Ala Ala Val Glu Glu Ala Ser Asp Thr Ala Ala
515 520 525

Ala Asn Gln Leu Met Asn Asn Val Pro Gln Ala Leu Gln Gln Leu Ala
530 535 540

Gln Pro Thr Gln Gly Thr Thr Pro Ser Ser Lys Leu Gly Gly Leu Trp
545 550 555 560

Lys Thr Val Ser Pro His Arg Ser Pro Ile Ser Asn Met Val Ser Met
565 570 575

Ala Asn Asn His Met Ser Met Thr Asn Ser Gly Val Ser Met Thr Asn
580 585 590

Thr Leu Ser Ser Met Leu Lys Gly Phe Ala Pro Ala Ala Ala Ala Gln
595 600 605

Ala Val Gln Thr Ala Ala Gln Asn Gly Val Arg Ala Met Ser Ser Leu
610 615 620

FIG 4C

Gly Ser Ser Leu Gly Ser Ser Gly Leu Gly Gly Gly Val Ala Ala Asn
625 630 635 640

Leu Gly Arg Ala Ala Ser Val Gly Ser Leu Ser Val Pro Gln Ala Trp
645 650 655

Ala Ala Ala Asn Gln Ala Val Thr Pro Ala Ala Arg Ala Leu Pro Leu
660 665 670

Thr Ser Leu Thr Ser Ala Ala Glu Arg Gly Pro Gly Gln Met Leu Gly
675 680 685

Gly Leu Pro Val Gly Gln Met Gly Ala Arg Ala Gly Gly Gly Leu Ser
690 695 700
A

Gly Val Leu Arg Val Pro Pro Arg Pro Tyr Val Met Pro His Ser Pro
705 710 715 720

Ala Ala Gly Lys Leu Phe Ser Arg Pro Gly Leu Pro Val Glu Tyr Leu
725 730 735

Gln Val Pro Ser Pro Ser Met Gly Arg Asp Ile Lys Val Gln Phe Gln
740 745 750

Ser Gly Gly Asn Asn Ser Pro Ala Val Tyr Leu Leu Asp Gly Leu Arg
755 760 765

Ala Gln Asp Asp Tyr Asn Gly Trp Asp Ile Asn Thr Pro Ala Phe Glu
770 775 780

Trp Tyr Tyr Gln Ser Gly Leu Ser Ile Val Met Pro Val Gly Gly Gln
785 790 795 800

Ser Ser Phe Tyr Ser Asp Trp Tyr Ser Pro Ala Cys Gly Lys Ala Gly
805 810 815

Cys Gln Thr Tyr Lys Trp Glu Thr Phe Leu Thr Ser Glu Leu Pro Gln
820 825 830

Trp Leu Ser Ala Asn Arg Ala Val Lys Pro Thr Gly Ser Ala Ala Ile
835 840 845

Gly Leu Ser Met Ala Gly Ser Ser Ala Met Ile Leu Ala Ala Tyr His
850 855 860

Pro Gln Gln Phe Ile Tyr Ala Gly Ser Leu Ser Ala Leu Leu Asp Pro
865 870 875 880

Ser Gln Gly Met Gly Pro Ser Leu Ile Gly Leu Ala Met Gly Asp Ala
885 890 895

Gly Gly Tyr Lys Ala Ala Asp Met Trp Gly Pro Ser Ser Asp Pro Ala
900 905 910

Trp Glu Arg Asn Asp Pro Thr Gln Gln Ile Pro Lys Leu Val Ala Asn
915 920 925

Asn Thr Arg Leu Trp Val Tyr Cys Gly Asn Gly Thr Pro Asn Glu Leu
930 935 940

Gly Gly Ala Asn Ile Pro Ala Glu Phe Leu Glu Asn Phe Val Arg Ser

FIG 4D 945 950 955 960

Figure 4D:
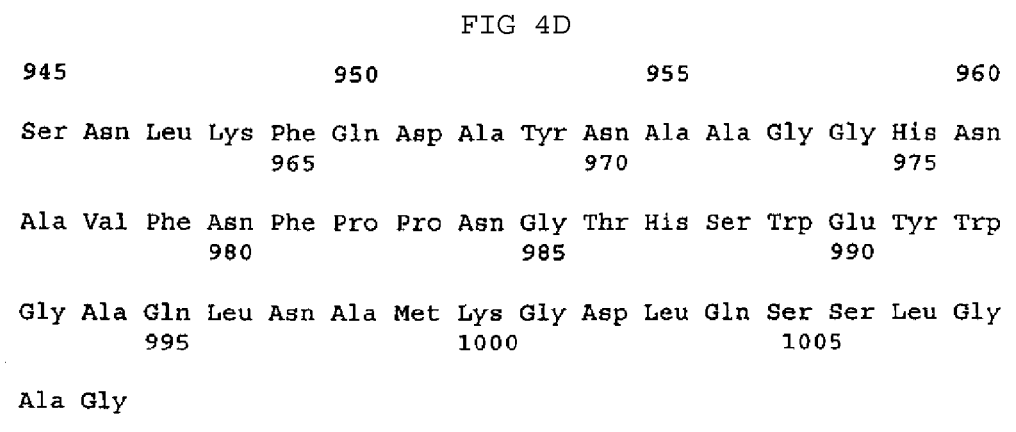

Ser Asn Leu Lys Phe Gln Asp Ala Tyr Asn Ala Ala Gly Gly His Asn
965 970 975

Ala Val Phe Asn Phe Pro Pro Asn Gly Thr His Ser Trp Glu Tyr Trp
980 985 990

Gly Ala Gln Leu Asn Ala Met Lys Gly Asp Leu Gln Ser Ser Leu Gly
995 1000 1005

Ala Gly

FIGURE 5

SEQ ID NO:5
Size:2808
DNA--r95F (MTB72F-MAPS)

CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCATGT CCTGCGGTAA CGCCAAGATC 2220
AACTCTCCCG CGCCGTCCTT CGAGGAGGTG GCGCTCATGC CCAACGGCAG CTTCAAGAAG 2280
ATCAGCCTCT CCTCCTACAA GGGCAAGTGG GTCGTGCTCT TCTTCTACCC GCTCGACTTC 2340
ACCTTCGTGT GCCCGACAGA GGTCATCGCG TTCTCCGACA GCGTGAGTCG CTTCAACGAG 2400
CTCAACTGCG AGGTCCTCGC GTGCTCGATA GACAGCGAGT ACGCGCACCT GCAGTGGACG 2460
CTGCAGGACC GCAAGAAGGG CGGCCTCGGG ACCATGGCGA TCCCAATGCT AGCCGACAAG 2520
ACCAAGAGCA TCGCTCGTTC CTACGGCGTG CTGGAGGAGA GCCAGGGCGT GGCCTACCGC 2580
GGTCTCTTCA TCATCGACCC CCATGGCATG CTGCGTCAGA TCACCGTCAA TGACATGCCG 2640
GTGGGCCGCA GCGTGGAGGA GGTTCTACGC CTGCTGGAGG CTTTTCAGTT CGTGGAGAAG 2700
CACGGCGAGG TGTGCCCCGC GAACTGGAAG AAGGGCGCCC CCACGATGAA GCCGGAACCG 2760
AATGCGTCTG TCGAGGGATA CTTCAGCAAG CAGTAAGGAT CCACTAGT 2808

FIGURE 6

SEQ ID NO:6
Size: 2637
DNA--MTB89F MTB72F-Erd14

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCATGG CCACCACCCT TCCCGTTCAG 2220
CGCCACCCGC GGTCCCTCTT CCCCGAGTTT TCTGAGCTGT TCGCGGCCTT CCCGTCATTC 2280
GCCGGACTCC GGCCCACCTT CGACACCCGG TTGATGCGGC TGGAAGACGA GATGAAAGAG 2340
GGGCGCTACG AGGTACGCGC GGAGCTTCCC GGGGTCGACC CCGACAAGGA CGTCGACATT 2400
ATGGTCCGCG ATGGTCAGCT GACCATCAAG GCCGAGCGCA CCGAGCAGAA GGACTTCGAC 2460
GGTCGCTCGG AATTCGCGTA CGGTTCCTTC GTTCGCACGG TGTCGCTGCC GGTAGGTGCT 2520
GACGAGGACG ACATTAAGGC CACCTACGAC AAGGGCATTC TTACTGTGTC GGTGGCGGTT 2580
TCGGAAGGGA AGCCAACCGA AAAGCACATT CAGATCCGGT CCACCAACTA AGGATCC    2637
```

FIGURE 7

SEQ ID NO:7
Size: 2487
DNA--MTB83F (MTB72F-MTI)

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCATGA CGATTAATTA CCAGTTCGGG 2220
GACGTCGACG CTCATGGCGC CATGATCCGC GCTCAGGCGG CGTCGCTTGA GGCGGAGCAT 2280
CAGGCCATCG TTCGTGATGT GTTGGCCGCG GGTGACTTTT GGGGCGGCGC CGGTTCGGTG 2340
GCTTGCCAGG AGTTCATTAC CCAGTTGGGC CGTAACTTCC AGGTGATCTA CGAGCAGGCC 2400
AACGCCCACG GGCAGAAGGT GCAGGCTGCC GGCAACAACA TGGCGCAAAC CGACAGCGCC 2460
GTCGGCTCCA GCTGGGCCTA AGGATCC                                     2487
```

FIGURE 8

SEQ ID NO:8
Size: 2451
DNA --MTB81F (MTB72F-DPV)

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCGATC CCGTGGACGC GGTCATTAAC 2220
ACCACCTGCA ATTACGGGCA GGTAGTAGCT GCGCTCAACG CGACGGATCC GGGGGCTGCC 2280
GCACAGTTCA ACGCCTCACC GGTGGCGCAG TCCTATTTGC GCAATTTCCT CGCCGCACCG 2340
CCACCTCAGC GCGCTGCCAT GGCCGCGCAA TTGCAAGCTG TGCCGGGGGC GGCACAGTAC 2400
ATCGGCCTTG TCGAGTCGGT TGCCGGCTCC TGCAACAACT ATTAAACTAG T          2451
```

FIG 9A

SEQ ID NO:9
Size: 3474
DNA--MTB114F (MTB72FmTCC#2)

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCATGG ATTTCGGGCT TTTACCTCCG 2220
GAAGTGAATT CAAGCCGAAT GTATTCCGGT CCGGGGCCGG AGTCGATGCT AGCCGCCGCG 2280
GCCGCCTGGG ACGGTGTGGC CGCGGAGTTG ACTTCCGCCG CGGTCTCGTA TGGATCGGTG 2340
GTGTCGACGC TGATCGTTGA GCCGTGGATG GGGCCGGCGG CGGCCGCGAT GGCGGCCGCG 2400
GCAACGCCGT ATGTGGGGTG GCTGGCCGCC ACGGCGGCGC TGGCGAAGGA GACGGCCACA 2460
CAGGCGAGGG CAGCGGCGGA AGCGTTTGGG ACGGCGTTCG CGATGACGGT GCCACCATCC 2520
CTCGTCGCGG CCAACCGCAG CCGGTTGATG TCGCTGGTCG CGGCGAACAT TCTGGGGCAA 2580
AACAGTGCGG CGATCGCGGC TACCCAGGCC GAGTATGCCG AAATGTGGGC CCAAGACGCT 2640
GCCGTGATGT ACAGCTATGA GGGGGCATCT GCGGCCGCGT CGGCGTTGCC GCCGTTCACT 2700
CCACCCGTGC AAGGCACCGG CCCGGCCGGG CCCGCGGCCG CAGCCGCGGC GACCCAAGCC 2760
GCCGGTGCGG GCGCCGTTGC GGATGCACAG GCGACACTGG CCCAGCTGCC CCCGGGGATC 2820
CTGAGCGACA TTCTGTCCGC ATTGGCCGCC AACGCTGATC CGCTGACATC GGGACTGTTG 2880
GGGATCGCGT CGACCCTCAA CCCGCAAGTC GGATCCGCTC AGCCGATAGT GATCCCCACC 2940
CCGATAGGGG AATTGGACGT GATCGCGCTC TACATTGCAT CCATCGCGAC CGGCAGCATT 3000
GCGCTCGCGA TCACGAACAC GGCCAGACCC TGGCACATCG GCCTATACGG GAACGCCGGC 3060
GGGCTGGGAC CGACGCAGGG CCATCCACTG AGTTCGGCGA CCGACGAGCC GGAGCCGCAC 3120
TGGGGCCCCT TCGGGGGCGC GGCGCCGGTG TCCGCGGGCG TCGGCCACGC AGCATTAGTC 3180
GGAGCGTTGT CGGTGCCGCA CAGCTGGACC ACGGCCGCCC CGGAGATCCA GCTCGCCGTT 3240
CAGGCAACAC CCACCTTCAG CTCCAGCGCC GGCGCCGACC CGACGGCCCT AAACGGGATG 3300
```

FIG 9B

```
CCGGCAGGCC TGCTCAGCGG GATGGCTTTG GCGAGCCTGG CCGCACGCGG CACGACGGGC 3360
GGTGGCGGCA CCCGTAGCGG CACCAGCACT GACGGCCAAG AGGACGGCCG CAAACCCCCG 3420
GTAGTTGTGA TTAGAGAGCA GCCGCCGCCC GGAAACCCCC CGCGGTAAAC TAGT       3474
```

FIGURE 10

SEQ ID NO:10
Size: 3104
DNA --MTB102FTM2 (MTB72F-hTCC#1TM2)

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCATGA GCAGAGCGTT CATCATCGAT 2220
CCAACGATCA GTGCCATTGA CGGCTTGTAC GACCTTCTGG GGATTGGAAT ACCCAACCAA 2280
GGGGGTATCC TTTACTCCTC ACTAGAGTAC TTCGAAAAAG CCCTGGAGGA GCTGGCAGCA 2340
GCGTTTCCGG GTGATGGCTG GTTAGGTTCG GCCGCGGACA AATACGCCGG CAAAAACCGC 2400
AACCACGTGA ATTTTTTCCA GGAACTGGCA GACCTCGATC GTCAGCTCAT CAGCCTGATC 2460
CACGACCAGG CCAACGCGGT CCAGACGACC CGCGACAAGC TTCTCAACGG CCTGAAAGAG 2520
CTTTGGGACA AGCTCACGGG GTGGGTGACC GGACTGTTCT CTCGAGGGTG GTCGAACCTG 2580
GAGTCCTTCT TTGCGGGCGT CCCCGGCTTG ACCGGCGCGA CCAGCGGCTT GTCGCAAGTG 2640
ACTGGCTTGT TCGGTGCGGC CGGTCTGTCC GCATCGTCGG GCTTGGCTCA CGCGGATAGC 2700
CTGGCGAGCT CAGCCAGCTT GCCCGCCCTG GCCGGCATTG GGGGCGGGTC CGGTTTTGGG 2760
GGCTTGCCGA GCCTGGCTCA GGTCCATGCC GCCTCAACTC GGCAGGCGCT ACGGCCCCGA 2820
GCTGATGGCC CGGTCGGCGC CGCTGCCGAG CAGGTCGGCG GGCAGTCGCA GCTGGTCTCC 2880
GCGCAGGGTT CCCAAGGTAT GGGCGGACCC GTAGGCATGG GCGGCATGCA CCCCTCTTCG 2940
GGGGCGTCGA AAGGGACGAC GACGAAGAAG TACTCGGAAG GCGCGGCGGC GGGCACTGAA 3000
GACGCCGAGC GCGCGCCAGT CGAAGCTGAC GCGGGCGGTG GGCAAAAGGT GCTGGTACGA 3060
AACGTCGTCT AAACTAGTAA CGGCCGCCAG TGAAGCTGGA ATTC                 3104
```

FIGURE 11

SEQ ID NO:11
Size: 3060
DNA--MTB103F (MTB72F-85b)

```
CATATGCATC ACCATCACCA TCACACGGCC GCGTCCGATA ACTTCCAGCT GTCCCAGGGT 60
GGGCAGGGAT TCGCCATTCC GATCGGGCAG GCGATGGCGA TCGCGGGCCA GATCCGATCG 120
GGTGGGGGGT CACCCACCGT TCATATCGGG CCTACCGCCT TCCTCGGCTT GGGTGTTGTC 180
GACAACAACG GCAACGGCGC ACGAGTCCAA CGCGTGGTCG GGAGCGCTCC GGCGGCAAGT 240
CTCGGCATCT CCACCGGCGA CGTGATCACC GCGGTCGACG GCGCTCCGAT CAACTCGGCC 300
ACCGCGATGG CGGACGCGCT TAACGGGCAT CATCCCGGTG ACGTCATCTC GGTGACCTGG 360
CAAACCAAGT CGGGCGGCAC GCGTACAGGG AACGTGACAT TGGCCGAGGG ACCCCCGGCC 420
GAATTCATGG TGGATTTCGG GGCGTTACCA CCGGAGATCA ACTCCGCGAG GATGTACGCC 480
GGCCCGGGTT CGGCCTCGCT GGTGGCCGCG GCTCAGATGT GGGACAGCGT GGCGAGTGAC 540
CTGTTTTCGG CCGCGTCGGC GTTTCAGTCG GTGGTCTGGG GTCTGACGGT GGGGTCGTGG 600
ATAGGTTCGT CGGCGGGTCT GATGGTGGCG GCGGCCTCGC CGTATGTGGC GTGGATGAGC 660
GTCACCGCGG GGCAGGCCGA GCTGACCGCC GCCCAGGTCC GGGTTGCTGC GGCGGCCTAC 720
GAGACGGCGT ATGGGCTGAC GGTGCCCCCG CCGGTGATCG CCGAGAACCG TGCTGAACTG 780
ATGATTCTGA TAGCGACCAA CCTCTTGGGG CAAAACACCC CGGCGATCGC GGTCAACGAG 840
GCCGAATACG GCGAGATGTG GGCCCAAGAC GCCGCCGCGA TGTTTGGCTA CGCCGCGGCG 900
ACGGCGACGG CGACGGCGAC GTTGCTGCCG TTCGAGGAGG CGCCGGAGAT GACCAGCGCG 960
GGTGGGCTCC TCGAGCAGGC CGCCGCGGTC GAGGAGGCCT CCGACACCGC CGCGGCGAAC 1020
CAGTTGATGA ACAATGTGCC CCAGGCGCTG CAACAGCTGG CCCAGCCCAC GCAGGGCACC 1080
ACGCCTTCTT CCAAGCTGGG TGGCCTGTGG AAGACGGTCT CGCCGCATCG GTCGCCGATC 1140
AGCAACATGG TGTCGATGGC CAACAACCAC ATGTCGATGA CCAACTCGGG TGTGTCGATG 1200
ACCAACACCT TGAGCTCGAT GTTGAAGGGC TTTGCTCCGG CGGCGGCCGC CCAGGCCGTG 1260
CAAACCGCGG CGCAAAACGG GGTCCGGGCG ATGAGCTCGC TGGGCAGCTC GCTGGGTTCT 1320
TCGGGTCTGG GCGGTGGGGT GGCCGCCAAC TTGGGTCGGG CGGCCTCGGT CGGTTCGTTG 1380
TCGGTGCCGC AGGCCTGGGC CGCGGCCAAC CAGGCAGTCA CCCCGGCGGC GCGGGCGCTG 1440
CCGCTGACCA GCCTGACCAG CGCCGCGGAA AGAGGGCCCG GGCAGATGCT GGGCGGGCTG 1500
CCGGTGGGGC AGATGGGCGC CAGGGCCGGT GGTGGGCTCA GTGGTGTGCT GCGTGTTCCG 1560
CCGCGACCCT ATGTGATGCC GCATTCTCCG GCAGCCGGCG ATATCGCCCC GCCGGCCTTG 1620
TCGCAGGACC GGTTCGCCGA CTTCCCCGCG CTGCCCCTCG ACCCGTCCGC GATGGTCGCC 1680
CAAGTGGGGC CACAGGTGGT CAACATCAAC ACCAAACTGG GCTACAACAA CGCCGTGGGC 1740
GCCGGGACCG GCATCGTCAT CGATCCCAAC GGTGTCGTGC TGACCAACAA CCACGTGATC 1800
GCGGGCGCCA CCGACATCAA TGCGTTCAGC GTCGGCTCCG GCCAAACCTA CGGCGTCGAT 1860
GTGGTCGGGT ATGACCGCAC CCAGGATGTC GCGGTGCTGC AGCTGCGCGG TGCCGGTGGC 1920
CTGCCGTCGG CGGCGATCGG TGGCGGCGTC GCGGTTGGTG AGCCCGTCGT CGCGATGGGC 1980
AACAGCGGTG GGCAGGGCGG AACGCCCCGT GCGGTGCCTG GCAGGGTGGT CGCGCTCGGC 2040
CAAACCGTGC AGGCGTCGGA TTCGCTGACC GGTGCCGAAG AGACATTGAA CGGGTTGATC 2100
CAGTTCGATG CCGCGATCCA GCCCGGTGAT TCGGGCGGGC CCGTCGTCAA CGGCCTAGGA 2160
CAGGTGGTCG GTATGAACAC GGCCGCGTCC GGTACCTTCT CCCGGCCGGG GCTGCCGGTC 2220
GAGTACCTGC AGGTGCCGTC GCCGTCGATG GGCCGCGACA TCAAGGTTCA GTTCCAGAGC 2280
GGTGGGAACA ACTCACCTGC GGTTTATCTG CTCGACGGCC TGCGCGCCCA AGACGACTAC 2340
AACGGCTGGG ATATCAACAC CCCGGCGTTC GAGTGGTACT ACCAGTCGGG ACTGTCGATA 2400
GTCATGCCGG TCGGCGGGCA GTCCAGCTTC TACAGCGACT GGTACAGCCC GGCCTGCGGT 2460
AAGGCTGGCT GCCAGACTTA CAAGTGGGAA ACCTTCCTGA CCAGCGAGCT GCCGCAATGG 2520
TTGTCCGCCA ACAGGGCCGT GAAGCCCACC GGCAGCGCTG CAATCGGCTT GTCGATGGCC 2580
GGCTCGTCGG CAATGATCTT GGCCGCCTAC CATCCCCAGC AGTTCATCTA CGCCGGCTCG 2640
CTGTCGGCCC TGCTGGACCC CTCTCAGGGG ATGGGGCCTA GCCTGATCGG CCTCGCGATG 2700
GGTGACGCCG GCGGTTACAA GGCCGCAGAC ATGTGGGGTC CCTCGAGTGA CCCGGCATGG 2760
GAGCGCAACG ACCCTACGCA GCAGATCCCC AAGCTGGTCG CAAACAACAC CCGGCTATGG 2820
GTTTATTGCG GGAACGGCAC CCCGAACGAG TTGGGCGGTG CCAACATACC CGCCGAGTTC 2880
TTGGAGAACT TCGTTCGTAG CAGCAACCTG AAGTTCCAGG ATGCGTACAA CGCCGCGGGC 2940
GGGCACAACG CCGTGTTCAA CTTCCCGCCC AACGGCACGC ACAGCTGGGA GTACTGGGGC 3000
GCTCAGCTCA ACGCCATGAA GGGTGACCTG CAGAGTTCGT TAGGCGCCGG CTGAGGATCC 3060
```

FIG 12A

SEQ ID NO:12
Size: 930
PRT --r95F (MTB72F-MAPS)

```
Met His His His His His His Thr Ala Ala Ser Asp Asn Phe Gln Leu
                    5                  10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ala Ser Leu
65                  70                  75                      80

Gly Ile Ser Thr Gly Asp Val Ile Thr Ala Val Asp Gly Ala Pro Ile
                    85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                     160

Pro Gly Ser Ala Ser Leu Val Ala Ala Ala Gln Met Trp Asp Ser Val
                165                 170                     175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                     240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
```

FIG 12B 290 295 300

Ala Thr Leu Leu Pro Phe Glu Glu Ala Pro Glu Met Thr Ser Ala Gly
305 310 315 320

Gly Leu Leu Glu Gln Ala Ala Ala Val Glu Glu Ala Ser Asp Thr Ala
325 330 335

Ala Ala Asn Gln Leu Met Asn Asn Val Pro Gln Ala Leu Gln Gln Leu
340 345 350

Ala Gln Pro Thr Gln Gly Thr Thr Pro Ser Ser Lys Leu Gly Gly Leu
355 360 365

Trp Lys Thr Val Ser Pro His Arg Ser Pro Ile Ser Asn Met Val Ser
370 375 380

Met Ala Asn Asn His Met Ser Met Thr Asn Ser Gly Val Ser Met Thr
385 390 395 400

Asn Thr Leu Ser Ser Met Leu Lys Gly Phe Ala Pro Ala Ala Ala Ala
405 410 415

Gln Ala Val Gln Thr Ala Ala Gln Asn Gly Val Arg Ala Met Ser Ser
420 425 430

Leu Gly Ser Ser Leu Gly Ser Ser Gly Leu Gly Gly Gly Val Ala Ala
435 440 445

Asn Leu Gly Arg Ala Ala Ser Val Gly Ser Leu Ser Val Pro Gln Ala
450 455 460

Trp Ala Ala Ala Asn Gln Ala Val Thr Pro Ala Ala Arg Ala Leu Pro
465 470 475 480

Leu Thr Ser Leu Thr Ser Ala Ala Glu Arg Gly Pro Gly Gln Met Leu
485 490 495

Gly Gly Leu Pro Val Gly Gln Met Gly Ala Arg Ala Gly Gly Gly Leu
500 505 510

Ser Gly Val Leu Arg Val Pro Pro Arg Pro Tyr Val Met Pro His Ser
515 520 525

Pro Ala Ala Gly Asp Ile Ala Pro Pro Ala Leu Ser Gln Asp Arg Phe
530 535 540

Ala Asp Phe Pro Ala Leu Pro Leu Asp Pro Ser Ala Met Val Ala Gln
545 550 555 560

Val Gly Pro Gln Val Val Asn Ile Asn Thr Lys Leu Gly Tyr Asn Asn
565 570 575

Ala Val Gly Ala Gly Thr Gly Ile Val Ile Asp Pro Asn Gly Val Val
580 585 590

Leu Thr Asn Asn His Val Ile Ala Gly Ala Thr Asp Ile Asn Ala Phe
595 600 605

Ser Val Gly Ser Gly Gln Thr Tyr Gly Val Asp Val Val Gly Tyr Asp
610 615 620

FIG 12C

Arg Thr Gln Asp Val Ala Val Leu Gln Leu Arg Gly Ala Gly Gly Leu
625 630 635 640

Pro Ser Ala Ala Ile Gly Gly Gly Val Ala Val Gly Glu Pro Val Val
645 650 655

Ala Met Gly Asn Ser Gly Gly Gln Gly Gly Thr Pro Arg Ala Val Pro
660 665 670

Gly Arg Val Val Ala Leu Gly Gln Thr Val Gln Ala Ser Asp Ser Leu
675 680 685

Thr Gly Ala Glu Glu Thr Leu Asn Gly Leu Ile Gln Phe Asp Ala Ala
690 695 700

Ile Gln Pro Gly Asp Ser Gly Gly Pro Val Val Asn Gly Leu Gly Gln
705 710 715 720

Val Val Gly Met Asn Thr Ala Ala Ser Gly Thr Met Ser Cys Gly Asn
725 730 735

Ala Lys Ile Asn Ser Pro Ala Pro Ser Phe Glu Glu Val Ala Leu Met
740 745 750

Pro Asn Gly Ser Phe Lys Lys Ile Ser Leu Ser Ser Tyr Lys Gly Lys
755 760 765

Trp Val Val Leu Phe Phe Tyr Pro Leu Asp Phe Thr Phe Val Cys Pro
770 775 780

Thr Glu Val Ile Ala Phe Ser Asp Ser Val Ser Arg Phe Asn Glu Leu
785 790 795 800

Asn Cys Glu Val Leu Ala Cys Ser Ile Asp Ser Glu Tyr Ala His Leu
805 810 815

Gln Trp Thr Leu Gln Asp Arg Lys Lys Gly Gly Leu Gly Thr Met Ala
820 825 830

Ile Pro Met Leu Ala Asp Lys Thr Lys Ser Ile Ala Arg Ser Tyr Gly
835 840 845

Val Leu Glu Glu Ser Gln Gly Val Ala Tyr Arg Gly Leu Phe Ile Ile
850 855 860

Asp Pro His Gly Met Leu Arg Gln Ile Thr Val Asn Asp Met Pro Val
865 870 875 880

Gly Arg Ser Val Glu Glu Val Leu Arg Leu Leu Glu Ala Phe Gln Phe
885 890 895

Val Glu Lys His Gly Glu Val Cys Pro Ala Asn Trp Lys Lys Gly Ala
900 905 910

Pro Thr Met Lys Pro Glu Pro Asn Ala Ser Val Glu Gly Tyr Phe Ser
915 920 925

Lys Gln
930

FIG 13A

SEQ ID NO:13
Size: 875
PRT--MTB89F (MTB72F-Erd14)

```
Met His His His His His His Thr Ala Ala Ser Asp Asn Phe Gln Leu
                    5                  10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
```

```
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620
```

FIG 13C

```
Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Ala Thr Thr Leu
                725                 730                 735

Pro Val Gln Arg His Pro Arg Ser Leu Phe Pro Glu Phe Ser Glu Leu
            740                 745                 750

Phe Ala Ala Phe Pro Ser Phe Ala Gly Leu Arg Pro Thr Phe Asp Thr
        755                 760                 765

Arg Leu Met Arg Leu Glu Asp Glu Met Lys Glu Gly Arg Tyr Glu Val
    770                 775                 780

Arg Ala Glu Leu Pro Gly Val Asp Pro Asp Lys Asp Val Asp Ile Met
785                 790                 795                 800

Val Arg Asp Gly Gln Leu Thr Ile Lys Ala Glu Arg Thr Glu Gln Lys
                805                 810                 815

Asp Phe Asp Gly Arg Ser Glu Phe Ala Tyr Gly Ser Phe Val Arg Thr
            820                 825                 830

Val Ser Leu Pro Val Gly Ala Asp Glu Asp Asp Ile Lys Ala Thr Tyr
        835                 840                 845

Asp Lys Gly Ile Leu Thr Val Ser Val Ala Val Ser Glu Gly Lys Pro
    850                 855                 860

Thr Glu Lys His Ile Gln Ile Arg Ser Thr Asn
865                 870                 875
```

FIG 14A

SEQ ID NO:14
Size: 825
PRT--MTB83F (MTB72F-MTI)

Met His His His His His His Thr Ala Ala Ser Asp Asn Phe Gln Leu
5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

Asp Val Ile Ser Val Thr Trp Gln Thr Lys Ser Gly Gly Thr Arg Thr
115 120 125

Gly Asn Val Thr Leu Ala Glu Gly Pro Pro Ala Glu Phe Met Val Asp
130 135 140

Phe Gly Ala Leu Pro Pro Glu Ile Asn Ser Ala Arg Met Tyr Ala Gly
145 150 155 160

Pro Gly Ser Ala Ser Leu Val Ala Ala Ala Gln Met Trp Asp Ser Val
165 170 175

Ala Ser Asp Leu Phe Ser Ala Ala Ser Ala Phe Gln Ser Val Val Trp
180 185 190

Gly Leu Thr Val Gly Ser Trp Ile Gly Ser Ser Ala Gly Leu Met Val
195 200 205

Ala Ala Ala Ser Pro Tyr Val Ala Trp Met Ser Val Thr Ala Gly Gln
210 215 220

Ala Glu Leu Thr Ala Ala Gln Val Arg Val Ala Ala Ala Ala Tyr Glu
225 230 235 240

Thr Ala Tyr Gly Leu Thr Val Pro Pro Pro Val Ile Ala Glu Asn Arg
245 250 255

Ala Glu Leu Met Ile Leu Ile Ala Thr Asn Leu Leu Gly Gln Asn Thr
260 265 270

Pro Ala Ile Ala Val Asn Glu Ala Glu Tyr Gly Glu Met Trp Ala Gln
275 280 285

Asp Ala Ala Ala Met Phe Gly Tyr Ala Ala Ala Thr Ala Thr Ala Thr

FIG 14B

|     | 290 |     |     |     | 295 |     |     |     | 300 |     |     |     |
|-----|-----|-----|-----|-----|-----|-----|-----|-----|-----|-----|-----|-----|

Ala Thr Leu Leu Pro Phe Glu Glu Ala Pro Glu Met Thr Ser Ala Gly
305             310             315             320

Gly Leu Leu Glu Gln Ala Ala Ala Val Glu Glu Ala Ser Asp Thr Ala
                325             330             335

Ala Ala Asn Gln Leu Met Asn Asn Val Pro Gln Ala Leu Gln Gln Leu
            340             345             350

Ala Gln Pro Thr Gln Gly Thr Thr Pro Ser Ser Lys Leu Gly Gly Leu
        355             360             365

Trp Lys Thr Val Ser Pro His Arg Ser Pro Ile Ser Asn Met Val Ser
370             375             380

Met Ala Asn Asn His Met Ser Met Thr Asn Ser Gly Val Ser Met Thr
385             390             395             400

Asn Thr Leu Ser Ser Met Leu Lys Gly Phe Ala Pro Ala Ala Ala Ala
            405             410             415

Gln Ala Val Gln Thr Ala Ala Gln Asn Gly Val Arg Ala Met Ser Ser
        420             425             430

Leu Gly Ser Ser Leu Gly Ser Ser Gly Leu Gly Gly Gly Val Ala Ala
        435             440             445

Asn Leu Gly Arg Ala Ala Ser Val Gly Ser Leu Ser Val Pro Gln Ala
450             455             460

Trp Ala Ala Ala Asn Gln Ala Val Thr Pro Ala Ala Arg Ala Leu Pro
465             470             475             480

Leu Thr Ser Leu Thr Ser Ala Ala Glu Arg Gly Pro Gly Gln Met Leu
            485             490             495

Gly Gly Leu Pro Val Gly Gln Met Gly Ala Arg Ala Gly Gly Gly Leu
        500             505             510

Ser Gly Val Leu Arg Val Pro Pro Arg Pro Tyr Val Met Pro His Ser
        515             520             525

Pro Ala Ala Gly Asp Ile Ala Pro Pro Ala Leu Ser Gln Asp Arg Phe
530             535             540

Ala Asp Phe Pro Ala Leu Pro Leu Asp Pro Ser Ala Met Val Ala Gln
545             550             555             560

Val Gly Pro Gln Val Val Asn Ile Asn Thr Lys Leu Gly Tyr Asn Asn
            565             570             575

Ala Val Gly Ala Gly Thr Gly Ile Val Ile Asp Pro Asn Gly Val Val
        580             585             590

Leu Thr Asn Asn His Val Ile Ala Gly Ala Thr Asp Ile Asn Ala Phe
        595             600             605

Ser Val Gly Ser Gly Gln Thr Tyr Gly Val Asp Val Val Gly Tyr Asp
610             615             620

FIG 14C

Arg Thr Gln Asp Val Ala Val Leu Gln Leu Arg Gly Ala Gly Gly Leu
625 630 635 640

Pro Ser Ala Ala Ile Gly Gly Gly Val Ala Val Gly Glu Pro Val Val
645 650 655

Ala Met Gly Asn Ser Gly Gly Gln Gly Gly Thr Pro Arg Ala Val Pro
660 665 670

Gly Arg Val Val Ala Leu Gly Gln Thr Val Gln Ala Ser Asp Ser Leu
675 680 685

Thr Gly Ala Glu Glu Thr Leu Asn Gly Leu Ile Gln Phe Asp Ala Ala
690 695 700

Ile Gln Pro Gly Asp Ser Gly Gly Pro Val Val Asn Gly Leu Gly Gln
705 710 715 720

Val Val Gly Met Asn Thr Ala Ala Ser Gly Thr Met Thr Ile Asn Tyr
725 730 735

Gln Phe Gly Asp Val Asp Ala His Gly Ala Met Ile Arg Ala Gln Ala
740 745 750

Ala Ser Leu Glu Ala Glu His Gln Ala Ile Val Arg Asp Val Leu Ala
755 760 765

Ala Gly Asp Phe Trp Gly Gly Ala Gly Ser Val Ala Cys Gln Glu Phe
770 775 780

Ile Thr Gln Leu Gly Arg Asn Phe Gln Val Ile Tyr Glu Gln Ala Asn
785 790 795 800

Ala His Gly Gln Lys Val Gln Ala Ala Gly Asn Asn Met Ala Gln Thr
805 810 815

Asp Ser Ala Val Gly Ser Ser Trp Ala
820 825

FIG 15A

SEQ ID NO:15
Size: 813
PRT--MTB81F (MTB72F-DPV)

```
Met His His His His His His Thr Ala Ala Ser Asp Asn Phe Gln Leu
                    5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Gly Ser Pro Thr Val His Ile
         35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
```

FIG 15B

```
              290                       295                      300
   Ala Thr Leu Leu Pro Phe Glu Glu Ala Pro Glu Met Thr Ser Ala Gly
   305                 310                 315                 320

   Gly Leu Leu Glu Gln Ala Ala Ala Val Glu Glu Ala Ser Asp Thr Ala
                   325                 330                 335

   Ala Ala Asn Gln Leu Met Asn Asn Val Pro Gln Ala Leu Gln Gln Leu
                   340                 345                 350

   Ala Gln Pro Thr Gln Gly Thr Thr Pro Ser Ser Lys Leu Gly Gly Leu
               355                 360                 365

   Trp Lys Thr Val Ser Pro His Arg Ser Pro Ile Ser Asn Met Val Ser
   370                 375                 380

   Met Ala Asn Asn His Met Ser Met Thr Asn Ser Gly Val Ser Met Thr
   385                 390                 395                 400

   Asn Thr Leu Ser Ser Met Leu Lys Gly Phe Ala Pro Ala Ala Ala Ala
                   405                 410                 415

   Gln Ala Val Gln Thr Ala Ala Gln Asn Gly Val Arg Ala Met Ser Ser
                   420                 425                 430

   Leu Gly Ser Ser Leu Gly Ser Ser Gly Leu Gly Gly Gly Val Ala Ala
                   435                 440                 445

   Asn Leu Gly Arg Ala Ala Ser Val Gly Ser Leu Ser Val Pro Gln Ala
   450                 455                 460

   Trp Ala Ala Ala Asn Gln Ala Val Thr Pro Ala Ala Arg Ala Leu Pro
   465                 470                 475                 480

   Leu Thr Ser Leu Thr Ser Ala Ala Glu Arg Gly Pro Gly Gln Met Leu
                   485                 490                 495

   Gly Gly Leu Pro Val Gly Gln Met Gly Ala Arg Ala Gly Gly Gly Leu
                   500                 505                 510

   Ser Gly Val Leu Arg Val Pro Pro Arg Pro Tyr Val Met Pro His Ser
                   515                 520                 525

   Pro Ala Ala Gly Asp Ile Ala Pro Pro Ala Leu Ser Gln Asp Arg Phe
   530                 535                 540

   Ala Asp Phe Pro Ala Leu Pro Leu Asp Pro Ser Ala Met Val Ala Gln
   545                 550                 555                 560

   Val Gly Pro Gln Val Val Asn Ile Asn Thr Lys Leu Gly Tyr Asn Asn
                   565                 570                 575

   Ala Val Gly Ala Gly Thr Gly Ile Val Ile Asp Pro Asn Gly Val Val
                   580                 585                 590

   Leu Thr Asn Asn His Val Ile Ala Gly Ala Thr Asp Ile Asn Ala Phe
                   595                 600                 605

   Ser Val Gly Ser Gly Gln Thr Tyr Gly Val Asp Val Val Gly Tyr Asp
   610                 615                 620
```

FIG 15C

```
Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Asp Pro Val Asp Ala
                725                 730                 735

Val Ile Asn Thr Thr Cys Asn Tyr Gly Gln Val Val Ala Ala Leu Asn
            740                 745                 750

Ala Thr Asp Pro Gly Ala Ala Ala Gln Phe Asn Ala Ser Pro Val Ala
        755                 760                 765

Gln Ser Tyr Leu Arg Asn Phe Leu Ala Ala Pro Pro Pro Gln Arg Ala
    770                 775                 780

Ala Met Ala Ala Gln Leu Gln Ala Val Pro Gly Ala Ala Gln Tyr Ile
785                 790                 795                 800

Gly Leu Val Glu Ser Val Ala Gly Ser Cys Asn Asn Tyr
                805                 810
```

FIG 16A

SEQ ID NO:16
Size: 1154
PRT--MTB114F (MTB72F-mTCC )

Met His His His His His His Thr Ala Ala Ser Asp Asn Phe Gln Leu
5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

Asp Val Ile Ser Val Thr Trp Gln Thr Lys Ser Gly Gly Thr Arg Thr
115 120 125

Gly Asn Val Thr Leu Ala Glu Gly Pro Pro Ala Glu Phe Met Val Asp
130 135 140

Phe Gly Ala Leu Pro Pro Glu Ile Asn Ser Ala Arg Met Tyr Ala Gly
145 150 155 160

Pro Gly Ser Ala Ser Leu Val Ala Ala Ala Gln Met Trp Asp Ser Val
165 170 175

Ala Ser Asp Leu Phe Ser Ala Ala Ser Ala Phe Gln Ser Val Val Trp
180 185 190

Gly Leu Thr Val Gly Ser Trp Ile Gly Ser Ser Ala Gly Leu Met Val
195 200 205

Ala Ala Ala Ser Pro Tyr Val Ala Trp Met Ser Val Thr Ala Gly Gln
210 215 220

Ala Glu Leu Thr Ala Ala Gln Val Arg Val Ala Ala Ala Ala Tyr Glu
225 230 235 240

Thr Ala Tyr Gly Leu Thr Val Pro Pro Pro Val Ile Ala Glu Asn Arg
245 250 255

Ala Glu Leu Met Ile Leu Ile Ala Thr Asn Leu Leu Gly Gln Asn Thr
260 265 270

Pro Ala Ile Ala Val Asn Glu Ala Glu Tyr Gly Glu Met Trp Ala Gln
275 280 285

Asp Ala Ala Ala Met Phe Gly Tyr Ala Ala Ala Thr Ala Thr Ala Thr

FIG 16B 290 295 300

Ala Thr Leu Leu Pro Phe Glu Glu Ala Pro Glu Met Thr Ser Ala Gly
305 310 315 320

Gly Leu Leu Glu Gln Ala Ala Ala Val Glu Glu Ala Ser Asp Thr Ala
325 330 335

Ala Ala Asn Gln Leu Met Asn Asn Val Pro Gln Ala Leu Gln Gln Leu
340 345 350

Ala Gln Pro Thr Gln Gly Thr Thr Pro Ser Ser Lys Leu Gly Gly Leu
355 360 365

Trp Lys Thr Val Ser Pro His Arg Ser Pro Ile Ser Asn Met Val Ser
370 375 380

Met Ala Asn Asn His Met Ser Met Thr Asn Ser Gly Val Ser Met Thr
385 390 395 400

Asn Thr Leu Ser Ser Met Leu Lys Gly Phe Ala Pro Ala Ala Ala Ala
405 410 415

Gln Ala Val Gln Thr Ala Ala Gln Asn Gly Val Arg Ala Met Ser Ser
420 425 430

Leu Gly Ser Ser Leu Gly Ser Ser Gly Leu Gly Gly Gly Val Ala Ala
435 440 445

Asn Leu Gly Arg Ala Ala Ser Val Gly Ser Leu Ser Val Pro Gln Ala
450 455 460

Trp Ala Ala Ala Asn Gln Ala Val Thr Pro Ala Ala Arg Ala Leu Pro
465 470 475 480

Leu Thr Ser Leu Thr Ser Ala Ala Glu Arg Gly Pro Gly Gln Met Leu
485 490 495

Gly Gly Leu Pro Val Gly Gln Met Gly Ala Arg Ala Gly Gly Gly Leu
500 505 510

Ser Gly Val Leu Arg Val Pro Pro Arg Pro Tyr Val Met Pro His Ser
515 520 525

Pro Ala Ala Gly Asp Ile Ala Pro Pro Ala Leu Ser Gln Asp Arg Phe
530 535 540

Ala Asp Phe Pro Ala Leu Pro Leu Asp Pro Ser Ala Met Val Ala Gln
545 550 555 560

Val Gly Pro Gln Val Val Asn Ile Asn Thr Lys Leu Gly Tyr Asn Asn
565 570 575

Ala Val Gly Ala Gly Thr Gly Ile Val Ile Asp Pro Asn Gly Val Val
580 585 590

Leu Thr Asn Asn His Val Ile Ala Gly Ala Thr Asp Ile Asn Ala Phe
595 600 605

Ser Val Gly Ser Gly Gln Thr Tyr Gly Val Asp Val Val Gly Tyr Asp
610 615 620

FIG 16C

Arg Thr Gln Asp Val Ala Val Leu Gln Leu Arg Gly Ala Gly Gly Leu
625 630 635 640

Pro Ser Ala Ala Ile Gly Gly Gly Val Ala Val Gly Glu Pro Val Val
645 650 655

Ala Met Gly Asn Ser Gly Gly Gln Gly Gly Thr Pro Arg Ala Val Pro
660 665 670

Gly Arg Val Val Ala Leu Gly Gln Thr Val Gln Ala Ser Asp Ser Leu
675 680 685

Thr Gly Ala Glu Glu Thr Leu Asn Gly Leu Ile Gln Phe Asp Ala Ala
690 695 700

Ile Gln Pro Gly Asp Ser Gly Gly Pro Val Val Asn Gly Leu Gly Gln
705 710 715 720

Val Val Gly Met Asn Thr Ala Ala Ser Gly Thr Met Asp Phe Gly Leu
725 730 735

Leu Pro Pro Glu Val Asn Ser Ser Arg Met Tyr Ser Gly Pro Gly Pro
740 745 750

Glu Ser Met Leu Ala Ala Ala Ala Ala Trp Asp Gly Val Ala Ala Glu
755 760 765

Leu Thr Ser Ala Ala Val Ser Tyr Gly Ser Val Val Ser Thr Leu Ile
770 775 780

Val Glu Pro Trp Met Gly Pro Ala Ala Ala Ala Met Ala Ala Ala Ala
785 790 795 800

Thr Pro Tyr Val Gly Trp Leu Ala Ala Thr Ala Ala Leu Ala Lys Glu
805 810 815

Thr Ala Thr Gln Ala Arg Ala Ala Ala Glu Ala Phe Gly Thr Ala Phe
820 825 830

Ala Met Thr Val Pro Pro Ser Leu Val Ala Ala Asn Arg Ser Arg Leu
835 840 845

Met Ser Leu Val Ala Ala Asn Ile Leu Gly Gln Asn Ser Ala Ala Ile
850 855 860

Ala Ala Thr Gln Ala Glu Tyr Ala Glu Met Trp Ala Gln Asp Ala Ala
865 870 875 880

Val Met Tyr Ser Tyr Glu Gly Ala Ser Ala Ala Ala Ser Ala Leu Pro
885 890 895

Pro Phe Thr Pro Pro Val Gln Gly Thr Gly Pro Ala Gly Pro Ala Ala
900 905 910

Ala Ala Ala Ala Thr Gln Ala Ala Gly Ala Gly Ala Val Ala Asp Ala
915 920 925

Gln Ala Thr Leu Ala Gln Leu Pro Pro Gly Ile Leu Ser Asp Ile Leu
930 935 940

FIG 16D

Ser Ala Leu Ala Ala Asn Ala Asp Pro Leu Thr Ser Gly Leu Leu Gly
945 950 955 960

Ile Ala Ser Thr Leu Asn Pro Gln Val Gly Ser Ala Gln Pro Ile Val
965 970 975

Ile Pro Thr Pro Ile Gly Glu Leu Asp Val Ile Ala Leu Tyr Ile Ala
980 985 990

Ser Ile Ala Thr Gly Ser Ile Ala Leu Ala Ile Thr Asn Thr Ala Arg
995 1000 1005

Pro Trp His Ile Gly Leu Tyr Gly Asn Ala Gly Gly Leu Gly Pro Thr
1010 1015 1020

Gln Gly His Pro Leu Ser Ser Ala Thr Asp Glu Pro Glu Pro His Trp
1025 1030 1035 1040

Gly Pro Phe Gly Gly Ala Ala Pro Val Ser Ala Gly Val Gly His Ala
1045 1050 1055

Ala Leu Val Gly Ala Leu Ser Val Pro His Ser Trp Thr Thr Ala Ala
1060 1065 1070

Pro Glu Ile Gln Leu Ala Val Gln Ala Thr Pro Thr Phe Ser Ser Ser
1075 1080 1085

Ala Gly Ala Asp Pro Thr Ala Leu Asn Gly Met Pro Ala Gly Leu Leu
1090 1095 1100

Ser Gly Met Ala Leu Ala Ser Leu Ala Ala Arg Gly Thr Thr Gly Gly
1105 1110 1115 1120

Gly Gly Thr Arg Ser Gly Thr Ser Thr Asp Gly Gln Glu Asp Gly Arg
1125 1130 1135

Lys Pro Pro Val Val Val Ile Arg Glu Gln Pro Pro Pro Gly Asn Pro
1140 1145 1150

Pro Arg

FIG 17A

SEQ ID NO:17
Size: 1022
PRT- MTB102tm2F ( MTB72F-hTCC#1 )

Met His His His His His His Thr Ala Ala Ser Asp Asn Phe Gln Leu
5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

Asp Val Ile Ser Val Thr Trp Gln Thr Lys Ser Gly Gly Thr Arg Thr
115 120 125

Gly Asn Val Thr Leu Ala Glu Gly Pro Pro Ala Glu Phe Met Val Asp
130 135 140

Phe Gly Ala Leu Pro Pro Glu Ile Asn Ser Ala Arg Met Tyr Ala Gly
145 150 155 160

Pro Gly Ser Ala Ser Leu Val Ala Ala Ala Gln Met Trp Asp Ser Val
165 170 175

Ala Ser Asp Leu Phe Ser Ala Ala Ser Ala Phe Gln Ser Val Val Trp
180 185 190

Gly Leu Thr Val Gly Ser Trp Ile Gly Ser Ser Ala Gly Leu Met Val
195 200 205

Ala Ala Ala Ser Pro Tyr Val Ala Trp Met Ser Val Thr Ala Gly Gln
210 215 220

Ala Glu Leu Thr Ala Ala Gln Val Arg Val Ala Ala Ala Ala Tyr Glu
225 230 235 240

Thr Ala Tyr Gly Leu Thr Val Pro Pro Pro Val Ile Ala Glu Asn Arg
245 250 255

Ala Glu Leu Met Ile Leu Ile Ala Thr Asn Leu Leu Gly Gln Asn Thr
260 265 270

Pro Ala Ile Ala Val Asn Glu Ala Glu Tyr Gly Glu Met Trp Ala Gln
275 280 285

Asp Ala Ala Ala Met Phe Gly Tyr Ala Ala Ala Thr Ala Thr Ala Thr

FIG 17B 290 295 300

Ala Thr Leu Leu Pro Phe Glu Glu Ala Pro Glu Met Thr Ser Ala Gly
305 310 315 320

Gly Leu Leu Glu Gln Ala Ala Ala Val Glu Glu Ala Ser Asp Thr Ala
325 330 335

Ala Ala Asn Gln Leu Met Asn Asn Val Pro Gln Ala Leu Gln Gln Leu
340 345 350

Ala Gln Pro Thr Gln Gly Thr Thr Pro Ser Ser Lys Leu Gly Gly Leu
355 360 365

Trp Lys Thr Val Ser Pro His Arg Ser Pro Ile Ser Asn Met Val Ser
370 375 380

Met Ala Asn Asn His Met Ser Met Thr Asn Ser Gly Val Ser Met Thr
385 390 395 400

Asn Thr Leu Ser Ser Met Leu Lys Gly Phe Ala Pro Ala Ala Ala Ala
405 410 415

Gln Ala Val Gln Thr Ala Ala Gln Asn Gly Val Arg Ala Met Ser Ser
420 425 430

Leu Gly Ser Ser Leu Gly Ser Ser Gly Leu Gly Gly Gly Val Ala Ala
435 440 445

Asn Leu Gly Arg Ala Ala Ser Val Gly Ser Leu Ser Val Pro Gln Ala
450 455 460

Trp Ala Ala Ala Asn Gln Ala Val Thr Pro Ala Ala Arg Ala Leu Pro
465 470 475 480

Leu Thr Ser Leu Thr Ser Ala Ala Glu Arg Gly Pro Gly Gln Met Leu
485 490 495

Gly Gly Leu Pro Val Gly Gln Met Gly Ala Arg Ala Gly Gly Gly Leu
500 505 510

Ser Gly Val Leu Arg Val Pro Pro Arg Pro Tyr Val Met Pro His Ser
515 520 525

Pro Ala Ala Gly Asp Ile Ala Pro Pro Ala Leu Ser Gln Asp Arg Phe
530 535 540

Ala Asp Phe Pro Ala Leu Pro Leu Asp Pro Ser Ala Met Val Ala Gln
545 550 555 560

Val Gly Pro Gln Val Val Asn Ile Asn Thr Lys Leu Gly Tyr Asn Asn
565 570 575

Ala Val Gly Ala Gly Thr Gly Ile Val Ile Asp Pro Asn Gly Val Val
580 585 590

Leu Thr Asn Asn His Val Ile Ala Gly Ala Thr Asp Ile Asn Ala Phe
595 600 605

Ser Val Gly Ser Gly Gln Thr Tyr Gly Val Asp Val Val Gly Tyr Asp
610 615 620

FIG 17C

```
Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Ser Arg Ala Phe
                725                 730                 735

Ile Ile Asp Pro Thr Ile Ser Ala Ile Asp Gly Leu Tyr Asp Leu Leu
            740                 745                 750

Gly Ile Gly Ile Pro Asn Gln Gly Gly Ile Leu Tyr Ser Ser Leu Glu
        755                 760                 765

Tyr Phe Glu Lys Ala Leu Glu Glu Leu Ala Ala Ala Phe Pro Gly Asp
    770                 775                 780

Gly Trp Leu Gly Ser Ala Ala Asp Lys Tyr Ala Gly Lys Asn Arg Asn
785                 790                 795                 800

His Val Asn Phe Phe Gln Glu Leu Ala Asp Leu Asp Arg Gln Leu Ile
                805                 810                 815

Ser Leu Ile His Asp Gln Ala Asn Ala Val Gln Thr Thr Arg Asp Lys
            820                 825                 830

Leu Leu Asn Gly Leu Lys Glu Leu Trp Asp Lys Leu Thr Gly Trp Val
        835                 840                 845

Thr Gly Leu Phe Ser Arg Gly Trp Ser Asn Leu Glu Ser Phe Phe Ala
    850                 855                 860

Gly Val Pro Gly Leu Thr Gly Ala Thr Ser Gly Leu Ser Gln Val Thr
865                 870                 875                 880

Gly Leu Phe Gly Ala Ala Gly Leu Ser Ala Ser Ser Gly Leu Ala His
                885                 890                 895

Ala Asp Ser Leu Ala Ser Ser Ala Ser Leu Pro Ala Leu Ala Gly Ile
            900                 905                 910

Gly Gly Gly Ser Gly Phe Gly Gly Leu Pro Ser Leu Ala Gln Val His
        915                 920                 925

Ala Ala Ser Thr Arg Gln Ala Leu Arg Pro Arg Ala Asp Gly Pro Val
    930                 935                 940
```

FIG 17D

```
Gly Ala Ala Ala Glu Gln Val Gly Gly Gln Ser Gln Leu Val Ser Ala
945                 950                 955                 960

Gln Gly Ser Gln Gly Met Gly Gly Pro Val Gly Met Gly Gly Met His
                965                 970                 975

Pro Ser Ser Gly Ala Ser Lys Gly Thr Thr Thr Lys Lys Tyr Ser Glu
            980                 985                 990

Gly Ala Ala Ala Gly Thr Glu Asp Ala Glu Arg Ala Pro Val Glu Ala
        995                 1000                1005

Asp Ala Gly Gly Gly Gln Lys Val Leu Val Arg Asn Val Val
    1010                1015                1020
```

FIG 18A

SEQ ID NO:18
Size: 1016
PRT--MTB103F (MTB72F-85b)

Met His His His His His His Thr Ala Ala Ser Asp Asn Phe Gln Leu
5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

Asp Val Ile Ser Val Thr Trp Gln Thr Lys Ser Gly Gly Thr Arg Thr
115 120 125

Gly Asn Val Thr Leu Ala Glu Gly Pro Pro Ala Glu Phe Met Val Asp
130 135 140

Phe Gly Ala Leu Pro Pro Glu Ile Asn Ser Ala Arg Met Tyr Ala Gly
145 150 155 160

Pro Gly Ser Ala Ser Leu Val Ala Ala Ala Gln Met Trp Asp Ser Val
165 170 175

Ala Ser Asp Leu Phe Ser Ala Ala Ser Ala Phe Gln Ser Val Val Trp
180 185 190

Gly Leu Thr Val Gly Ser Trp Ile Gly Ser Ser Ala Gly Leu Met Val
195 200 205

Ala Ala Ala Ser Pro Tyr Val Ala Trp Met Ser Val Thr Ala Gly Gln
210 215 220

Ala Glu Leu Thr Ala Ala Gln Val Arg Val Ala Ala Ala Ala Tyr Glu
225 230 235 240

Thr Ala Tyr Gly Leu Thr Val Pro Pro Pro Val Ile Ala Glu Asn Arg
245 250 255

Ala Glu Leu Met Ile Leu Ile Ala Thr Asn Leu Leu Gly Gln Asn Thr
260 265 270

Pro Ala Ile Ala Val Asn Glu Ala Glu Tyr Gly Glu Met Trp Ala Gln
275 280 285

Asp Ala Ala Ala Met Phe Gly Tyr Ala Ala Ala Thr Ala Thr Ala Thr

FIG 18B 290 295 300

Ala Thr Leu Leu Pro Phe Glu Glu Ala Pro Glu Met Thr Ser Ala Gly
305 310 315 320

Gly Leu Leu Glu Gln Ala Ala Ala Val Glu Glu Ala Ser Asp Thr Ala
325 330 335

Ala Ala Asn Gln Leu Met Asn Asn Val Pro Gln Ala Leu Gln Gln Leu
340 345 350

Ala Gln Pro Thr Gln Gly Thr Thr Pro Ser Ser Lys Leu Gly Gly Leu
355 360 365

Trp Lys Thr Val Ser Pro His Arg Ser Pro Ile Ser Asn Met Val Ser
370 375 380

Met Ala Asn Asn His Met Ser Met Thr Asn Ser Gly Val Ser Met Thr
385 390 395 400

Asn Thr Leu Ser Ser Met Leu Lys Gly Phe Ala Pro Ala Ala Ala Ala
405 410 415

Gln Ala Val Gln Thr Ala Ala Gln Asn Gly Val Arg Ala Met Ser Ser
420 425 430

Leu Gly Ser Ser Leu Gly Ser Ser Gly Leu Gly Gly Gly Val Ala Ala
435 440 445

Asn Leu Gly Arg Ala Ala Ser Val Gly Ser Leu Ser Val Pro Gln Ala
450 455 460

Trp Ala Ala Ala Asn Gln Ala Val Thr Pro Ala Ala Arg Ala Leu Pro
465 470 475 480

Leu Thr Ser Leu Thr Ser Ala Ala Glu Arg Gly Pro Gly Gln Met Leu
485 490 495

Gly Gly Leu Pro Val Gly Gln Met Gly Ala Arg Ala Gly Gly Gly Leu
500 505 510

Ser Gly Val Leu Arg Val Pro Pro Arg Pro Tyr Val Met Pro His Ser
515 520 525

Pro Ala Ala Gly Asp Ile Ala Pro Pro Ala Leu Ser Gln Asp Arg Phe
530 535 540

Ala Asp Phe Pro Ala Leu Pro Leu Asp Pro Ser Ala Met Val Ala Gln
545 550 555 560

Val Gly Pro Gln Val Val Asn Ile Asn Thr Lys Leu Gly Tyr Asn Asn
565 570 575

Ala Val Gly Ala Gly Thr Gly Ile Val Ile Asp Pro Asn Gly Val Val
580 585 590

Leu Thr Asn Asn His Val Ile Ala Gly Ala Thr Asp Ile Asn Ala Phe
595 600 605

Ser Val Gly Ser Gly Gln Thr Tyr Gly Val Asp Val Val Gly Tyr Asp
610 615 620

FIG 18C

```
Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Phe Ser Arg Pro Gly
                725                 730                 735

Leu Pro Val Glu Tyr Leu Gln Val Pro Ser Pro Ser Met Gly Arg Asp
            740                 745                 750

Ile Lys Val Gln Phe Gln Ser Gly Gly Asn Asn Ser Pro Ala Val Tyr
        755                 760                 765

Leu Leu Asp Gly Leu Arg Ala Gln Asp Asp Tyr Asn Gly Trp Asp Ile
    770                 775                 780

Asn Thr Pro Ala Phe Glu Trp Tyr Tyr Gln Ser Gly Leu Ser Ile Val
785                 790                 795                 800

Met Pro Val Gly Gly Gln Ser Ser Phe Tyr Ser Asp Trp Tyr Ser Pro
                805                 810                 815

Ala Cys Gly Lys Ala Gly Cys Gln Thr Tyr Lys Trp Glu Thr Phe Leu
            820                 825                 830

Thr Ser Glu Leu Pro Gln Trp Leu Ser Ala Asn Arg Ala Val Lys Pro
        835                 840                 845

Thr Gly Ser Ala Ala Ile Gly Leu Ser Met Ala Gly Ser Ser Ala Met
    850                 855                 860

Ile Leu Ala Ala Tyr His Pro Gln Gln Phe Ile Tyr Ala Gly Ser Leu
865                 870                 875                 880

Ser Ala Leu Leu Asp Pro Ser Gln Gly Met Gly Pro Ser Leu Ile Gly
                885                 890                 895

Leu Ala Met Gly Asp Ala Gly Gly Tyr Lys Ala Ala Asp Met Trp Gly
            900                 905                 910

Pro Ser Ser Asp Pro Ala Trp Glu Arg Asn Asp Pro Thr Gln Gln Ile
        915                 920                 925

Pro Lys Leu Val Ala Asn Asn Thr Arg Leu Trp Val Tyr Cys Gly Asn
    930                 935                 940
```

FIG 18D

Gly Thr Pro Asn Glu Leu Gly Gly Ala Asn Ile Pro Ala Glu Phe Leu
945 950 955 960

Glu Asn Phe Val Arg Ser Ser Asn Leu Lys Phe Gln Asp Ala Tyr Asn
965 970 975

Ala Ala Gly Gly His Asn Ala Val Phe Asn Phe Pro Pro Asn Gly Thr
980 985 990

His Ser Trp Glu Tyr Trp Gly Ala Gln Leu Asn Ala Met Lys Gly Asp
995 1000 1005

Leu Gln Ser Ser Leu Gly Ala Gly
1010 1015

SF 1433477 v1

Alignment of the Amino Acid Sequences of the mature form of Ra35 ( MTB32A ) with the mutated version, Ra mutSA. The single amino acid substitution (S to A) at position 183 is indicated (boxed)

```
                 Ra35 N-Term
1    K K K K K K K|A P P A L S Q D R F A D F P A L P L D P S A N V A Q V G P Q V V N I N T K L G Y N N A   TbRa35
1    K K K K K K K|A P P A L S Q D R F A D F P A L P L D P S A N V A Q V G P Q V V N I N T K L G Y N N A   TbRa35 mutSA

51   V G A G T G I V I D P N G V V L T N N K V I A G A T D I N A F S V G S G Q T Y G V D V V G Y D R T Q   TbRa35
51   V G A G T G I V I D P N G V V L T N N K V I A G A T D I N A F S V G S G Q T Y G V D V V G Y D R T Q   TbRa35 mutSA

101  D V A V L Q L R G A G G L P S A A I G G G V A V G E P V V A K G N S G G Q G G T P R A V P G R V V A   TbRa35
101  D V A V L Q L R G A G G L P S A A I G G G V A V G E P V V A K G N S G G Q G G T P R A V P G R V V A   TbRa35 mutSA
                                                                                        Ra12 C-Term
151  L G Q T V Q A S D S L T G A E E T L N G L I Q F D A A I Q P G D S G G P V V N G L G Q V V G K N|T A   TbRa35
151  L G Q T V Q A S D S L T G A E E T L N G L I Q F D A A I Q P G D[A]G G P V V N G L G Q V V G K N|T A   TbRa35 mutSA
         Ra35 C-Term
201  A S|D N F Q L S Q G G G Q G F A I P I G Q A K A I A G Q I R S G G G S P T V K I G P T A F L G L G V V   TbRa35
201  A S|D N F Q L S Q G G G Q G F A I P I G Q A K A I A G Q I R S G G G S P T V K I G P T A F L G L G V V   TbRa35 mutSA

251  D N N G N G A R V Q R V V G S A P A A S L G I S T G D V I T A V D G A P I N S A T A K A D A L N G K   TbRa35
251  D N N G N G A R V Q R V V G S A P A A S L G I S T G D V I T A V D G A P I N S A T A K A D A L N G K   TbRa35 mutSA

301  K P G D V I S V T K Q T K S G G T R T G N V T L A E G P P A| Ra12 C-Term                           TbRa35
301  K P G D V I S V T K Q T K S G G T R T G N V T L A E G P P A|                                        TbRa35 mutSA
```

Alignment of the Amino Acid Sequences of MTB72F with the Mutated Version MTB72FMutSA. The single amino acid substitution (S to A) at position 710 is indicated (boxed)

```
                                   Ra12 N-Term
1    K K K K K K K|T A A S D N F Q L S Q G G Q G F A I P I G Q A M A I A G Q I R S G G G S P T V K I G P T A F L G   Mtb72f
     K K K K K K K|T A A S D N F Q L S Q G G Q G F A I P I G Q A M A I A G Q I R S G G G S P T V K I G P T A F L G   Mtb72f - mutSA

56   L G V V D N N G N G A R V Q R V V G S A P A A S L G I S T G D V I T A V D G A P I N S A T A K A D A L N G K K   Mtb72f
     L G V V D N N G N G A R V Q R V V G S A P A A S L G I S T G D V I T A V D G A P I N S A T A K A D A L N G K K   Mtb72f - mutSA

                                                       Ra12 C-Term   TbH9FL N-Term
111  P G D V I S V T W Q T K S G G T R T G N V T L A E G P P A|E F|K V D F G A L P P E I N S A R N Y A G P G S A S   Mtb72f
     P G D V I S V T W Q T K S G G T R T G N V T L A E G P P A|E F|K V D F G A L P P E I N S A R N Y A G P G S A S   Mtb72f - mutSA

166  L V A A A Q K W D S V A S D L F S A A S A F Q S V V K G L T V G S W I G S S A G L K V A A A S P Y V A W K S V   Mtb72f
     L V A A A Q K W D S V A S D L F S A A S A F Q S V V K G L T V G S W I G S S A G L K V A A A S P Y V A W K S V   Mtb72f - mutSA

221  T A G Q A E L T A A Q V R V A A A A Y E T A Y G L T V P P P V I A E N R A E L K I L I A T N L L G Q N T F A I   Mtb72f
     T A G Q A E L T A A Q V R V A A A A Y E T A Y G L T V P P P V I A E N R A E L K I L I A T N L L G Q N T F A I   Mtb72f - mutSA

276  A V N E A E Y G E K W A Q D A A A K F G Y A A A T A T A T A T L L P F E E A P E K T S A G G L L E Q A A A V E   Mtb72f
     A V N E A E Y G E K W A Q D A A A K F G Y A A A T A T A T A T L L P F E E A P E K T S A G G L L E Q A A A V E   Mtb72f - mutSA

331  E A S D T A A A K Q L K N N V P Q A L Q Q L A Q F T Q G T T P S S E L G G L W K T V S P K R S P I S N K V S K   Mtb72f
     E A S D T A A A K Q L K N N V P Q A L Q Q L A Q F T Q G T T P S S E L G G L W K T V S P K R S P I S N K V S K   Mtb72f - mutSA

386  A N N K K S K T N S G V S K T N T L S S K L G F A P W A A A A Q A V Q T A A Q N G V R A K S S L G S S L G S S   Mtb72f
     A N N K K S K T N S G V S K T N T L S S K L G F A P W A A A A Q A V Q T A A Q N G V R A K S S L G S S L G S S   Mtb72f - mutSA

441  G L G G G V A A N L G R A A S V G S L S V P Q A W A A A N Q A V T P A A R A L P L T S L T S A A E R G P G Q K   Mtb72f
     G L G G G V A A N L G R A A S V G S L S V P Q A W A A A N Q A V T P A A R A L P L T S L T S A A E R G P G Q K   Mtb72f - mutSA

                                                               TbH9FL C-Term   Ra35 N-Term
496  L G G L P V G Q K G A R A G G G L S G V L R V P P R P Y V K P K S P A A G|D I|A P P A L S Q D R F A D F P A L   Mtb72f
     L G G L P V G Q K G A R A G G G L S G V L R V P P R P Y V K P K S P A A G|D I|A P P A L S Q D R F A D F P A L   Mtb72f - mutSA

551  P L D P S A M V A Q V G P Q V V N I N T K L G Y N N A V G A G T G I V I D P N G V V L T N N K V I A G A T D I   Mtb72f
     P L D P S A M V A Q V G P Q V V N I N T K L G Y N N A V G A G T G I V I D P N G V V L T N N K V I A G A T D I   Mtb72f - mutSA

606  K A F S V G S G Q T Y G V D V V G Y D R T Q D V A V L Q L R G A G G L P S A A I G G G V A V G E P V V A K G N   Mtb72f
     K A F S V G S G Q T Y G V D V V G Y D R T Q D V A V L Q L R G A G G L P S A A I G G G V A V G E P V V A K G N   Mtb72f - mutSA

661  S G G Q G G T P R A V P G R V V A L G Q T V Q A S D S L T G A E E T L N G L I Q F D A A I Q P G D S G G P V V   Mtb72f
     S G G Q G G T P R A V P G R V V A L G Q T V Q A S D S L T G A E E T L N G L I Q F D A A I Q P G D[A]G G P V V   Mtb72f - mutSA

716  K G L G Q V V G K N T A A S|  Ra35 C-Term                                                                      Mtb72f
     K G L G Q V V G K N T A A S|                                                                                   Mtb72f - mutSA
```

FUSION PROTEINS OF MYCOBACTERIUM TUBERCULOSIS

CROSS-REFERENCES TO RELATED APPLICATIONS

The present application is a continuation of U.S. Ser. No. 11/982,179, filed Oct. 31, 2007,now U.S. Pat. No. 7,691993, which is a continuation of U.S. Ser. No. 11/342,364, filed Jan. 26, 2006,now U.S. Pat. No. 7,678,375, which is a division of U.S. Ser. No. 10/369,983, filed Feb. 18, 2003, now U.S. Pat. No. 7,026,465, which claims priority to U.S. Ser. No. 60/357,351, filed Feb. 15, 2002, all of the above-mentioned documents herein incorporated by reference in their entirety.

The present application incorporates by reference the following applications in their entirety: U.S. patent application Ser. No. 09/056,556, filed Apr. 7, 1998, now U.S. Pat. No. 6,350,456; U.S. patent application Ser. No. 09/223,040, filed Dec. 30, 1998, now U.S. Pat. No. 6,544,522; U.S. patent application Ser. No. 09/287,849, filed Apr. 7, 1999, now U.S. Pat. No. 6,627,198; published PCT application No. WO99/51748, filed Apr. 7, 1999 (PCT/US99/07717); U.S. patent application No. 60/158,338, filed Oct. 7, 1999, now abandoned; U.S. patent application No. 60/158,425, filed Oct. 7, 1999, now abandoned; U.S. patent application Ser. No. 09/597,796, filed Jun. 20, 2000, now U.S. Pat. No. 7,186,412; U.S. patent application Ser. No. 09/688,672, filed Oct. 10, 2000, now U.S. Pat. No. 7,311,922; published PCT application No. WO01/24820, filed Oct. 10, 2000 (PCT/US00/28095); U.S. patent application No. 60/265,737, filed Feb. 1, 2001, now abandoned; U.S. patent application Ser. No. 09/886,349, filed Jun. 20, 2001, now U.S. Pat. No. 7,083,796; and published PCT application No. WO01/98460, filed Jun. 20, 2001 (PCT/US01/19959).

STATEMENT AS TO RIGHTS TO INVENTIONS MADE UNDER FEDERALLY SPONSORED RESEARCH OR DEVELOPMENT

Not applicable.

FIELD OF THE INVENTION

The present invention relates to fusion proteins containing at least two *Mycobacterium* sp. antigens. In particular, it relates to nucleic acids encoding fusion proteins that include two or more individual *M. tuberculosis* antigens, which increase serological sensitivity of sera from individuals infected with tuberculosis, and methods for their use in the diagnosis, treatment, and prevention of tuberculosis infection.

BACKGROUND OF THE INVENTION

Tuberculosis is a chronic infectious disease caused by infection with *M. tuberculosis* and other *Mycobacterium* species. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

In order to control the spread of tuberculosis, effective vaccination and accurate early diagnosis of the disease are of utmost importance. Currently, vaccination with live bacteria is the most efficient method for inducing protective immunity. The most common mycobacterium employed for this purpose is *Bacillus* Calmette-Guerin (BCG), an avirulent strain of *M. bovis*. However, the safety and efficacy of BCG is a source of controversy and some countries, such as the United States, do not vaccinate the general public with this agent.

Diagnosis of tuberculosis is commonly achieved using a skin test, which involves intradermal exposure to tuberculin PPD (protein-purified derivative). Antigen-specific T cell responses result in measurable induration at the injection site by 48-72 hours after injection, which indicates exposure to mycobacterial antigens. Sensitivity and specificity have, however, been a problem with this test, and individuals vaccinated with BCG cannot be distinguished from infected individuals.

While macrophages have been shown to act as the principal effectors of *Mycobacterium* immunity, T cells are the predominant inducers of such immunity. The essential role of T cells in protection against *Mycobacterium* infection is illustrated by the frequent occurrence of *Mycobacterium* infection in AIDS patients, due to the depletion of $CD4^+$T cells associated with human immunodeficiency virus (HIV) infection. *Mycobacterium*-reactive $CD4^+$T cells have been shown to be potent producers of γ-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, interleukin-12 (IL-12) has been shown to play a role in stimulating resistance to *M. tuberculosis* infection. For a review of the immunology of *M. tuberculosis* infection, see Chan & Kaufmann, *Tuberculosis: Pathogenesis, Protection and Control* (Bloom ed., 1994), and *Harrison's Principles of Internal Medicine*, volume 1, pp. 1004-1014 and 1019-1023 ($14^{th}$ ed., Fauci et al., eds., 1998).

Accordingly, there is a need for improved diagnostic reagents, and improved methods for diagnosis, preventing and treating tuberculosis.

SUMMARY OF THE INVENTION

The present invention comprises two novel fusion proteins containing at least two *Mycobacterium* sp. antigens. Specifically the nucleic acids encode two fusion polypeptides: MTB32Mut-39F and MTB102F. MTB32Mut-39F includes a mutated MTB32A antigen and a MTB39 antigen (TBH9). MTB102F includes a mutated MTB32A antigen, a MTB39 antigen, and a 85B antigen. The inventors of the present application surprisingly discovered that MTB32Mut SA-39F and MTB102F are expressed at higher levels, are more stable, and are more immunogenic than other *M. tuberculosis* antigens.

One embodiment of the present invention is an isolated nucleic acid encoding a fusion polypeptide comprising a MTB32Mut antigen and a MTB39 (TBH9) antigen from a *Mycobacterium* species of the tuberculosis complex. The nucleic acid hybridizes under highly stringent conditions to a nucleic acid comprising a nucleotide sequence of SEQ ID NO:1 or a complement thereof. The MTB32Mut antigen has a mutation at amino acid position 183 as compared to wild type MTB32A. In one embodiment, the mutation is a serine to alanine mutation. The nucleic acid may comprise a nucleotide sequence SEQ ID NO:1. The nucleic acid may encode an amino acid sequence of SEQ ID NO:2. In another embodiment, the fusion protein further comprises an 85B antigen from a *Mycobacterium* species of the tuberculosis complex. In another embodiment, the nucleic acid comprises SEQ ID NO:3 and encodes an amino acid sequence of SEQ ID NO:4. The *Mycobacterium* may be *Mycobacterium tuberculosis*. An expression vector may comprise the nucleic acid. A host cell may comprise the expression vector. The host cell may be selected from the group consisting of *E. coli*, yeast, and mammalian cells.

Another embodiment of the present invention is an isolated fusion protein encoded by an isolated nucleic acid encoding a fusion polypeptide comprising a mutated MTB32A antigen and a MTB39 antigen from a *Mycobacterium* species of the tuberculosis complex.

Yet another embodiment of the present invention is a composition comprising a an isolated nucleic acid encoding a fusion polypeptide comprising a mutated MTB32A antigen and a MTB39 antigen from a *Mycobacterium* species of the tuberculosis complex, as described above, and a physiologically acceptable carrier. The fusion polypeptide encoded by the nucleic acid may further comprise an NS1 antigen or an immunogenic fragment thereof. The *Mycobacterium* species may be *Mycobacterium tuberculosis*.

Even still another embodiment of the present invention is a composition comprising a mutated MTB32A antigen and a MTB39 antigen from a *Mycobacterium* species of the tuberculosis complex, as described above, and a physiologically acceptable carrier. The composition may further comprise a non-specific immune response enhancer. The nonspecific immune response enhancer may be an adjuvant. The adjuvant may comprise QS21 and MPL in an oil in water emulsion, e.g., with squalene and tocopherol, optionally including CpG. The adjuvant may be selected from the group consisting of ENHANZYN, MPL, 3D-MPL, IFA, QS21, CpG, CWS, TDM, AGP, CPG, Leif, saponin, and saponin mimetics. The composition may further comprise BCG or pVac. The composition may further comprise an NS1 antigen or an immunogenic fragment thereof. The *Mycobacterium* species may be *Mycobacterium tuberculosis*.

Another embodiment of the present invention is a method for detecting tuberculosis in a patient. The dermal cells of a patient are contacted with one or more polypeptides encoded by a nucleic acid encoding a fusion polypeptide comprising a mutated MTB32A antigen and a MTB39 antigen from a *Mycobacterium* species of the tuberculosis complex, as described above. The immune response is detected on the patient's skin and therefrom tuberculosis is detected in the patient. The immune response may be induration.

Even another embodiment of the present invention is a diagnostic kit comprising a polypeptide encoded by a nucleic acid of the invention and an apparatus sufficient to contact the polypeptide encoded by nucleic acid with the dermal cells of a patient.

Still another embodiment of the present invention is a method for eliciting an immune response in a mammal. An immunologically effective amount of a nucleic acid encoding a mutated MTB32A antigen and a MTB39 antigen from a *Mycobacterium* species of the tuberculosis complex, as described above, is administered to the mammal. The mammal may have been immunized with BCG. The mammal may be a human. The composition may be administered prophylactically. The nucleic acid may comprise nucleotide sequence SEQ ID NO:1. The nucleic acid may encode an amino acid sequence of SEQ ID NO:2. In one embodiment, the nucleic acid encoding the fusion protein is first administered, and then a fusion protein booster is later provided.

In another embodiment, the invention provides a method for eliciting an immune response in a mammal, the method comprising the step of administering to the mammal an immunologically effective amount of a composition comprising a mutated MTB32A antigen and a MTB39 antigen from a *Mycobacterium* species of the tuberculosis complex, as described above. The mammal may have been immunized with BCG. The mammal may be a human. The composition may be administered prophylactically. In one embodiment, the fusion protein is first administered, and then a nucleic acid encoding the fusion protein is later provided as a booster.

Another embodiment of the present invention is an isolated nucleic acid encoding a fusion polypeptide comprising a mutated MTB32A antigen, a MTB39 antigen, and a 85B antigen from a *Mycobacterium* species of the tuberculosis complex wherein said nucleic acid hybridizes under highly stringent conditions to a nucleic acid comprising a nucleotide sequence of SEQ ID NO:3 or a complement thereof, and wherein the mutated MTB32A antigen has a mutation at amino acid position 183 as compared to wild type MTB32A. In one embodiment, the mutation is a serine to alanine mutation. The nucleic acid may comprise a nucleotide sequence SEQ ID NO:3. The nucleic acid may encode an amino acid sequence of SEQ ID NO:4. The *Mycobacterium* may be *Mycobacterium tuberculosis*. An expression vector may comprise the nucleic acid. A host cell may comprising the expression vector. The host cell may be selected from the group consisting of *E. coli*, yeast, and mammalian cells.

Still another embodiment of the present invention is an isolated fusion protein encoded by an isolated nucleic acid encoding a fusion polypeptide comprising a mutated MTB32A antigen, a MTB39 antigen, and a 85B antigen from a *Mycobacterium* species of the tuberculosis complex, as described above.

Even still another embodiment of the present invention is a composition comprising an isolated nucleic acid encoding a fusion polypeptide comprising a mutated MTB32A antigen, a MTB39 antigen, and a 85B antigen from a *Mycobacterium* species of the tuberculosis complex, as described above and a physiologically acceptable carrier. The fusion polypeptide encoded by the nucleic acid may further comprises an NS1 antigen or an immunogenic fragment thereof. The *Mycobacterium* species may be *Mycobacterium tuberculosis*.

Even yet another embodiment of the present invention is a composition comprising a fusion protein comprising a mutated MTB32A antigen, a MTB39 antigen, and a 85B antigen from a *Mycobacterium* species of the tuberculosis complex, as described above, and a physiologically acceptable carrier. The composition may comprise a non-specific immune response enhancer. The non-specific immune response enhancer may be an adjuvant. The adjuvant may comprise QS21 and MPL, and optionally CpG. The adjuvant may be selected from the group consisting of ENHANZYN, MPL, 3D-MPL, IFA, QS21, CWS, TDM, AGP, CpG, Leif, saponin, and saponin mimetics. The composition may further comprise BCG or pVac. The composition may further comprise an NS1 antigen or an immunogenic fragment thereof. The *Mycobacterium* species may be *Mycobacterium tuberculosis*.

Still another embodiment of the present invention is a method for detecting tuberculosis in a patient. The contacting dermal cells of a patient are contacted with one or more polypeptides encoded by an isolated nucleic acid encoding a fusion polypeptide comprising a mutated MTB32A antigen, a MTB39 antigen, and a 85B antigen from a *Mycobacterium* species of the tuberculosis complex, as described above. An immune response is detected on the patient's skin and therefrom detecting tuberculosis in the patient. The immune response may be induration. The *Mycobacterium* species may be *Mycobacterium tuberculosis*.

Even still another embodiment of the present invention is a diagnostic kit comprising an isolated nucleic acid encoding a fusion polypeptide comprising a mutated MTB32A antigen, a MTB39 antigen, and a 85B antigen from a *Mycobacterium* species of the tuberculosis complex, as described above and an apparatus sufficient to contact the polypeptide encoded by nucleic acid with the dermal cells of a patient.

Still even another embodiment of the present invention is a method for eliciting an immune response in a mammal, the method comprising the step of administering to the mammal an immunologically effective amount of a nucleic acid encoding a mutated MTB32A antigen, a MTB39 antigen, and a 85B antigen from a *Mycobacterium* species of the tuberculosis complex, as described above. The mammal may have been immunized with BCG. The mammal may be a human. The composition may be administered prophylactically. The nucleic acid may comprise nucleotide sequence SEQ ID NO:3. The nucleic acid may encode an amino acid sequence of SEQ ID NO:4.

Yet another embodiment of the present invention is a method for eliciting an immune response in a mammal. An immunologically effective amount of a composition comprising a mutated MTB32A antigen, a MTB39 antigen, and a 85B antigen from a *Mycobacterium* species of the tuberculosis complex, as described above, is administered to the mammal. The nucleic acid may comprise nucleotide sequence SEQ ID NO:3. The nucleic acid may encode an amino acid sequence of SEQ ID NO:4. The mammal may have been immunized with BCG. The mammal may be a human. The composition may be administered prophylactically.

In yet another embodiment, the present invention provides nucleic acid sequences and amino acid sequences encoding the MTB72F fusion protein further fused to the following antigens: MAPS (fusion r95F), Erd14 (fusion MTB89F), MTI (fusion MTB83F), DPV (fusion MTB81F), mTCC#2 (fusion MTB114F), hTCC#1 (fusion MTB102tm2F) and 85b complex antigen from *M. bovis* (fusion MTB103F). MTB72F fusion protein is a 72 kDa polyprotein fusion construct comprising Ra12 (C-terminus of mature Ra35), TbH9, and Ra35 (N-terminus of mature Ra35) (for Ra12 and Ra35 sequences, see, e.g., FIG. 19).

BRIEF DESCRIPTION OF THE DRAWINGS

FIG. 1 shows the nucleotide sequence that encodes the MTB32-MTB39F fusion protein (SEQ ID NO:1).

FIG. 2 shows the amino acid sequence of the mutated MTB32-MTB39F fusion protein (SEQ ID NO:2).

FIG. 3 shows the nucleotide sequence that encodes the MTB-102F fusion protein (SEQ ID NO:3).

FIG. 4 shows the amino acid sequence of the MTB102F fusion protein (SEQ ID NO:4).

FIG. 5 shows the nucleic acid sequence for MTB72F-MAPS (fusion r95F; SEQ ID NO:5).

FIG. 6 shows the nucleic acid sequence for MTB72F-Erd14 (fusion MTB89F; SEQ ID NO:6).

FIG. 7 shows the nucleic acid sequence for MTB72F-MTI (fusion MTB83F; SEQ ID NO:7).

FIG. 8 shows the nucleic acid sequence for MTB72F-DPV (fusion MTB81F; SEQ ID NO:8).

FIG. 9 shows the nucleic acid sequence for MTB72F-mTCC#2 (fusion MTB114F; SEQ ID NO:9).

FIG. 10 shows the nucleic acid sequence for MTB72F-hTCC#1 (fusion MTB102tm2F; SEQ ID NO:10).

FIG. 11 shows the nucleic acid sequence for MTB72F and 85b complex antigen from *M. bovis* (fusion MTB103F; SEQ ID NO:11).

FIG. 12 shows the amino acid sequence for MTB72F-MAPS (fusion r95F; SEQ ID NO:12).

FIG. 13 shows the amino acid sequence for MTB72F-Erd14 (fusion MTB89F; SEQ ID NO:13).

FIG. 14 shows the amino acid sequence for MTB72F-MTI (fusion MTB83F; SEQ ID NO:14).

FIG. 15 shows the amino acid sequence for MTB72F-DPV (fusion MTB81F; SEQ ID NO:15).

FIG. 16 shows the amino acid sequence for MTB72F-mTCC#2 (fusion MTB114F; SEQ ID NO:16).

FIG. 17 shows the amino acid sequence for MTB72F-hTCC#1 (fusion MTB102tm2F; SEQ ID NO:17).

FIG. 18 shows the amino acid sequence for MTB72F and 85b complex antigen from *M. bovis* (fusion MTB103F; SEQ ID NO:18).

FIG. 19 shows an alignment of MTB32AMutSA and wild-type MBT32A.

FIG. 20 shows an alignment of MTB72FMutSA with MTB72F.

DETAILED DESCRIPTION OF THE INVENTION

Definitions

"Fusion polypeptide" or "fusion protein" refers to a protein having at least two heterologous *Mycobacterium* sp. polypeptides covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. This term also refers to conservatively modified variants, polymorphic variants, alleles, mutants, subsequences, interspecies homologs, and immunogenic fragments of the antigens that make up the fusion protein. *Mycobacterium tuberculosis* antigens are described in Cole et al., Nature 393:537 (1998), which discloses the entire *Mycobacterium tuberculosis* genome. Antigens from other *Mycobacterium* species that correspond to *M. tuberculosis* antigens can be identified, e.g., using sequence comparison algorithms, as described herein, or other methods known to those of skill in the art, e.g., hybridization assays and antibody binding assays. Fusion proteins of the invention can also comprise additional copies of a component antigen or immunogenic fragment thereof.

A polynucleotide sequence comprising a fusion protein of the invention hybridizes under stringent conditions to at least two nucleotide sequences, each encoding an antigen polypeptide selected from the group consisting of MTB39 or an immunogenic fragment thereof, mutated MTB32A or an immunogenic fragment thereof, and 85B or an immunogenic fragment thereof. The polynucleotide sequences encoding the individual antigens of the fusion polypeptide therefore include conservatively modified variants, polymorphic variants, alleles, mutants, subsequences, immunogenic fragments, and interspecies homologs of MTB39, MTB32A, and 85B. The polynucleotide sequence encoding the individual polypeptides of the fusion protein can be in any order.

In some embodiments, the individual polypeptides of the fusion protein are in order (N- to C-terminus) from large to small. Large antigens are approximately 30 to 150 kD in size, medium antigens are approximately 10 to 30 kD in size, and small antigens are approximately less than 10 kD in size. The sequence encoding the individual polypeptide may be as small as, e.g., an immunogenic fragment such as an individual CTL epitope encoding about 8 to 9 amino acids, or, e.g., an HTL or B cell epitope. The fragment may also include multiple epitopes. The immunogenic fragment may also represent a larger part of the antigen sequence, e.g., about 50% or more of MTB39, 85B, and MTB32A, e.g., the N- and C-terminal portions of MTB32A.

A fusion polypeptide of the invention specifically binds to antibodies raised against at least two antigen polypeptides, wherein each antigen polypeptide is selected from the group consisting of MTB39 or an immunogenic portion or fragment thereof, mutated MTB32A or an immunogenic portion thereof, and 85B or an immunogenic portion thereof. The antibodies can be polyclonal or monoclonal. Optionally, the fusion polypeptide specifically binds to antibodies raised against the fusion junction of the antigens, which antibodies do not bind to the antigens individually, i.e., when they are not part of a fusion protein. The fusion polypeptides optionally comprise additional polypeptides, e.g., three, four, five, six, or more polypeptides, up to about 25 polypeptides, optionally heterologous polypeptides or repeated homologous polypeptides, fused to the at least two heterologous antigens. The additional polypeptides of the fusion protein are optionally derived from *Mycobacterium* as well as other sources, such as other bacterial, viral, or invertebrate, vertebrate, or mammalian sources. The individual polypeptides of the fusion protein can be in any order. As described herein, the fusion protein can also be linked to other molecules, including additional polypeptides. The compositions of the invention can also comprise additional polypeptides that are unlinked to the fusion proteins of the invention. These additional polypeptides may be heterologous or homologous polypeptides.

The term "fused" refers to the covalent linkage between two polypeptides in a fusion protein. The polypeptides are typically joined via a peptide bond, either directly to each other or via an amino acid linker. Optionally, the peptides can be joined via non-peptide covalent linkages known to those of skill in the art.

"FL" refers to full-length, i.e., a polypeptide that is the same length as the wild-type polypeptide. In some embodiment, the FL version is the mature version, that is, the secreted, full length form lacking the signal sequence.

The term "immunogenic fragment thereof" refers to a polypeptide comprising an epitope that is recognized by cytotoxic T lymphocytes, helper T lymphocytes or B cells.

An amount of a composition, nucleic acid, or fusion protein that elicits an immune response is an "immunogenically" or "immunologically" "effective amount" of the composition, nucleic acid or polypeptide.

MTB32AMutSA is a mutated version of wild-type MTB32A (Ra35FL or Ra35 mature). The sequence of wild-type RA35 is disclosed as SEQ ID NO:17 (cDNA) and SEQ ID NO:79 (protein) in the U.S. patent applications Ser Nos. 08/523,436 (now abandoned), Ser. No. 08/523,435 (now abandoned), Ser. No. 08/658,800 (now abandoned), Ser. No. 08/659,683 (now abandoned), Ser. No. 08/818,112 (now U.S. Pat. No. 6,290,969), Ser. No. 09/056,556 (now U.S. Pat. No. 6,350,456), and Ser. No. 08/818,111 (now U.S. Pat. No. 6,338,852) and in the WO97/09428 and WO97/09429 applications, see also Skeiky et al., Infection and Immunity 67:3998-4007 (1999). The term mutated MTB32, mutated MTB32A, MTB32AMutSA or MTB32MutSA includes MTB32A amino acid sequences in which any one of the three amino acids at the active site triad (His, Asp, Ser, amino acid positions 182-184 of the wild type molecule), e.g., the serine residue at amino acid position 183 in wild-type MTB32A, has been changed to another amino acid (e.g., to alanine, Ra35FLMutSA, see, e.g., the sequence comparison of wild type and mutated MTB32 in FIG. 5).

MTB39 (TbH9), the sequence of which is disclosed as SEQ ID NO:106 (cDNA full length) and SEQ ID NO:107 (protein full length) in the U.S. patent applications Ser. No. 08/658,800 (now abandoned), Ser. No. 08/659,683 (now abandoned), Ser. No. 08/818,112 (now U.S. Pat. No. 6,290,969), and Ser. No. 08/818,111 (now U.S. Pat. No. 6,338,852) and in the WO97/09428 and WO97/09429 applications. The sequence is also disclosed as SEQ ID NO:33 (DNA) and SEQ ID NO:91 (amino acid) in U.S. patent application Ser. No. 09/056,559.

MTB72F (Ra12-TbH9-Ra35), the sequence of which is disclosed as SEQ ID NO:1 (DNA) and SEQ ID NO:2 (protein) in the U.S. patent application Ser. No. 09/223,040 (now U.S. Pat. No. 6,544,522), and in the PCT/US99/07717 application.

85 complex antigen, e.g., 85b antigen from *M. bovis*, the sequence of which is disclosed in Content et al., *Infect. & Immunol.* 59:3205-3212 (1991).

The term "*Mycobacterium* species of the tuberculosis complex" includes those species traditionally considered as causing the disease tuberculosis, as well as *Mycobacterium* environmental and opportunistic species that cause tuberculosis and lung disease in immune compromised patients, such as patients with AIDS, e.g., *M. tuberculosis, M. bovis*, or *M. africanum*, BCG, *M. avium, M. intracellulare, M. celatum, M. genavense, M. haemophilum, M. kansasii, M. simiae, M. vaccae, M. fortuitum*, and *M. scrofulaceum* (see, e.g., Harrison's *Principles of Internal Medicine*, volume 1, pp. 1004-1014 and 1019-1023 ($14^{th}$ ed., Fauci et al., eds., 1998).

An adjuvant refers to the components in a vaccine or therapeutic composition that increase the specific immune response to the antigen (see, e.g., Edelman, *AIDS Res. Hum Retroviruses* 8:1409-1411 (1992)). Adjuvants induce immune responses of the Th1-type and Th-2 type response. Th1-type cytokines (e.g., IFN-γ, IL-2, and IL-12) tend to favor the induction of cell-mediated immune response to an administered antigen, while Th-2 type cytokines (e.g., IL-4, IL-5, I1-6, IL-10 and TNF-(β) tend to favor the induction of humoral immune responses.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins: *Structures and Molecular Properties*; First Ed. (1984)).

The term "heterologous" when used with reference to portions of a nucleic acid indicates that the nucleic acid comprises two or more subsequenceg that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen.

The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to fusion proteins can be selected to obtain only those polyclonal antibodies that are specifically immunoreactive with fusion protein and not with individual components of the fusion proteins. This selection may be achieved by subtracting out antibodies that cross-react with the individual antigens. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988), for a description of immunoassay formats and conditions that can be used to determine specific immunoreactivity). Typically a specific or selective reaction will be at least twice background signal or noise and more typically more than 10 to 100 times background.

Polynucleotides may comprise a native sequence (i.e., an endogenous sequence that encodes an individual antigen or a portion thereof) or may comprise a variant of such a sequence. Polynucleotide variants may contain one or more substitutions, additions, deletions and/or insertions such that the biological activity of the encoded fusion polypeptide is not diminished, relative to a fusion polypeptide comprising native antigens. Variants preferably exhibit at least about 70% identity, more preferably at least about 80% identity and most preferably at least about 90% identity to a polynucleotide sequence that encodes a native polypeptide or a portion thereof.

The terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, or 95% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of &test sequence. Optionally, the identity exists over a region that is at least about 25 to about 50 amino acids or nucleotides in length, or optionally over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 25 to 500, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

One example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Polynucleotide Compositions

As used herein, the terms "DNA segment" and "polynucleotide" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the DNA segments of this invention can include genomic sequences, extra-genomic and plasmid-encoded sequences and smaller engineered gene segments that express, or may be adapted to express, proteins, polypeptides, peptides and the like. Such segments may be naturally isolated, or modified synthetically by the hand of man.

The terms "isolated," "purified," or "biologically pure" therefore refer to material that is substantially or essentially free from components that normally accompany it as found in its native state. Of course, this refers to the DNA segment as originally isolated, and does not exclude other isolated proteins, genes, or coding regions later added to the composition by the hand of man. Purity and homogeneity are typically determined using analytical chemistry techniques such as polyacrylamide gel electrophoresis or high performance liquid chromatography. A protein that is the predominant species present in a preparation is substantially purified. An isolated nucleic acid is separated from other open reading frames that flank the gene and encode proteins other than the gene.

As will be recognized by the skilled artisan, polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Mycobacterium* antigen or a portion thereof) or may comprise a variant, or a biological or antigenic functional equivalent of such a sequence. Polynucleotide variants may contain one or more substitutions, additions, deletions and/or insertions, as further described below, preferably such that the immunogenicity of the encoded polypeptide is not diminished, relative to a native tumor protein. The effect on the immunogenicity of the encoded polypeptide may generally be assessed as described herein. The term "variants" also encompasses homologous genes of xenogenic origin.

In additional embodiments, the present invention provides isolated polynucleotides and polypeptides comprising various lengths of contiguous stretches of sequence identical to or complementary to one or more of the sequences disclosed herein. For example, polynucleotides are provided by this invention that comprise at least about 15, 20, 30, 40, 50, 75, 100, 150, 200, 300, 400, 500 or 1000 or more contiguous nucleotides of one or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Moreover, it will be appreciated by those of ordinary skill in the art that, as a result of the degeneracy of the genetic code, there are many nucleotide sequences that encode a MTB32Mut-39F or MTB102F polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotide Identification and Characterization

Polynucleotides encoding MTB32Mut-39F or MTB102F may be identified, prepared and/or manipulated using any of a variety of well established techniques. For example, a polynucleotide encoding MTB32Mut-39F or MTB102F may be identified, as described in more detail below, by screening a microarray of cDNAs for tumor-associated expression (i.e., expression that is at least two fold greater in a tumor than in normal tissue, as determined using a representative assay provided herein). Such screens may be performed, for example, using a Synteni microarray (Palo Alto, Calif.) according to the manufacturer's instructions (and essentially as described by Schena et al., *Proc. Natl. Acad. Sci. USA* 93:10614-10619 (1996) and Heller et al., *Proc. Natl. Acad. Sci. USA* 94:2150-2155 (1997)). Alternatively, polynucleotides may be amplified from cDNA prepared from cells expressing the proteins described herein, such as *M. tuberculosis* cells. Such polynucleotides may be amplified via polymerase chain reaction (PCR). For this approach, sequence-specific primers may be designed based on the sequences provided herein, and may be purchased or synthesized.

An amplified portion of a polynucleotide of the present invention may be used to isolate a full length gene from a suitable library (e.g., a *M. tuberculosis* cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then generally screened by hybridizing filters containing denatured bacterial colonies (or lawns containing phage plaques) with the labeled probe (see Sambrook et al., *Molecular Cloning: A Laboratory Manual* (1989)). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences can then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22-30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111-19 (1991)) and walking PCR (Parker et al., *Nucl. Acids. Res.* 19:3055-60 (1991)). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Polynucleotide Expression in Host Cells

In other embodiments of the invention, polynucleotide sequences or fragments thereof which encode MTB32Mut-39F or MTB102F, or fusion proteins or functional equivalents thereof, may be used in recombinant DNA molecules to direct expression of a MTB32Mut-39F or MTB102F polypeptide in appropriate host cells. Due to the inherent degeneracy of the genetic code, other DNA sequences that encode substantially the same or a functionally equivalent amino acid sequence may be produced and these sequences may be used to clone and express a given polypeptide.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter polypeptide encoding sequences for a variety of reasons, including but not limited to, alterations which modify the cloning, processing, and/or expression of the gene product. For example, DNA shuffling by random fragmentation and PCR reassembly of gene fragments and synthetic oligonucleotides may be used to engineer the nucleotide sequences. In addition, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences may be ligated to a heterologous sequence to encode a fusion protein. For example, to screen peptide libraries for inhibitors of polypeptide activity, it may be useful to encode a chimeric protein that can be recognized by a commercially available antibody. A fusion protein may also be engineered to contain a cleavage site located between the polypeptide-encoding sequence and the heterologous protein sequence, so that the polypeptide may be cleaved and purified away from the heterologous moiety.

Sequences encoding a desired polypeptide may be synthesized, in whole or in part, using chemical methods well known in the art (see Caruthers, M. H. et al., *Nucl. Acids Res. Symp. Ser.* pp. 215-223 (1980), Horn et al., *Nud Acids Res. Symp. Ser.* pp. 225-232 (1980)). Alternatively, the protein itself may be produced using chemical methods to synthesize the amino acid sequence of a polypeptide, or a portion thereof. For example, peptide synthesis can be performed using various solid-phase techniques (Roberge et al., *Science* 269:202-204 (1995)) and automated synthesis may be achieved, for example, using the ABI 431A Peptide Synthesizer (Perkin Elmer, Palo Alto, Calif.).

A newly synthesized peptide may be substantially purified by preparative high performance liquid chromatography (e.g., Creighton, *Proteins, Structures and Molecular Principles* (1983)) or other comparable techniques available in the art. The composition of the synthetic peptides may be confirmed by amino acid analysis or sequencing (e.g., the Edman degradation procedure). Additionally, the amino acid sequence of a polypeptide, or any part thereof, may be altered during direct synthesis and/or combined using chemical methods with sequences from other proteins, or any part thereof, to produce a variant polypeptide.

In order to express a desired polypeptide, the nucleotide sequences encoding the polypeptide, or functional equivalents, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., *Molecular Cloning, A Laboratory Manual* (1989), and Ausubel et al., *Current Protocols in Molecular Biology* (1989).

A variety of expression vector/host systems may be utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORT1 plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, for example for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding the polypeptide of interest may be ligated into the vector in frame with sequences for the amino-terminal Met and the subsequent 7 residues of β-galactosidase so that a hybrid protein is produced; pIN vectors (Van Heeke & Schuster, *J. Biol. Chem.* 264:5503-5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al., *Methods Enzymol.* 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, *EMBO J.* 6:307-311 (1987)). Alternatively, plant promoters such as the small subunit of RUBISCO or heat shock promoters may be used (Coruzzi et al., *EMBO J.* 3:1671-1680 (1984); Broglie et al., *Science* 224:838-843 (1984); and Winter et al., *Results Probl. Cell Differ.* 17:85-105 (1991)). These constructs can be introduced into plant cells by direct DNA transformation or pathogen-mediated transfection. Such techniques are described in a number of generally available reviews (see, e.g., Hobbs in *McGraw Hill Yearbook of Science and Technology* pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia larvae*. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia larvae* in which the polypeptide of interest may be expressed (Engelhard et al., *Proc. Natl. Acad. Sci. U.S.A.* 91:3224-3227 (1994)).

In mammalian host cells, a number of viral-based expression systems are generally available. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, *Proc. Natl. Acad. Sci. U.S.A.* 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., *Results Probl. Cell Differ.* 20:125-162 (1994)).

In addition, a host cell strain may be chosen for its ability to modulate the expression of the inserted sequences or to process the expressed protein in the desired fashion. Such modifications of the polypeptide include, but are not limited to, acetylation, carboxylation. glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a polynucleotide of interest may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., *Cell* 11:223-32 (1977)) and adenine phosphoribosyltransferase (Lowy et al., *Cell* 22:817-23 (1990)) genes which can be employed in tk.sup.- or aprt.sup.- cells, respectively. Also, antimetabolite, antibiotic or herbicide resistance can be used as the basis for selection; for example, dhfr which confers resistance to methotrexate (Wigler et al., *Proc. Natl. Acad. Sci. U.S.A.* 77:3567-70 (1980)); npt, which confers resistance to the aminoglycosides, neomycin and G-418 (Colbere-Garapin et al., *J. Mol. Biol.* 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, *Proc. Natl. Acad. Sci. U.S.A.* 85:8047-51 (1988)). Recently, the use of visible markers has gained popularity with such markers as anthocyanins, β-glucuronidase and its substrate GUS, and luciferase and its substrate luciferin, being widely used not only to identify transformants, but also to quantify the amount of transient or stable protein expression attributable to a specific vector system (Rhodes et al., *Methods Mol. Biol.* 55:121-131 (1995)).

Although the presence/absence of marker gene expression suggests that the gene of interest is also present, its presence and expression may need to be confirmed. For example, if the sequence encoding a polypeptide is inserted within a marker gene sequence, recombinant cells containing sequences can be identified by the absence of marker gene function. Alternatively, a marker gene can be placed in tandem with a polypeptide-encoding sequence under the control of a single promoter. Expression of the marker gene in response to induction or selection usually indicates expression of the tandem gene as well.

Alternatively, host cells which contain and express a desired polynucleotide sequence may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed. These and other assays are described, among other places, in Hampton et al., *Serological Methods, a Laboratory Manual* (1990) and Maddox et al., *J. Exp. Med.* 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen. San Diego, Calif.) between the purification domain and the encoded polypeptide may be used to facilitate purification. One such expression vector provides for expression of a fusion protein containing a polypeptide of interest and a nucleic acid encoding 6 histidine residues preceding a thioredoxin or an enterokinase cleavage site. The histidine residues facilitate purification on IMIAC (immobilized metal ion affinity chromatography) as described in Porath et al., *Prot. Exp. Purif.* 3:263-281 (1992) while the enterokinase cleavage site provides a means for purifying the desired polypeptide from the fusion protein. A discussion of vectors which contain fusion proteins is provided in Kroll et al., *DNA Cell Biol.* 12:441-453 (1993)).

In addition to recombinant production methods, MTB32Mut-39F or MTB102F polypeptides of the invention, and fragments thereof, may be produced by direct peptide synthesis using solid-phase techniques (Merrifield, *J. Am. Chem. Soc.* 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments may be chemically synthesized separately and combined using chemical methods to produce the full length molecule.

In Vivo Polynucleotide Delivery Techniques

In additional embodiments, genetic constructs comprising one or more of the polynucleotides encoding mutated MTB32Mut-39F or an immunogenic fragment thereof; or MTB102F or an immunogenic fragment thereof are introduced into cells in vivo. This may be achieved using any of a variety or well known approaches, several of which are outlined below for the purpose of illustration.

1. Adenovirus

One of the preferred methods for in vivo delivery of one or more nucleic acid sequences involves the use of an adenovirus expression vector. “Adenovirus expression vector” is meant to include those constructs containing adenovirus sequences sufficient to (a) support packaging of the construct and (b) to express a polynucleotide that has been cloned therein in a sense or antisense orientation. Of course, in the context of an antisense construct, expression does not require that the gene product be synthesized.

The expression vector comprises a genetically engineered form of an adenovirus. Knowledge of the genetic organization of adenovirus, a 36 kb, linear, double-stranded DNA virus, allows substitution of large pieces of adenoviral DNA with foreign sequences up to 7 kb (Grunhaus A, et al., Virology,1994 May 1;200(2):535-46). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (B) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, Radiother Oncol. 1990 November;19(3):197-218). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA’s issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Generation and propagation of the current adenovirus vectors, which are replication deficient, depend on a unique helper cell line, designated 293, which was transformed from human embryonic kidney cells by Ad5 DNA fragments and constitutively expresses E1 proteins (Graham et al., Adv Cancer Res. 1977;25:1-51). Since the E3 region is dispensable from the adenovirus genome (Jones & Shenk, Cell. 1978 January;13(1):181-8), the current adenovirus vectors, with the help of 293 cells, carry foreign DNA in either the E1, the D3 or both regions (Prevec et al. J Acquir Immune Defic Syndr. 1991;4(6):568- 76). In nature, adenovirus can package approximately 105% of the wild-type genome (Ghosh-Choudhury et al., Biochem Biophys Res Commun. 1987 Sep 30;147(3):964-73), providing capacity for about 2 extra kB of DNA. Combined with the approximately 5.5 kB of DNA that is replaceable in the E1 and E3 regions, the maximum capacity of the current adenovirus vector is under 7.5 kB, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, Science. 1993 May 14;260(5110):926-32).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the currently preferred helper cell line is 293.

Recently, Griffiths and Racher (Cytotechnology. 1994;15 (1-3):3-9) disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlemneyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A-F. Adenovirus type 5 of subgroup C is the preferred starting material in order to obtain a conditional replication-defective adenovirus vector for use in the present invention, since Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (EMBO J. 1986 September;5(9):2377-85) or in the E4 region where a helper cell line or helper virus complements the E4 defect.

Adenovirus is easy to grow and manipulate and exhibits broad host range in vitro and in vivo. This group of viruses can be obtained in high titers, e.g., 10.sup.9-10.sup.11 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch RB et al., Am Rev Respir Dis. 1963 September;88:SUPPL 394-403; Top et al., J Infect Dis. 1971 August;124(2):155-60), demonstrating their safety and therapeutic potential as in vivo gene transfer vectors.

Adenovirus vectors have been used in eukaryotic gene expression (Levrero et al., Gene. 1991 May 30;101(2):195-202; Gomez-Foix et al., J Biol Chem. 1992 Dec 15;267(35): 25129 -34) and vaccine development (Grunhaus & Horwitz, Virology,1994 May 1;200(2):535-46; Prevec et al. J Acquir Immune Defic Syndr. 1991;4(6):568-76). Recently, animal studies suggested that recombinant adenovirus could be used for gene therapy (Rosenfeld et al., Science. 1991 Apr. 19;252 (5004):431-4; Stratford-Perricaudet et al., Hum Gene Ther. 1990 Fall;1(3):241-56; Rich et al. Hum Gene Ther. 1993 August; 4(4):461-76). Studies in administering recombinant adenovirus to different tissues include trachea instillation (Rosenfeld et al., 1991, supra; Rosenfeld et al., Cell. 1992 Jan 10;68(1):143-55), muscle injection (Ragot Nature. 1993 Feb 18;361(6413):647-50), peripheral intravenous injections (Herz & Gerard, Proc Natl Acad Sci U S A. 1993 Apr 1;90 (7):2812 6) and stereotactic inoculation into the brain (Le Gal La Salle et al., Gene Ther. 1994;1 Suppl 1:S52).

2. Retroviruses

The retroviruses are a group of single-stranded RNA viruses characterized by an ability to convert their RNA to double-stranded DNA in infected cells by a process of reverse-transcription (Coffin, J Med Virol. 1990 May;31(1): 43-9). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990, supra).

In order to construct a retroviral vector, a nucleic acid encoding one or more oligonucleotide or polynucleotide sequences of interest is inserted into the viral genome in the place of certain viral sequences to produce a virus that is replication-defective. In order to produce virions, a packaging cell line containing the gag, pol, and env genes but without the LTR and packaging components is constructed (Mann et al., Cell. 1983 May;33(1):153-9). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas & Rubenstein, Biotechnology 1988;10:493-513; Temin HM, Cell Biophys. 1986 December;9(1 -2):9-16; Mann et al., 1983, supra). The media containing the recombinant retroviruses is then collected, optionally concentrated, and used for gene transfer. Retroviral vectors are able to infect a broad variety of cell types. However, integration and stable expression require the division of host cells (Paskind et al., Virology. 1975 September;67(1):242-8).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., Proc Natl Acad Sci U S A. 1989 December;86(23):9079-83). Using antibodies against major histocompatibility complex class I and class II antigens, they demonstrated the infection of a variety of human cells that bore those surface antigens with an ecotropic virus in vitro (Roux et al., 1989, supra).

3. Adeno-Associated Viruses

AAV (Ridgway, Biotechnology 1988;10:467-92, ; Hermonat & Muzycska, Proc Natl Acad Sci U S A. 1984 October; 81(20):6466-70) is a parvovirus, discovered as a contamination of adenoviral stocks. It is a ubiquitous virus (antibodies are present in 85% of the US human population) that has not been linked to any disease. It is also classified as a dependovirus, because its replications is dependent on the presence of a helper virus, such as adenovirus. Five serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter (Muzyczka & McLaughlin, J. Virol. 1988 June;62(6):1963-73).

The AAV DNA is approximately 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three viral promoters have been identified and named p5, p19, and p40, according to their map position. Transcription from p5 and p19 results in production of rep proteins, and transcription from p40 produces the capsid proteins (Hermonat & Muzyczka, 1984, supra).

There are several factors that prompted researchers to study the possibility of using rAAV as an expression vector One is that the requirements for delivering a gene to integrate into the host chromosome are surprisingly few. It is necessary to have the 145-bp ITRs, which are only 6% of the AAV genome. This leaves room in the vector to assemble a 4.5-kb DNA insertion. While this carrying capacity may prevent the AAV from delivering large genes, it is amply suited for delivering the antisense constructs of the present invention.

AAV is also a good choice of delivery vehicles due to its safety. There is a relatively complicated rescue mechanism: not only wild type adenovirus but also AAV genes are required to mobilize rAAV. Likewise, AAV is not pathogenic and not associated with any disease. The removal of viral coding sequences minimizes immune reactions to viral gene expression, and therefore, rAAV does not evoke an inflammatory response.

4. Other Viral Vectors as Expression Constructs

Other viral vectors may be employed as expression constructs in the present invention for the delivery of oligonucleotide or polynucleotide sequences to a host cell. Vectors derived from viruses such as vaccinia virus (Ridgeway, supra; Coupar et al., Gene. 1988 Aug 15;68(1):1-10), lentiviruses, polio viruses and herpes viruses may be employed. They offer several attractive features for various mammalian cells (Friedmann, Mol Biol Med. 1989 April;6(2):117-25; Ridgeway, 1988, supra ; Coupar et al., 1988, supra; Summers J, Smith PM, and Horwich AL, J Virol. 1990 June;64(6):2819-24).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al, J Virol. 1990 February;64 (2):642-50). This suggested that large portions of the genome could be replaced with foreign genetic material. The hepatotropism and persistence (integration) were particularly attractive properties for liver-directed gene transfer. Chang et al. (Hepatology, 14:124A, 1991) introduced the chloramphenicol acetyltransferase (CAT) gene into duck hepatitis B virus genome in the place of the polymerase, surface, and pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991, supra).

5. Non-Viral Vectors

In order to effect expression of the oligonucleotide or polynucleotide sequences of the present invention, the expression construct must be delivered into a cell. This delivery may be accomplished in vitro, as in laboratory procedures for transforming cells lines, or in vivo or ex vivo, as in the treatment of certain disease states. As described above, one preferred mechanism for delivery is via viral infection where the expression construct is encapsulated in an infectious viral particle.

Once the expression construct has been delivered into the cell the nucleic acid encoding the desired oligonucleotide or polynucleotide sequences may be positioned and expressed at different sites. In certain embodiments, the nucleic acid encoding the construct may be stably integrated into the genome of the cell. This integration may be in the specific location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In certain embodiments of the invention, the expression construct comprising one or more oligonucleotide or polynucleotide sequences may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Nat. Acad. Sci. USA, 81:7529-7533, 1984) successfully injected polyomavirus DNA in the form of calcium phosphate precipitates into liver and spleen of adult and newborn mice demonstrating active viral replication and acute infection. Benvenisty & Reshef (Proc. Nat. Acad. Sci. USA, 83:9551-9555, 1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., Nature 1987 327:70-73). Several devices for accelerating small particles have been developed. One such device relies on a high voltage discharge to generate an electrical current, which in turn provides the motive force (Yang et al., Proc. Natl. Acad. Sci. USA, 1990 87:9568-9572). The microprojectiles used have consisted of biologically inert substances such as tungsten or gold beads.

Selected organs including the liver, skin, and muscle tissue of rats and mice have been bombarded in vivo (Yang et al, 1990, supra; Zelenin et al., FEBS Lett., 1991 280:94-96). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

Polypeptide Compositions

The present invention, in other aspects, provides polypeptide compositions. Generally, a polypeptide of the invention will be an isolated polypeptide (or an epitope, variant, or active fragment thereof) derived from a mammalian species. Preferably, the polypeptide is encoded by a polynucleotide sequence disclosed herein or a sequence which hybridizes under moderately stringent conditions to a polynucleotide sequence disclosed herein. Alternatively, the polypeptide may be defined as a polypeptide which comprises a contiguous amino acid sequence from an amino acid sequence disclosed herein, or which polypeptide comprises an entire amino acid sequence disclosed herein.

Immunogenic portions may generally be identified using well known techniques, such as those summarized in Paul, *Fundamental Immunology,* 3rd ed., 243-247 (1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a *Mycobacterium* sp. protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow & Lane, *Antibodies: A Laboratory Manual* (1988). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, and higher eukaryotic cells, such as mammalian cells and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Polypeptides of the invention, immunogenic fragments thereof, and other variants having less than about 100 amino acids, and generally less than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146 (1963). Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46 (1985); Murphy et al., *Proc. Natl. Acad. Sci. USA* 83:8258-8262 (1986); U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided. Such proteins comprise a polypeptide as described herein together with an unrelated immunogenic protein. Preferably the immunogenic protein is capable of eliciting a recall response. Examples of such proteins include tetanus, tuberculosis and hepatitis proteins (see, e.g., Stoute et al., *New Engl. J. Med.* 336:86-91 (1997)).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100-110 amino acids), and a protein D derivative may be lipidated. Within certain preferred embodiments, the first 109 residues of a lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795-798 (1992)). Within a preferred embodiment, a repeat portion of LYTA may be incorporated into a fusion protein. A repeat portion is found in the C-terminal region starting at residue 178. A particularly preferred repeat portion incorporates residues 188-305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

T Cells

Immunotherapeutic compositions may also, or alternatively, comprise T cells specific for MTB32Mut-39F or an immunogenic fragment thereof and MTB102F or an immunogenic fragment thereof. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the Isolex™ System, available from Nexell Therapeutics, Inc. (Irvine, Calif.; see also U.S. Pat. Nos. 5,240,856; 5,215,926; WO 89/06280; WO 91/16116 and WO 92/07243). Alternatively, T cells may be derived from related or unrelated humans, non-human mammals, cell lines or cultures.

T cells may be stimulated with MTB32Mut-39F or MTB102F, a polynucleotide encoding MTB32Mut-39F or MTB102F, and/or an antigen presenting cell (APC) that presents an antigenic portion of MTB32Mut-39F or MTB102F. Such stimulation is performed under conditions and for a time sufficient to permit the generation of T cells that are specific for MTB32Mut-39F or MTB102F. Preferably, the MTB32Mut-39F or MTB102F or polynucleotide encoding MTB32Mut-39F or MTB102F is present within a delivery vehicle, such as a microsphere, to facilitate the generation of MTB32Mut-39F or MTB102F specific T cells.

T cells are considered to be specific for MTB32Mut-39F or MTB102F if the T cells specifically proliferate, secrete cytokines or kill target cells coated with MTB32Mut-39F or an immunogenic fragment thereof; or MTB102F or an immunogenic fragment thereof; or expressing a gene encoding MTB32Mut-39F or MTB102F. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (100 ng/ml-100 μg/ml, preferably 200 ng/ml-25 μg/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., *Current Protocols in Immunology*, vol. 1 (1998)). T cells that have been activated in response to a MTB32Mut-39F or MTB102F, polynucleotide encoding MTB32Mut-39F or MTB102F or MTB32Mut-39F or MTB102F presenting APC may be $CD4^+$ and/or $CD8^+$. MTB32Mut-39F or MTB102F specific T cells may be expanded using standard techniques. Within preferred embodiments, the T cells are derived from a patient, a related donor or an unrelated donor, and are administered to the patient following stimulation and expansion.

For therapeutic purposes, $CD4^+$ or $CD8^+$ T cells that proliferate in response to MTB32Mut-39F or MTB102F, a polynucleotide encoding MTB32Mut-39F or MTB102F or APC presenting antigenic peptides from MTB32Mut-39F or MTB102F can be expanded in number either in vitro or in vivo. Proliferation of such T cells in vitro may be accomplished in a variety of ways. For example, the T cells can be re-exposed to MTB32Mut-39F or MTB102F, or a short peptide corresponding to an immunogenic portion of such MTB32Mut-39F or MTB102F, with or without the addition of T cell growth factors, such as interleukin-2, and/or stimulator cells that synthesize the polypeptide. Alternatively, one or more T cells that proliferate in the presence of MTB32Mut-39F or MTB102F can be expanded in number by cloning. Methods for cloning cells are well known in the art, and include limiting dilution.

Pharmaceutical Compositions

In additional embodiments, the present invention concerns formulation of one or more of the polynucleotide, polypeptide, T-cell and/or antibody compositions disclosed herein in pharmaceutically-acceptable or physiologically-acceptable solutions for administration to a cell or an animal, either alone, or in combination with one or more other modalities of therapy. Such compositions are also useful for diagnostic uses.

It will also be understood that, if desired, the nucleic acid segment, RNA, DNA compositions that express a MTB32Mut-39F or MTB102F as disclosed herein may be administered in combination with other agents as well, such as, e.g., other proteins or polypeptides or various pharmaceutically-active agents. In fact, there is virtually no limit to other components that may also be included, given that the additional agents do not cause a significant adverse effect upon contact with the target cells or host tissues. The compositions may thus be delivered along with various other agents as required in the particular instance. Such compositions may be purified from host cells or other biological sources, or alternatively may be chemically synthesized as described herein. Likewise, such compositions may further comprise substituted or derivatized RNA or DNA compositions.

Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intramuscular administration and formulation.

1. Oral Delivery

In certain applications, the pharmaceutical compositions disclosed herein may be delivered via oral administration to an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (Mathiowitz et al., Nature. 1997Mar 27;386 (6623):410; Gupta SK Hwang et al., J Clin Pharmacol. 1998 January;38(1):60-7; U.S. Pat. Nos. 5,641,515 ; 5,580,579 and 5,792,451, each specifically incorporated herein by reference in its entirety). The tablets, troches, pills, capsules and the like may also contain the following: a binder, as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

2. Injectable Delivery

In certain circumstances it will be desirable to deliver the pharmaceutical compositions disclosed herein parenterally, intravenously, intramuscularly, or even intraperitoneally as described in U.S. Pat. Nos. 5,543,158; 5,641,515 and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., *Remington's Pharmaceutical Sciences,* 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

3. Nasal Delivery

In certain embodiments, the pharmaceutical compositions may be delivered by intranasal sprays, inhalation, and/or other aerosol delivery vehicles. Methods for delivering genes, nucleic acids, and peptide compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., J Control Release. 1998 Mar 2;52(1-2):81-7) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

4. Liposome-, Nanocapsule-, and Microparticle-Mediated Delivery

In certain embodiments, the inventors contemplate the use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, or a nanoparticle or the like.

Such formulations may be preferred for the introduction of pharmaceutically-acceptable formulations of the nucleic acids or constructs disclosed herein. The formation and use of liposomes is generally known to those of skill in the art (see for example, Couvreur et al., FEBS Lett. 1977 Dec 15;84(2): 323-6; Couvreur, Crit Rev Ther Drug Carrier Syst. 1988;5(1):1-20; Lasic, Trends Biotechnol. 1998 July;16(7):307-21; which describes the use of liposomes and nanocapsules in the targeted antibiotic therapy for intracellular bacterial infections and diseases). Recently, liposomes were developed with improved serum stability and circulation half-times (Gabizon & Papahadjopoulos, Proc Natl Acad Sci U S A. 1988 September;85(18):6949-53; Allen and Chonn, FEBS Lett. 1987 Oct. 19;223(1):42-6; U.S. Pat. No. 5,741,516, specifically incorporated herein by reference in its entirety). Further, various methods of liposome and liposome like preparations as potential drug carriers have been reviewed (Takakura, Nippon Rinsho, 1998 March;56 (3):691-5; Chandran et al., Indian J Exp Biol. 1997 August; 35(8):801-9; Margalit, Crit Rev Ther Drug Carrier Syst. 1995;12(2-3):233-61; U.S. Pat. Nos. 5,567,434; 5,552,157; 5,565,213; 5,738,868 and 5,795,587, each specifically incorporated herein by reference in its entirety).

Liposomes have been used successfully with a number of cell types that are normally resistant to transfection by other procedures including T cell suspensions, primary hepatocyte cultures and PC 12 cells (Renneisen et al., J Biol Chem. 1990 Sep 25;265(27):16337-42; Muller et al., Chem Phys Lipids. 1990 January;52(2):111-27). In addition, liposomes are free of the DNA length constraints that are typical of viral-based delivery systems. Liposomes have been used effectively to introduce genes, drugs (Heath & Martin, Chem Phys Lipids. 1986 June-July;40(2-4):347-58; Heath et al., Biochim Biophys Acta. 1986 Nov 6;862(1):72- 80; Balazsovits et al., 1989; Cancer Chemother Pharmacol. 1989;23(2):81-6; Fresta and& Puglisi, Biomaterials. 1996 April;17(8):751-8), radiotherapeutic agents (Pikul et al., Arch Surg. 1987 December;122(12):1417-20), enzymes (Imaizumi et al., Acta Neurochir Suppl (Wien). 1990;51:236-8; Imaizumi et al., Stroke. 1990 September;21(9):1312-7), viruses (Faller & Baltimore, J Virol. 1984 Januray;49(1):269-72), transcription factors and Allosteric effectors (Nicolau & Gersonde, Blut 1979 July;39 (1):1-7) into a variety of Cultured cell lines and animals. In addition, several successful clinical trails examining The effectiveness of lipsome-mediated drug delivery have been completed (Lopez-Berestein et al., J Infect Dis. 1985 April; 151(4):704-10; Lopez-Berestein et al., Cancer Drug Deliv. 1985 Summer;2(3):183-9; Coune, Infection. 1988 May-June; 16(3):141-7; Sculier et al., Eur J Cancer Clin Oncol. 1988 March;24(3):527-38). Furthermore, several studies suggest that the use of liposomes is not associated with autoimmune responses, toxicity or gonadal localization after systemic delivery (Mori & Fukatsu, Epilepsia. 1992 November-December;33(6):994-1000).

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Liposomes bear resemblance to cellular membranes and are contemplated for use in connection with the present invention as carriers for the peptide compositions. They are widely suitable as both water- and lipid-soluble substances can be entrapped, i.e. in the aqueous spaces and within the bilayer itself, respectively. It is possible that the drug-bearing liposomes may even be employed for site-specific delivery of active agents by selectively modifying the liposomal formulation.

In addition to the teachings of Couvreur et al. FEBS Lett. 1977 Dec 15;84(2):323-6; and Couvreur et al., Crit Rev Ther Drug Carrier Syst. 1988 ;5(1):1- 20, the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins, such as cytochrome c, bind, deform and penetrate the bilayer, thereby causing changes in permeability. Cholesterol inhibits this penetration of proteins, apparently by packing the phospholipids more tightly. It is contemplated that the most useful liposome formations for antibiotic and inhibitor delivery will contain cholesterol.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical properties of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity, and surface charge. They may persist in tissues for h or days, depending on their composition, and half lives in the blood range from min to several h. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow, and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types. Mostly, it is contemplated that intravenous injection of liposomal preparations would be used, but other routes of administration are also conceivable.

Alternatively, the invention provides for pharmaceutically-acceptable nanocapsule formulations of the compositions of the present invention. Nanocapsules can generally entrap compounds in a stable and reproducible way (Henry-Michelland et al., J Pharm Pharmacology. 1987 December;39(12): 973-7; Quintanar-Guerrero et al., Drug Dev Ind Pharm. 1998 December;24(12):1113-28; Douglas et al., Crit Rev Ther Drug Carrier Syst. 1987 ;3(3):233-61). To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention. Such particles may be are easily made, as described (Couvreur et al., 1980supra and 1988, supra; zur Muhlen et al., Eur J Pharm Biopharm. 1998 March;45(2):149-55; Zambaux et al. J Control Release. 1998 Jan 2;50(1-3):31-40; Pinto-Alphandry et al., 1995 J Drug Target. 1995;3(2):167-9 and U.S. Pat. No. 5,145,684, specifically incorporated herein by reference in its entirety).

Vaccines

In certain preferred embodiments of the present invention, vaccines are provided. The vaccines will generally comprise one or more pharmaceutical compositions, such as those discussed above, in combination with an immunostimulant. An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., *Vaccine Design* (the subunit and adjuvant approach) (1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

Illustrative vaccines may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143-198 (1998), and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317-321 (1989); Flexner et al., *Anna N.Y. Acad. Sci.* 569:86-103 (1989); Flexner et al., *Vaccine* 8:17-21 (1990); U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616-627 (1988); Rosenfeld et al., *Science* 252:431-434 (1991); Kolls et al., *Proc. Natl. Acad. Sci. USA* 91:215-219 (1994); Kass-Eisler et al., *Proc. Natl. Acad. Sci. USA* 90:11498-11502 (1993); Guzman et al., *Circulation* 88:2838-2848 (1993); and Guzman et al., *Cir. Res.* 73:1202-1207 (1993). Techniques for incorporating DNA into such expression systems are well known to those of ordinary skill in the art. The DNA may also be "naked," as described, for example, in Ulmer et al., *Science* 259:1745-1749 (1993) and reviewed by Cohen, *Science* 259:1691-1692 (1993). The uptake of naked DNA may be increased by coating the DNA onto biodegradable beads, which are efficiently transported into the cells. It will be apparent that a vaccine may comprise both a polynucleotide and a polypeptide component. Such vaccines may provide for an enhanced immune response.

It will be apparent that a vaccine may contain pharmaceutically acceptable salts of the polynucleotides and polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).

While any suitable carrier known to those of ordinary skill in the art may be employed in the vaccine compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268; 5,075,109; 5,928,647; 5,811,128; 5,820,883; 5,853,763; 5,814,344 and 5,942,252. One may also employ a carrier comprising the particulate-protein complexes described in U.S. Pat. No. 5,928,647, which are capable of inducing a class I-restricted cytotoxic T lymphocyte responses in a host.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium* species or *Mycobacterium* derived proteins. For example, delipidated, deglycolipidated *M. vaccae* ("pVac") can be used. In another embodiment, BCG is used as an adjuvant. In addition, the vaccine can be administered to a subject previously exposed to BCG. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); CWS, MPL, CpG, TDM, Leif, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann & Coffman, *Ann. Rev. Immunol.* 7:145-173 (1989).

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., *Science* 273:352 (1996). Another preferred adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other preferred formulations include more than one saponin in the adjuvant combinations of the present invention, for example combinations of at least two of the following group comprising QS21, QS7, Quil A, β-escin, or digitonin.

Alternatively the saponin formulations may be combined with vaccine vehicles composed of chitosan or other polycationic polymers, polylactide and polylactide-co-glycolide particles, poly-N-acetyl glucosamine-based polymer matrix, particles composed of polysaccharides or chemically modified polysaccharides, liposomes and lipid-based particles, particles composed of glycerol monoesters, etc. The saponins may also be formulated in the presence of cholesterol to form particulate structures such as liposomes or ISCOMs. Furthermore, the saponins may be formulated together with a polyoxyethylene ether or ester, in either a non-particulate solution or suspension, or in a particulate structure such as a paucilamelar liposome or ISCOM. The saponins may also be formulated with excipients such as Carbopol® to increase viscosity, or may be formulated in a dry powder form with a powder excipient such as lactose.

In one preferred embodiment, the adjuvant system includes the combination of a monophosphoryl lipid A and a saponin derivative, such as the combination of QS21 and 3D-MPL® adjuvant, as described in WO 94/00153, or a less reactogenic composition where the QS21 is quenched with cholesterol, as described in WO 96/33739. Other preferred formulations comprise an oil-in-water emulsion and tocopherol. Another particularly preferred adjuvant formulation employing QS21, 3D-MPL® adjuvant and tocopherol in an oil-in-water emulsion (optionally with squalene) is described in WO 95/17210. CpG is optionally a component of these adjuvant systems. See also EP 735898 B1.

Another enhanced adjuvant system involves the combination of a CpG-containing oligonucleotide and a saponin derivative particularly the combination of CpG and QS21 as disclosed in WO 00/09159. Preferably the formulation additionally comprises an oil in water emulsion (optionally using squalene) and tocopherol.

Other preferred adjuvants include Montanide ISA 720 (Seppic, France), SAF (Chiron, Calif., United States), ISCOMS (CSL), MF-59 (Chiron), Detox (Corixa, Hamilton, Mont.), RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

Other preferred adjuvants include adjuvant molecules of the general formula (I): $HO(CH_2CH_2O)_n$-A-R, wherein, n is 1-50, A is a bond or —C(O)—, R is $C_{1-50}$ alkyl or phenyl $C_{1-50}$ alkyl.

One embodiment of the present invention consists of a vaccine formulation comprising a polyoxyethylene ether of general formula (I), wherein n is between 1 and 50, preferably 4-24, most preferably 9; the R component is $C_{1-50}$, preferably $C_4$-$C_{20}$ alkyl and most preferably $C_{1-2}$ alkyl, and A is a bond. The concentration of the polyoxyethylene ethers should be in the range 0.1-20%, preferably from 0.1-10%, and most preferably in the range 0.1-1%. Preferred polyoxyethylene ethers are selected from the following group: polyoxyethylene-9-lauryl ether, polyoxyethylene-9-steoryl ether, polyoxyethylene-8-steoryl ether, polyoxyethylene-4-lauryl ether, polyoxyethylene-35-lauryl ether, and polyoxyethylene-23-lauryl ether. Polyoxyethylene ethers such as polyoxyethylene lauryl ether are described in the Merck index ($12^{th}$ edition: entry 7717). These adjuvant molecules are described in WO 99/52549.

The polyoxyethylene ether according to the general formula (I) above may, if desired, be combined with another adjuvant. For example, a preferred adjuvant combination is preferably with CpG as described in the pending UK patent application GB 9820956.2.

Any vaccine provided herein may be prepared using well known methods that result in a combination of antigen, immune response enhancer and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429-1438 (1996)) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Vaccines can be administered in a prime and boost combination, e.g., priming with a nucleic acid encoding a fusion protein of the invention and then later boosting with a dose of the fusion protein, or alternatively priming with a fusion protein of the invention and then later boosting with a dose of the nucleic acid encoding the fusion protein.

Carriers for use within such formulations are biocompatible, and may also be biodegradable; preferably the formulation provides a relatively constant level of active component release. Such carriers include microparticles of poly(lactide-co-glycolide), polyacrylate, latex, starch, cellulose, dextran and the like. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see, e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of a MTB32Mut-39F or MTB102F-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau & Steinman, *Nature* 392:245-251 (1998)) and have been shown to be effective as a physiological adjuvant for eliciting prophylactic or therapeutic antitumor immunity (see Timmerman & Levy, *Ann. Rev. Med.* 50:507-529 (1999)). In general, dendritic cells may be identified based on their typical shape (stellate in situ, with marked cytoplasmic processes (dendrites) visible in vitro), their ability to take up, process and present antigens with high efficiency and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594-600 (1998)).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding MTB32Mut-39F or MTB102F (or portion or other variant thereof) such that the MTB32Mut-39F or an immunogenic fragment thereof; or MTB102F or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and Cell Biology* 75:456-460 (1997). Antigen loading of dendritic cells may be achieved by incubating dendritic cells or progenitor cells with MTB32Mut-39F or MTB102F, DNA (naked or within a plasmid vector) or RNA; or with antigen-expressing recombinant bacterium or viruses (e.g., vaccinia, fowlpox, adenovirus or lentivirus vectors). Prior to loading, MTB32Mut-39F or MTB102F may be covalently conjugated to an immunological partner that provides T cell help (e.g., a carrier molecule). Alternatively, a dendritic cell may be pulsed with a non-conjugated immunological partner, separately or in the presence of MTB32Mut-39F or MTB102F.

Vaccines and pharmaceutical compositions may be presented in unit-dose or multi-dose containers, such as sealed ampoules or vials. Such containers are preferably hermetically sealed to preserve sterility of the formulation until use. In general, formulations may be stored as suspensions, solutions or emulsions in oily or aqueous vehicles. Alternatively, a vaccine or pharmaceutical composition may be stored in a freeze-dried condition requiring only the addition of a sterile liquid carrier immediately prior to use.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridizes to a polynucleotide encoding a protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein of the invention.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Construction of Vector for MTB32MutSA-MTB39F and MTB102F Fusion Polypeptides Expression of the full-length sequences of the mature or full length, secreted form of Ra35 (MTB32A) in *E. coli* has been difficult. The expressed product was only visible after immunoblotting with a polyclonal rabbit anti-Ra35 antibody indicative of low levels of protein expression. Even then, multiple specific species (bands) were detected indicative of auto-catalytic breakdown (degradation) of the recombinant antigen. This result was presumed to be due to the expression of Ra35FL in *E. coli* as a biologically active form.

It has been previously shown that it was possible to express Ra35FL as two overlapping halves comprising the N-terminal (Ra35N-term, called Ra35) and C-term halves (Ra35C-term called Ra12). To enhance and stabilize the expression of the whole Ra35 molecule, a single point mutation was introduced at one of the residues within the active-site triad (T to G, resulting in substitution of Ser to Ala). This mutagenized form of MTB32A can now be easily expressed at high levels in a stable form.

To increase fusion protein expression level, techniques well known in the art were used to generate a fusion protein, mutated MTB32-39F, including both MTB32MutSA and MTB39. MTB32-39F is 723 amino acid polypeptide which includes amino acids 1-330 from Ra35FLMutSA and amino acids 1-391 of MTB39. MTB32MutSA-39F is stable, is expressed at high levels, and is highly immunogenic in animal studies.

Example 2

MTB102F

MTB102F was created by adding a third antigen, MTB 85B, to the C terminus of MTB32MutSA-MTB39F. MTB85B is a 287 amino acid sequence derived from *Mycobacterium bovis* (see, e.g., Content et al., *Infect. & Immunol.* 59:3205-3212 (1991)).

What is claimed is:

1. A method for prophylaxis against *Mycobacterium tuberculosis* comprising administering an effective amount of a polynucleotide, which comprises a nucleic acid sequence encoding a fusion protein having at least 95% identity to the amino acid sequence of SEQ ID NO:16 or SEQ ID NO:18.

2. The method of claim 1, wherein the polynucleotide comprises a nucleic acid sequence encoding a fusion protein having at least 95% identity to the amino acid sequence of SEQ ID NO:16.

3. The method of claim 1, wherein the polynucleotide comprises a nucleic acid sequence encoding a fusion protein having at least 95% identity to the amino acid sequence of SEQ ID NO:18.

4. The method of claim 1, wherein the polynucleotide comprises a nucleic acid sequence encoding a fusion protein consisting of:(i) residues 8 to 1154 of SEQ ID NO:16; or(ii) residues 8 to 1016 of SEQ ID NO:18.

5. The method of claim 4, wherein the polynucleotide encodes a fusion protein consisting of residues 8 to 1154 of SEQ ID NO:16.

6. The method of claim 4, wherein the polynucleotide encodes a fusion protein consisting of residues 8 to 1016 of SEQ ID NO:18.

7. The method of claim 1, wherein the polynucleotide is administered in a composition comprising a physiologically acceptable carrier.

8. The method of claim 7, wherein the composition further comprises an immunostimulant.

9. The method of claim 8, wherein the immunostimulant is an adjuvant.

10. The method of claim 9, wherein the adjuvant is a combination of QS21 and 3D-MPL.

11. A method for eliciting an immune response in a subject, comprising administering to the subject an effective amount of a polynucleotide, which comprises a nucleic acid sequence encoding a fusion protein having at least 95% identity to the amino acid sequence of SEQ ID NO:16 or SEQ ID NO:18.

* * * * *

SEQUENCE LISTING

```
<160> NUMBER OF SEQ ID NOS: 22

<210> SEQ ID NO 1
<211> LENGTH: 2181
<212> TYPE: DNA
<213> ORGANISM: Artificial Sequence
<220> FEATURE:
<223> OTHER INFORMATION: Description of Artificial Sequence:mutated
      MTB32-MTB39F fusion protein (MTB32MutSA)

<400> SEQUENCE: 1
```

-continued

```
catatgcatc accatcacca tcacgccccg ccggccttgt cgcaggaccg gttcgccgac      60
ttccccgcgc tgcccctcga cccgtccgcg atggtcgccc aagtggggcc acaggtggtc     120
aacatcaaca ccaaactggg ctacaacaac gccgtgggcg ccgggaccgg catcgtcatc     180
gatcccaacg gtgtcgtgct gaccaacaac cacgtgatcg cgggcgccac cgacatcaat     240
gcgttcagcg tcggctccgg ccaaacctac ggcgtcgatg tggtcgggta tgaccgcacc     300
caggatgtcg cggtgctgca gctgcgcggt gccggtggcc tgccgtcggc ggcgatcggt     360
ggcggcgtcg cggttggtga gcccgtcgtc gcgatgggca acagcggtgg gcagggcgga     420
acgccccgtg cggtgcctgg cagggtggtc gcgctcggcc aaaccgtgca ggcgtcggat     480
tcgctgaccg gtgccgaaga gacattgaac gggttgatcc agttcgatgc cgcgatccag     540
cccggtgatg cgggcgggcc cgtcgtcaac ggcctaggac aggtggtcgg tatgaacacg     600
gccgcgtccg ataacttcca gctgtcccag ggtgggcagg gattcgccat tccgatcggg     660
caggcgatgg cgatcgcggg ccagatccga tcgggtgggg ggtcacccac cgttcatatc     720
gggcctaccg ccttcctcgg cttgggtgtt gtcgacaaca acggcaacgg cgcacgagtc     780
caacgcgtgg tcgggagcgc tccggcggca agtctcggca tctccaccgg cgacgtgatc     840
accgcggtcg acggcgctcc gatcaactcg gccaccgcga tggcggacgc gcttaacggg     900
catcatcccg gtgacgtcat ctcggtgacc tggcaaacca agtcgggcgg cacgcgtaca     960
gggaacgtga cattggccga gggacccccg gccgaattca tggtggattt cggggcgtta    1020
ccaccggaga tcaactccgc gaggatgtac gccggcccgg gttcggcctc gctggtggcc    1080
gcggctcaga tgtgggacag cgtggcgagt gacctgtttt cggccgcgtc ggcgtttcag    1140
tcggtggtct ggggtctgac ggtggggtcg tggataggtt cgtcggcggg tctgatggtg    1200
gcggcggcct cgccgtatgt ggcgtggatg agcgtcaccg cggggcaggc cgagctgacc    1260
gccgcccagg tccgggttgc tgcggcggcc tacgagacgg cgtatgggct gacggtgccc    1320
ccgccggtga tcgccgagaa ccgtgctgaa ctgatgattc tgatagcgac caacctcttg    1380
gggcaaaaca ccccggcgat cgcggtcaac gaggccgaat acggcgagat gtgggcccaa    1440
gacgccgccg cgatgtttgg ctacgccgcg gcgacggcga cggcgacggc gacgttgctg    1500
ccgttcgagg aggcgccgga gatgaccagc gcgggtgggc tcctcgagca ggccgccgcg    1560
gtcgaggagg cctccgacac cgccgcggcg aaccagttga tgaacaatgt gccccaggcg    1620
ctgcaacagc tggcccagcc cacgcagggc accacgcctt cttccaagct gggtggcctg    1680
tggaagacgg tctcgccgca tcggtcgccg atcagcaaca tggtgtcgat ggccaacaac    1740
cacatgtcga tgaccaactc gggtgtgtcg atgaccaaca ccttgagctc gatgttgaag    1800
ggctttgctc cggcggcggc cgcccaggcc gtgcaaaccg cggcgcaaaa cggggtccgg    1860
gcgatgagct cgctgggcag ctcgctgggt tcttcgggtc tgggcggtgg ggtggccgcc    1920
aacttgggtc gggcggcctc ggtcggttcg ttgtcggtgc cgcaggcctg ggccgcggcc    1980
aaccaggcag tcaccccggc ggcgcgggcg ctgccgctga ccagcctgac cagcgccgcg    2040
gaaagagggc ccgggcagat gctgggcggg ctgccggtgg ggcagatggg cgccagggcc    2100
ggtggtgggc tcagtggtgt gctgcgtgtt ccaccgcgac cctatgtgat gccgcattct    2160
ccggcagccg gctaaggatc c                                              2181
```

<210> SEQ ID NO 2
<211> LENGTH: 723
<212> TYPE: PRT
<213> ORGANISM: Artificial Sequence
<220> FEATURE:

-continued

<223> OTHER INFORMATION: Description of Artificial Sequence:mutated MTB32-MTB39F fusion protein (MTB32MutSA)

<400> SEQUENCE: 2

```
Met His His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
             20                  25                  30

Gln Val Gly Pro Gln Val Val Asn Ile Asn Thr Lys Leu Gly Tyr Asn
         35                  40                  45

Asn Ala Val Gly Ala Gly Thr Gly Ile Val Ile Asp Pro Asn Gly Val
     50                  55                  60

Val Leu Thr Asn Asn His Val Ile Ala Gly Ala Thr Asp Ile Asn Ala
 65                  70                  75                  80

Phe Ser Val Gly Ser Gly Gln Thr Tyr Gly Val Asp Val Val Gly Tyr
                 85                  90                  95

Asp Arg Thr Gln Asp Val Ala Val Leu Gln Leu Arg Gly Ala Gly Gly
            100                 105                 110

Leu Pro Ser Ala Ala Ile Gly Gly Gly Val Ala Val Gly Glu Pro Val
        115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ala Gly Gly Pro Val Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255

Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285

Ser Ala Thr Ala Met Ala Asp Ala Leu Asn Gly His His Pro Gly Asp
    290                 295                 300

Val Ile Ser Val Thr Trp Gln Thr Lys Ser Gly Gly Thr Arg Thr Gly
305                 310                 315                 320

Asn Val Thr Leu Ala Glu Gly Pro Pro Ala Glu Phe Met Val Asp Phe
                325                 330                 335

Gly Ala Leu Pro Pro Glu Ile Asn Ser Ala Arg Met Tyr Ala Gly Pro
            340                 345                 350

Gly Ser Ala Ser Leu Val Ala Ala Ala Gln Met Trp Asp Ser Val Ala
        355                 360                 365

Ser Asp Leu Phe Ser Ala Ala Ser Ala Phe Gln Ser Val Val Trp Gly
    370                 375                 380

Leu Thr Val Gly Ser Trp Ile Gly Ser Ser Ala Gly Leu Met Val Ala
385                 390                 395                 400
```

-continued

```
Ala Ala Ser Pro Tyr Val Ala Trp Met Ser Val Thr Ala Gly Gln Ala
                405                 410                 415

Glu Leu Thr Ala Ala Gln Val Arg Val Ala Ala Ala Ala Tyr Glu Thr
            420                 425                 430

Ala Tyr Gly Leu Thr Val Pro Pro Pro Val Ile Ala Glu Asn Arg Ala
        435                 440                 445

Glu Leu Met Ile Leu Ile Ala Thr Asn Leu Leu Gly Gln Asn Thr Pro
    450                 455                 460

Ala Ile Ala Val Asn Glu Ala Glu Tyr Gly Glu Met Trp Ala Gln Asp
465                 470                 475                 480

Ala Ala Ala Met Phe Gly Tyr Ala Ala Ala Thr Ala Thr Ala Thr Ala
                485                 490                 495

Thr Leu Leu Pro Phe Glu Glu Ala Pro Glu Met Thr Ser Ala Gly Gly
            500                 505                 510

Leu Leu Glu Gln Ala Ala Ala Val Glu Glu Ala Ser Asp Thr Ala Ala
        515                 520                 525

Ala Asn Gln Leu Met Asn Asn Val Pro Gln Ala Leu Gln Gln Leu Ala
    530                 535                 540

Gln Pro Thr Gln Gly Thr Thr Pro Ser Ser Lys Leu Gly Gly Leu Trp
545                 550                 555                 560

Lys Thr Val Ser Pro His Arg Ser Pro Ile Ser Asn Met Val Ser Met
                565                 570                 575

Ala Asn Asn His Met Ser Met Thr Asn Ser Gly Val Ser Met Thr Asn
            580                 585                 590

Thr Leu Ser Ser Met Leu Lys Gly Phe Ala Pro Ala Ala Ala Ala Gln
        595                 600                 605

Ala Val Gln Thr Ala Ala Gln Asn Gly Val Arg Ala Met Ser Ser Leu
    610                 615                 620

Gly Ser Ser Leu Gly Ser Ser Gly Leu Gly Gly Gly Val Ala Ala Asn
625                 630                 635                 640

Leu Gly Arg Ala Ala Ser Val Gly Ser Leu Ser Val Pro Gln Ala Trp
                645                 650                 655

Ala Ala Ala Asn Gln Ala Val Thr Pro Ala Ala Arg Ala Leu Pro Leu
            660                 665                 670

Thr Ser Leu Thr Ser Ala Ala Glu Arg Gly Pro Gly Gln Met Leu Gly
        675                 680                 685

Gly Leu Pro Val Gly Gln Met Gly Ala Arg Ala Gly Gly Gly Leu Ser
    690                 695                 700

Gly Val Leu Arg Val Pro Pro Arg Pro Tyr Val Met Pro His Ser Pro
705                 710                 715                 720

Ala Ala Gly
```

<210> SEQ ID NO 3
<211> LENGTH: 3030
<212> TYPE: DNA
<213> ORGANISM: Artificial Sequence
<220> FEATURE:
<223> OTHER INFORMATION: Description of Artificial Sequence:MTB-102F
      fusion protein

<400> SEQUENCE: 3

```
atgcatcacc atcaccatca cgccccgccg gccttgtcgc aggaccggtt cgccgacttc      60

cccgcgctgc ccctcgaccc gtccgcgatg gtcgcccaag tggggccaca ggtggtcaac     120

atcaacacca aactgggcta caacaacgcc gtgggcgccg ggaccggcat cgtcatcgat     180

cccaacggtg tcgtgctgac caacaaccac gtgatcgcgg gcgccaccga catcaatgcg     240
```

-continued

```
ttcagcgtcg gctccggcca aacctacggc gtcgatgtgg tcgggtatga ccgcacccag    300
gatgtcgcgg tgctgcagct gcgcggtgcc ggtggcctgc cgtcggcggc gatcggtggc    360
ggcgtcgcgg ttggtgagcc cgtcgtcgcg atgggcaaca gcggtgggca gggcggaacg    420
ccccgtgcgg tgcctggcag ggtggtcgcg ctcggccaaa ccgtgcaggc gtcggattcg    480
ctgaccggtg ccgaagagac attgaacggg ttgatccagt tcgatgccgc gatccagccc    540
ggtgatgcgg gcgggcccgt cgtcaacggc ctaggacagg tggtcggtat gaacacggcc    600
gcgtccgata acttccagct gtcccagggt gggcagggat tcgccattcc gatcgggcag    660
gcgatggcga tcgcgggcca gatccgatcg ggtggggggt cacccaccgt tcatatcggg    720
cctaccgcct tcctcggctt gggtgttgtc gacaacaacg gcaacggcgc acgagtccaa    780
cgcgtggtcg ggagcgctcc ggcggcaagt ctcggcatct ccaccggcga cgtgatcacc    840
gcggtcgacg gcgctccgat caactcggcc accgcgatgg cggacgcgct taacgggcat    900
catcccggtg acgtcatctc ggtgacctgg caaaccaagt cgggcggcac gcgtacaggg    960
aacgtgacat tggccgaggg acccccggcc gaattcatgg tggatttcgg ggcgttacca   1020
ccggagatca actccgcgag gatgtacgcc ggcccgggtt cggcctcgct ggtggccgcg   1080
gctcagatgt gggacagcgt ggcgagtgac ctgttttcgg ccgcgtcggc gtttcagtcg   1140
gtggtctggg gtctgacggt ggggtcgtgg ataggttcgt cggcgggtct gatggtggcg   1200
gcggcctcgc cgtatgtggc gtggatgagc gtcaccgcgg ggcaggccga gctgaccgcc   1260
gcccaggtcc gggttgctgc ggcggcctac gagacggcgt atgggctgac ggtgcccccg   1320
ccggtgatcg ccgagaaccg tgctgaactg atgattctga tagcgaccaa cctcttgggg   1380
caaaacaccc cggcgatcgc ggtcaacgag gccgaatacg gcgagatgtg ggcccaagac   1440
gccgccgcga tgtttggcta cgccgcggcg acggcgacgg cgacggcgac gttgctgccg   1500
ttcgaggagg cgccggagat gaccagcgcg ggtgggctcc tcgagcaggc cgccgcggtc   1560
gaggaggcct ccgacaccgc cgcggcgaac cagttgatga acaatgtgcc ccaggcgctg   1620
caacagctgg cccagcccac gcagggcacc acgccttctt ccaagctggg tggcctgtgg   1680
aagacggtct cgccgcatcg gtcgccgatc agcaacatgg tgtcgatggc caacaaccac   1740
atgtcgatga ccaactcggg tgtgtcgatg accaacacct tgagctcgat gttgaagggc   1800
tttgctccgg cggcggccgc ccaggccgtg caaaccgcgg cgcaaaacgg ggtccgggcg   1860
atgagctcgc tgggcagctc gctgggttct tcgggtctgg gcggtggggt ggccgccaac   1920
ttgggtcggg cggcctcggt cggttcgttg tcggtgccgc aggcctgggc cgcggccaac   1980
caggcagtca ccccggcggc gcgggcgctg ccgctgacca gcctgaccag cgccgcggaa   2040
agagggcccg ggcagatgct gggcgggctg ccggtggggc agatgggcgc cagggccggt   2100
ggtgggctca gtggtgtgct gcgtgttccg ccgcgaccct atgtgatgcc gcattctccg   2160
gcagccggca agcttttctc ccggccgggg ctgccggtcg agtacctgca ggtgccgtcg   2220
ccgtcgatgg gccgcgacat caaggttcag ttccagagcg gtgggaacaa ctcacctgcg   2280
gtttatctgc tcgacggcct gcgcgcccaa gacgactaca acggctggga tatcaacacc   2340
ccggcgttcg agtggtacta ccagtcggga ctgtcgatag tcatgccggt cggcgggcag   2400
tccagcttct acagcgactg gtacagcccg gcctgcggta aggctggctg ccagacttac   2460
aagtgggaaa ccttcctgac cagcgagctg ccgcaatggt tgtccgccaa cagggccgtg   2520
aagcccaccg gcagcgctgc aatcggcttg tcgatggccg gctcgtcggc aatgatcttg   2580
gccgcctacc atccccagca gttcatctac gccggctcgc tgtcggccct gctggacccc   2640
```

```
tctcagggga tggggcctag cctgatcggc ctcgcgatgg gtgacgccgg cggttacaag   2700

gccgcagaca tgtggggtcc ctcgagtgac ccggcatggg agcgcaacga ccctacgcag   2760

cagatcccca agctggtcgc aaacaacacc cggctatggg tttattgcgg gaacggcacc   2820

ccgaacgagt tgggcggtgc caacataccc gccgagttct tggagaactt cgttcgtagc   2880

agcaacctga agttccagga tgcgtacaac gccgcgggcg ggcacaacgc cgtgttcaac   2940

ttcccgccca acggcacgca cagctgggag tactggggcg ctcagctcaa cgccatgaag   3000

ggtgacctgc agagttcgtt aggcgccggc                                    3030


<210> SEQ ID NO 4
<211> LENGTH: 1010
<212> TYPE: PRT
<213> ORGANISM: Artificial Sequence
<220> FEATURE:
<223> OTHER INFORMATION: Description of Artificial Sequence:MTB-102F
      fusion protein

<400> SEQUENCE: 4

Met His His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
             20                  25                  30

Gln Val Gly Pro Gln Val Val Asn Ile Asn Thr Lys Leu Gly Tyr Asn
         35                  40                  45

Asn Ala Val Gly Ala Gly Thr Gly Ile Val Ile Asp Pro Asn Gly Val
     50                  55                  60

Val Leu Thr Asn Asn His Val Ile Ala Gly Ala Thr Asp Ile Asn Ala
 65                  70                  75                  80

Phe Ser Val Gly Ser Gly Gln Thr Tyr Gly Val Asp Val Val Gly Tyr
                 85                  90                  95

Asp Arg Thr Gln Asp Val Ala Val Leu Gln Leu Arg Gly Ala Gly Gly
            100                 105                 110

Leu Pro Ser Ala Ala Ile Gly Gly Gly Val Ala Val Gly Glu Pro Val
        115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ala Gly Gly Pro Val Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255

Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285
```

-continued

Ser Ala Thr Ala Met Ala Asp Ala Leu Asn Gly His His Pro Gly Asp
    290                 295                 300

Val Ile Ser Val Thr Trp Gln Thr Lys Ser Gly Gly Thr Arg Thr Gly
305                 310                 315                 320

Asn Val Thr Leu Ala Glu Gly Pro Pro Ala Glu Phe Met Val Asp Phe
                325                 330                 335

Gly Ala Leu Pro Pro Glu Ile Asn Ser Ala Arg Met Tyr Ala Gly Pro
            340                 345                 350

Gly Ser Ala Ser Leu Val Ala Ala Ala Gln Met Trp Asp Ser Val Ala
        355                 360                 365

Ser Asp Leu Phe Ser Ala Ala Ser Ala Phe Gln Ser Val Val Trp Gly
    370                 375                 380

Leu Thr Val Gly Ser Trp Ile Gly Ser Ser Ala Gly Leu Met Val Ala
385                 390                 395                 400

Ala Ala Ser Pro Tyr Val Ala Trp Met Ser Val Thr Ala Gly Gln Ala
                405                 410                 415

Glu Leu Thr Ala Ala Gln Val Arg Val Ala Ala Ala Ala Tyr Glu Thr
            420                 425                 430

Ala Tyr Gly Leu Thr Val Pro Pro Pro Val Ile Ala Glu Asn Arg Ala
        435                 440                 445

Glu Leu Met Ile Leu Ile Ala Thr Asn Leu Leu Gly Gln Asn Thr Pro
    450                 455                 460

Ala Ile Ala Val Asn Glu Ala Glu Tyr Gly Glu Met Trp Ala Gln Asp
465                 470                 475                 480

Ala Ala Ala Met Phe Gly Tyr Ala Ala Ala Thr Ala Thr Ala Thr Ala
                485                 490                 495

Thr Leu Leu Pro Phe Glu Glu Ala Pro Glu Met Thr Ser Ala Gly Gly
            500                 505                 510

Leu Leu Glu Gln Ala Ala Ala Val Glu Glu Ala Ser Asp Thr Ala Ala
        515                 520                 525

Ala Asn Gln Leu Met Asn Asn Val Pro Gln Ala Leu Gln Gln Leu Ala
    530                 535                 540

Gln Pro Thr Gln Gly Thr Thr Pro Ser Ser Lys Leu Gly Gly Leu Trp
545                 550                 555                 560

Lys Thr Val Ser Pro His Arg Ser Pro Ile Ser Asn Met Val Ser Met
                565                 570                 575

Ala Asn Asn His Met Ser Met Thr Asn Ser Gly Val Ser Met Thr Asn
            580                 585                 590

Thr Leu Ser Ser Met Leu Lys Gly Phe Ala Pro Ala Ala Ala Ala Gln
        595                 600                 605

Ala Val Gln Thr Ala Ala Gln Asn Gly Val Arg Ala Met Ser Ser Leu
    610                 615                 620

Gly Ser Ser Leu Gly Ser Ser Gly Leu Gly Gly Gly Val Ala Ala Asn
625                 630                 635                 640

Leu Gly Arg Ala Ala Ser Val Gly Ser Leu Ser Val Pro Gln Ala Trp
                645                 650                 655

Ala Ala Ala Asn Gln Ala Val Thr Pro Ala Ala Arg Ala Leu Pro Leu
            660                 665                 670

Thr Ser Leu Thr Ser Ala Ala Glu Arg Gly Pro Gly Gln Met Leu Gly
        675                 680                 685

Gly Leu Pro Val Gly Gln Met Gly Ala Arg Ala Gly Gly Gly Leu Ser
    690                 695                 700

Gly Val Leu Arg Val Pro Pro Arg Pro Tyr Val Met Pro His Ser Pro
705                 710                 715                 720

```
Ala Ala Gly Lys Leu Phe Ser Arg Pro Gly Leu Pro Val Glu Tyr Leu
                725                 730                 735

Gln Val Pro Ser Pro Ser Met Gly Arg Asp Ile Lys Val Gln Phe Gln
            740                 745                 750

Ser Gly Gly Asn Asn Ser Pro Ala Val Tyr Leu Leu Asp Gly Leu Arg
        755                 760                 765

Ala Gln Asp Asp Tyr Asn Gly Trp Asp Ile Asn Thr Pro Ala Phe Glu
    770                 775                 780

Trp Tyr Tyr Gln Ser Gly Leu Ser Ile Val Met Pro Val Gly Gly Gln
785                 790                 795                 800

Ser Ser Phe Tyr Ser Asp Trp Tyr Ser Pro Ala Cys Gly Lys Ala Gly
                805                 810                 815

Cys Gln Thr Tyr Lys Trp Glu Thr Phe Leu Thr Ser Glu Leu Pro Gln
            820                 825                 830

Trp Leu Ser Ala Asn Arg Ala Val Lys Pro Thr Gly Ser Ala Ala Ile
        835                 840                 845

Gly Leu Ser Met Ala Gly Ser Ser Ala Met Ile Leu Ala Ala Tyr His
    850                 855                 860

Pro Gln Gln Phe Ile Tyr Ala Gly Ser Leu Ser Ala Leu Leu Asp Pro
865                 870                 875                 880

Ser Gln Gly Met Gly Pro Ser Leu Ile Gly Leu Ala Met Gly Asp Ala
                885                 890                 895

Gly Gly Tyr Lys Ala Ala Asp Met Trp Gly Pro Ser Ser Asp Pro Ala
            900                 905                 910

Trp Glu Arg Asn Asp Pro Thr Gln Gln Ile Pro Lys Leu Val Ala Asn
        915                 920                 925

Asn Thr Arg Leu Trp Val Tyr Cys Gly Asn Gly Thr Pro Asn Glu Leu
    930                 935                 940

Gly Gly Ala Asn Ile Pro Ala Glu Phe Leu Glu Asn Phe Val Arg Ser
945                 950                 955                 960

Ser Asn Leu Lys Phe Gln Asp Ala Tyr Asn Ala Ala Gly Gly His Asn
                965                 970                 975

Ala Val Phe Asn Phe Pro Pro Asn Gly Thr His Ser Trp Glu Tyr Trp
            980                 985                 990

Gly Ala Gln Leu Asn Ala Met Lys Gly Asp Leu Gln Ser Ser Leu Gly
        995                 1000                1005

Ala Gly
   1010
```

<210> SEQ ID NO 5
<211> LENGTH: 2808
<212> TYPE: DNA
<213> ORGANISM: Artificial Sequence
<220> FEATURE:
<223> OTHER INFORMATION: Description of Artificial Sequence:fusion protein R95F (MTB72F-MAPS)

<400> SEQUENCE: 5

```
catatgcatc accatcacca tcacacggcc gcgtccgata acttccagct gtcccagggt      60

gggcagggat tcgccattcc gatcgggcag gcgatggcga tcgcgggcca gatccgatcg     120

ggtggggggt cacccaccgt tcatatcggg cctaccgcct tcctcggctt gggtgttgtc     180

gacaacaacg gcaacggcgc acgagtccaa cgcgtggtcg ggagcgctcc ggcggcaagt     240

ctcggcatct ccaccggcga cgtgatcacc gcggtcgacg gcgctccgat caactcggcc     300

accgcgatgg cggacgcgct taacgggcat catcccggtg acgtcatctc ggtgacctgg     360
```

-continued

```
caaaccaagt cgggcggcac gcgtacaggg aacgtgacat tggccgaggg acccccggcc    420
gaattcatgg tggatttcgg ggcgttacca ccggagatca actccgcgag gatgtacgcc    480
ggcccgggtt cggcctcgct ggtggccgcg gctcagatgt gggacagcgt ggcgagtgac    540
ctgttttcgg ccgcgtcggc gtttcagtcg gtggtctggg gtctgacggt ggggtcgtgg    600
ataggttcgt cggcgggtct gatggtggcg gcggcctcgc cgtatgtggc gtggatgagc    660
gtcaccgcgg ggcaggccga gctgaccgcc gcccaggtcc gggttgctgc ggcggcctac    720
gagacggcgt atgggctgac ggtgcccccg ccggtgatcg ccgagaaccg tgctgaactg    780
atgattctga tagcgaccaa cctcttgggg caaaacaccc cggcgatcgc ggtcaacgag    840
gccgaatacg gcgagatgtg ggcccaagac gccgccgcga tgtttggcta cgccgcggcg    900
acggcgacgg cgacggcgac gttgctgccg ttcgaggagg cgccggagat gaccagcgcg    960
ggtgggctcc tcgagcaggc cgccgcggtc gaggaggcct ccgacaccgc cgcggcgaac   1020
cagttgatga acaatgtgcc ccaggcgctg caacagctgg cccagcccac gcagggcacc   1080
acgccttctt ccaagctggg tggcctgtgg aagacggtct cgccgcatcg gtcgccgatc   1140
agcaacatgg tgtcgatggc caacaaccac atgtcgatga ccaactcggg tgtgtcgatg   1200
accaacacct tgagctcgat gttgaagggc tttgctccgg cggcggccgc ccaggccgtg   1260
caaaccgcgg cgcaaaacgg ggtccgggcg atgagctcgc tgggcagctc gctgggttct   1320
tcgggtctgg gcggtggggt ggccgccaac ttgggtcggg cggcctcggt cggttcgttg   1380
tcggtgccgc aggcctgggc cgcggccaac caggcagtca ccccggcggc gcgggcgctg   1440
ccgctgacca gcctgaccag cgccgcggaa agagggcccg ggcagatgct gggcgggctg   1500
ccggtggggc agatgggcgc cagggccggt ggtgggctca gtggtgtgct gcgtgttccg   1560
ccgcgaccct atgtgatgcc gcattctccg gcagccggcg atatcgcccc gccggccttg   1620
tcgcaggacc ggttcgccga cttccccgcg ctgcccctcg acccgtccgc gatggtcgcc   1680
caagtggggc cacaggtggt caacatcaac accaaactgg gctacaacaa cgccgtgggc   1740
gccgggaccg gcatcgtcat cgatcccaac ggtgtcgtgc tgaccaacaa ccacgtgatc   1800
gcgggcgcca ccgacatcaa tgcgttcagc gtcggctccg gccaaaccta cggcgtcgat   1860
gtggtcgggt atgaccgcac ccaggatgtc gcggtgctgc agctgcgcgg tgccggtggc   1920
ctgccgtcgg cggcgatcgg tggcggcgtc gcggttggtg agcccgtcgt cgcgatgggc   1980
aacagcggtg ggcagggcgg aacgccccgt gcggtgcctg gcagggtggt cgcgctcggc   2040
caaaccgtgc aggcgtcgga ttcgctgacc ggtgccgaag agacattgaa cgggttgatc   2100
cagttcgatg ccgcgatcca gcccggtgat tcgggcgggc ccgtcgtcaa cggcctagga   2160
caggtggtcg gtatgaacac ggccgcgtcc ggtaccatgt cctgcggtaa cgccaagatc   2220
aactctcccg cgccgtcctt cgaggaggtg gcgctcatgc ccaacggcag cttcaagaag   2280
atcagcctct cctcctacaa gggcaagtgg gtcgtgctct tcttctaccc gctcgacttc   2340
accttcgtgt gcccgacaga ggtcatcgcg ttctccgaca gcgtgagtcg cttcaacgag   2400
ctcaactgcg aggtcctcgc gtgctcgata gacagcgagt acgcgcacct gcagtggacg   2460
ctgcaggacc gcaagaaggg cggcctcggg accatggcga tcccaatgct agccgacaag   2520
accaagagca tcgctcgttc ctacggcgtg ctggaggaga gccagggcgt ggcctaccgc   2580
ggtctcttca tcatcgaccc ccatggcatg ctgcgtcaga tcaccgtcaa tgacatgccg   2640
gtgggccgca gcgtggagga ggttctacgc ctgctggagg cttttcagtt cgtggagaag   2700
cacggcgagg tgtgccccgc gaactggaag aagggcgccc ccacgatgaa gccggaaccg   2760
```

aatgcgtctg tcgagggata cttcagcaag cagtaaggat ccactagt 2808

<210> SEQ ID NO 6
<211> LENGTH: 2637
<212> TYPE: DNA
<213> ORGANISM: Artificial Sequence
<220> FEATURE:
<223> OTHER INFORMATION: Description of Artificial Sequence:fusion
protein MTB89F (MTB72F-Erd14)

<400> SEQUENCE: 6
catatgcatc accatcacca tcacacggcc gcgtccgata acttccagct gtcccagggt 60
gggcagggat tcgccattcc gatcgggcag gcgatggcga tcgcgggcca gatccgatcg 120
ggtggggggt cacccaccgt tcatatcggg cctaccgcct tcctcggctt gggtgttgtc 180
gacaacaacg gcaacggcgc acgagtccaa cgcgtggtcg ggagcgctcc ggcggcaagt 240
ctcggcatct ccaccggcga cgtgatcacc gcggtcgacg gcgctccgat caactcggcc 300
accgcgatgg cggacgcgct taacgggcat catcccggtg acgtcatctc ggtgacctgg 360
caaaccaagt cgggcggcac gcgtacaggg aacgtgacat tggccgaggg acccccggcc 420
gaattcatgg tggatttcgg ggcgttacca ccggagatca actccgcgag gatgtacgcc 480
ggcccgggtt cggcctcgct ggtggccgcg gctcagatgt gggacagcgt ggcgagtgac 540
ctgttttcgg ccgcgtcggc gtttcagtcg gtggtctggg gtctgacggt ggggtcgtgg 600
ataggttcgt cggcgggtct gatggtggcg gcggcctcgc cgtatgtggc gtggatgagc 660
gtcaccgcgg ggcaggccga gctgaccgcc gcccaggtcc gggttgctgc ggcggcctac 720
gagacggcgt atgggctgac ggtgcccccg ccggtgatcg ccgagaaccg tgctgaactg 780
atgattctga tagcgaccaa cctcttgggg caaaacaccc cggcgatcgc ggtcaacgag 840
gccgaatacg gcgagatgtg ggcccaagac gccgccgcga tgtttggcta cgccgcggcg 900
acggcgacgg cgacggcgac gttgctgccg ttcgaggagg cgccggagat gaccagcgcg 960
ggtgggctcc tcgagcaggc cgccgcggtc gaggaggcct ccgacaccgc cgcggcgaac 1020
cagttgatga acaatgtgcc ccaggcgctg caacagctgg cccagcccac gcagggcacc 1080
acgccttctt ccaagctggg tggcctgtgg aagacggtct cgccgcatcg gtcgccgatc 1140
agcaacatgg tgtcgatggc caacaaccac atgtcgatga ccaactcggg tgtgtcgatg 1200
accaacacct tgagctcgat gttgaagggc tttgctccgg cggcggccgc ccaggccgtg 1260
caaaccgcgg cgcaaaacgg ggtccgggcg atgagctcgc tgggcagctc gctgggttct 1320
tcgggtctgg gcggtggggt ggccgccaac ttgggtcggg cggcctcggt cggttcgttg 1380
tcggtgccgc aggcctgggc cgcggccaac caggcagtca ccccggcggc gcgggcgctg 1440
ccgctgacca gcctgaccag cgccgcggaa agagggcccg ggcagatgct gggcgggctg 1500
ccggtggggc agatgggcgc cagggccggt ggtgggctca gtggtgtgct gcgtgttccg 1560
ccgcgaccct atgtgatgcc gcattctccg gcagccggcg atatcgcccc gccggccttg 1620
tcgcaggacc ggttcgccga cttccccgcg ctgcccctcg acccgtccgc gatggtcgcc 1680
caagtggggc cacaggtggt caacatcaac accaaactgg gctacaacaa cgccgtgggc 1740
gccgggaccg gcatcgtcat cgatcccaac ggtgtcgtgc tgaccaacaa ccacgtgatc 1800
gcgggcgcca ccgacatcaa tgcgttcagc gtcggctccg gccaaaccta cggcgtcgat 1860
gtggtcgggt atgaccgcac ccaggatgtc gcggtgctgc agctgcgcgg tgccggtggc 1920
ctgccgtcgg cggcgatcgg tggcggcgtc gcggttggtg agcccgtcgt cgcgatgggc 1980

-continued

```
aacagcggtg ggcagggcgg aacgccccgt gcggtgcctg gcagggtggt cgcgctcggc   2040

caaaccgtgc aggcgtcgga ttcgctgacc ggtgccgaag agacattgaa cgggttgatc   2100

cagttcgatg ccgcgatcca gcccggtgat tcgggcgggc ccgtcgtcaa cggcctagga   2160

caggtggtcg gtatgaacac ggccgcgtcc ggtaccatgg ccaccaccct tcccgttcag   2220

cgccacccgc ggtccctctt ccccgagttt tctgagctgt tcgcggcctt cccgtcattc   2280

gccggactcc ggcccacctt cgacacccgg ttgatgcggc tggaagacga gatgaaagag   2340

gggcgctacg aggtacgcgc ggagcttccc ggggtcgacc ccgacaagga cgtcgacatt   2400

atggtccgcg atggtcagct gaccatcaag gccgagcgca ccgagcagaa ggacttcgac   2460

ggtcgctcgg aattcgcgta cggttccttc gttcgcacgg tgtcgctgcc ggtaggtgct   2520

gacgaggacg acattaaggc cacctacgac aagggcattc ttactgtgtc ggtggcggtt   2580

tcggaaggga agccaaccga aaagcacatt cagatccggt ccaccaacta aggatcc      2637
```

```
<210> SEQ ID NO 7
<211> LENGTH: 2487
<212> TYPE: DNA
<213> ORGANISM: Artificial Sequence
<220> FEATURE:
<223> OTHER INFORMATION: Description of Artificial Sequence:fusion
      protein MTB83F (MTB72F-MTI)

<400> SEQUENCE: 7

catatgcatc accatcacca tcacacggcc gcgtccgata acttccagct gtcccagggt     60

gggcagggat tcgccattcc gatcgggcag gcgatggcga tcgcgggcca gatccgatcg    120

ggtggggggt cacccaccgt tcatatcggg cctaccgcct tcctcggctt gggtgttgtc    180

gacaacaacg gcaacggcgc acgagtccaa cgcgtggtcg ggagcgctcc ggcggcaagt    240

ctcggcatct ccaccggcga cgtgatcacc gcggtcgacg gcgctccgat caactcggcc    300

accgcgatgg cggacgcgct taacgggcat catcccggtg acgtcatctc ggtgacctgg    360

caaaccaagt cgggcggcac gcgtacaggg aacgtgacat tggccgaggg acccccggcc    420

gaattcatgg tggatttcgg ggcgttacca ccggagatca actccgcgag gatgtacgcc    480

ggcccgggtt cggcctcgct ggtggccgcg gctcagatgt gggacagcgt ggcgagtgac    540

ctgttttcgg ccgcgtcggc gtttcagtcg gtggtctggg gtctgacggt ggggtcgtgg    600

ataggttcgt cggcgggtct gatggtggcg gcggcctcgc cgtatgtggc gtggatgagc    660

gtcaccgcgg ggcaggccga gctgaccgcc gcccaggtcc gggttgctgc ggcggcctac    720

gagacggcgt atgggctgac ggtgcccccg ccggtgatcg ccgagaaccg tgctgaactg    780

atgattctga tagcgaccaa cctcttgggg caaaacaccc cggcgatcgc ggtcaacgag    840

gccgaatacg gcgagatgtg ggcccaagac gccgccgcga tgtttggcta cgccgcggcg    900

acggcgacgg cgacggcgac gttgctgccg ttcgaggagg cgccggagat gaccagcgcg    960

ggtgggctcc tcgagcaggc cgccgcggtc gaggaggcct ccgacaccgc cgcggcgaac   1020

cagttgatga acaatgtgcc ccaggcgctg caacagctgg cccagcccac gcagggcacc   1080

acgccttctt ccaagctggg tggcctgtgg aagacggtct cgccgcatcg gtcgccgatc   1140

agcaacatgg tgtcgatggc caacaaccac atgtcgatga ccaactcggg tgtgtcgatg   1200

accaacacct tgagctcgat gttgaagggc tttgctccgg cggcggccgc ccaggccgtg   1260

caaaccgcgg cgcaaaacgg ggtccgggcg atgagctcgc tgggcagctc gctgggttct   1320

tcgggtctgg gcggtggggt ggccgccaac ttgggtcggg cggcctcggt cggttcgttg   1380

tcggtgccgc aggcctgggc cgcggccaac caggcagtca ccccggcggc gcgggcgctg   1440
```

ccgctgacca gcctgaccag cgccgcggaa agagggcccg ggcagatgct gggcgggctg 1500
ccggtggggc agatgggcgc cagggccggt ggtgggctca gtggtgtgct gcgtgttccg 1560
ccgcgaccct atgtgatgcc gcattctccg gcagccggcg atatcgcccc gccggccttg 1620
tcgcaggacc ggttcgccga cttccccgcg ctgcccctcg acccgtccgc gatggtcgcc 1680
caagtggggc cacaggtggt caacatcaac accaaactgg gctacaacaa cgccgtgggc 1740
gccgggaccg gcatcgtcat cgatcccaac ggtgtcgtgc tgaccaacaa ccacgtgatc 1800
gcgggcgcca ccgacatcaa tgcgttcagc gtcggctccg gccaaaccta cggcgtcgat 1860
gtggtcgggt atgaccgcac ccaggatgtc gcggtgctgc agctgcgcgg tgccggtggc 1920
ctgccgtcgg cggcgatcgg tggcggcgtc gcggttggtg agcccgtcgt cgcgatgggc 1980
aacagcggtg ggcagggcgg aacgccccgt gcggtgcctg gcagggtggt cgcgctcggc 2040
caaaccgtgc aggcgtcgga ttcgctgacc ggtgccgaag agacattgaa cgggttgatc 2100
cagttcgatg ccgcgatcca gcccggtgat tcgggcgggc ccgtcgtcaa cggcctagga 2160
caggtggtcg gtatgaacac ggccgcgtcc ggtaccatga cgattaatta ccagttcggg 2220
gacgtcgacg ctcatggcgc catgatccgc gctcaggcgg cgtcgcttga ggcggagcat 2280
caggccatcg ttcgtgatgt gttggccgcg ggtgactttt ggggcggcgc cggttcggtg 2340
gcttgccagg agttcattac ccagttgggc cgtaacttcc aggtgatcta cgagcaggcc 2400
aacgcccacg ggcagaaggt gcaggctgcc ggcaacaaca tggcgcaaac cgacagcgcc 2460
gtcggctcca gctgggccta aggatcc 2487

<210> SEQ ID NO 8
<211> LENGTH: 2451
<212> TYPE: DNA
<213> ORGANISM: Artificial Sequence
<220> FEATURE:
<223> OTHER INFORMATION: Description of Artificial Sequence:fusion
protein MTB81F (MTB72F-DPV)

<400> SEQUENCE: 8
catatgcatc accatcacca tcacacggcc gcgtccgata acttccagct gtcccagggt 60
gggcagggat tcgccattcc gatcgggcag gcgatggcga tcgcgggcca gatccgatcg 120
ggtggggggt cacccaccgt tcatatcggg cctaccgcct tcctcggctt gggtgttgtc 180
gacaacaacg gcaacggcgc acgagtccaa cgcgtggtcg ggagcgctcc ggcggcaagt 240
ctcggcatct ccaccggcga cgtgatcacc gcggtcgacg gcgctccgat caactcggcc 300
accgcgatgg cggacgcgct taacgggcat catcccggtg acgtcatctc ggtgacctgg 360
caaaccaagt cgggcggcac gcgtacaggg aacgtgacat tggccgaggg acccccggcc 420
gaattcatgg tggatttcgg ggcgttacca ccggagatca actccgcgag gatgtacgcc 480
ggcccgggtt cggcctcgct ggtggccgcg gctcagatgt gggacagcgt ggcgagtgac 540
ctgttttcgg ccgcgtcggc gtttcagtcg gtggtctggg gtctgacggt ggggtcgtgg 600
ataggttcgt cggcgggtct gatggtggcg gcggcctcgc cgtatgtggc gtggatgagc 660
gtcaccgcgg ggcaggccga gctgaccgcc gcccaggtcc gggttgctgc ggcggcctac 720
gagacggcgt atgggctgac ggtgcccccg ccggtgatcg ccgagaaccg tgctgaactg 780
atgattctga tagcgaccaa cctcttgggg caaaacaccc cggcgatcgc ggtcaacgag 840
gccgaatacg gcgagatgtg ggcccaagac gccgccgcga tgtttggcta cgccgcggcg 900
acggcgacgg cgacggcgac gttgctgccg ttcgaggagg cgccggagat gaccagcgcg 960
ggtgggctcc tcgagcaggc cgccgcggtc gaggaggcct ccgacaccgc cgcggcgaac 1020
cagttgatga acaatgtgcc ccaggcgctg caacagctgg cccagcccac gcagggcacc 1080
acgccttctt ccaagctggg tggcctgtgg aagacggtct cgccgcatcg gtcgccgatc 1140
agcaacatgg tgtcgatggc caacaaccac atgtcgatga ccaactcggg tgtgtcgatg 1200
accaacacct tgagctcgat gttgaagggc tttgctccgg cggcggccgc ccaggccgtg 1260
caaaccgcgg cgcaaaacgg ggtccgggcg atgagctcgc tgggcagctc gctgggttct 1320
tcgggtctgg gcggtggggt ggccgccaac ttgggtcggg cggcctcggt cggttcgttg 1380
tcggtgccgc aggcctgggc cgcggccaac caggcagtca ccccggcggc gcgggcgctg 1440
ccgctgacca gcctgaccag cgccgcggaa agagggcccg ggcagatgct gggcgggctg 1500
ccggtggggc agatgggcgc cagggccggt ggtgggctca gtggtgtgct gcgtgttccg 1560
ccgcgaccct atgtgatgcc gcattctccg gcagccggcg atatcgcccc gccggccttg 1620
tcgcaggacc ggttcgccga cttccccgcg ctgcccctcg acccgtccgc gatggtcgcc 1680
caagtggggc cacaggtggt caacatcaac accaaactgg gctacaacaa cgccgtgggc 1740
gccgggaccg gcatcgtcat cgatcccaac ggtgtcgtgc tgaccaacaa ccacgtgatc 1800
gcgggcgcca ccgacatcaa tgcgttcagc gtcggctccg gccaaaccta cggcgtcgat 1860
gtggtcgggt atgaccgcac ccaggatgtc gcggtgctgc agctgcgcgg tgccggtggc 1920
ctgccgtcgg cggcgatcgg tggcggcgtc gcggttggtg agcccgtcgt cgcgatgggc 1980
aacagcggtg ggcagggcgg aacgccccgt gcggtgcctg gcagggtggt cgcgctcggc 2040
caaaccgtgc aggcgtcgga ttcgctgacc ggtgccgaag agacattgaa cgggttgatc 2100
cagttcgatg ccgcgatcca gcccggtgat tcgggcgggc ccgtcgtcaa cggcctagga 2160
caggtggtcg gtatgaacac ggccgcgtcc ggtaccgatc ccgtggacgc ggtcattaac 2220
accacctgca attacgggca ggtagtagct gcgctcaacg cgacggatcc gggggctgcc 2280
gcacagttca acgcctcacc ggtggcgcag tcctatttgc gcaatttcct cgccgcaccg 2340
ccacctcagc gcgctgccat ggccgcgcaa ttgcaagctg tgccgggggc ggcacagtac 2400
atcggccttg tcgagtcggt tgccggctcc tgcaacaact attaaactag t 2451

<210> SEQ ID NO 9
<211> LENGTH: 3474
<212> TYPE: DNA
<213> ORGANISM: Artificial Sequence
<220> FEATURE:
<223> OTHER INFORMATION: Description of Artificial Sequence:fusion
protein MTB114F (MTB72F-mTCC#2)

<400> SEQUENCE: 9
catatgcatc accatcacca tcacacggcc gcgtccgata acttccagct gtcccagggt 60
gggcagggat tcgccattcc gatcgggcag gcgatggcga tcgcgggcca gatccgatcg 120 ggtgggggt cacccaccgt tcatatcggg cctaccgcct tcctcggctt gggtgttgtc 180
gacaacaacg gcaacggcgc acgagtccaa cgcgtggtcg ggagcgctcc ggcggcaagt 240
ctcggcatct ccaccggcga cgtgatcacc gcggtcgacg gcgctccgat caactcggcc 300
accgcgatgg cggacgcgct taacgggcat catcccggtg acgtcatctc ggtgacctgg 360
caaaccaagt cgggcggcac gcgtacaggg aacgtgacat tggccgaggg acccccggcc 420
gaattcatgg tggatttcgg ggcgttacca ccggagatca actccgcgag gatgtacgcc 480
ggcccgggtt cggcctcgct ggtggccgcg gctcagatgt gggacagcgt ggcgagtgac 540
ctgttttcgg ccgcgtcggc gtttcagtcg gtggtctggg gtctgacggt ggggtcgtgg 600

-continued

```
ataggttcgt cggcgggtct gatggtggcg gcggcctcgc cgtatgtggc gtggatgagc    660
gtcaccgcgg ggcaggccga gctgaccgcc gcccaggtcc gggttgctgc ggcggcctac    720
gagacggcgt atgggctgac ggtgccccccg ccggtgatcg ccgagaaccg tgctgaactg    780
atgattctga tagcgaccaa cctcttgggg caaaacaccc cggcgatcgc ggtcaacgag    840
gccgaatacg gcgagatgtg ggcccaagac gccgccgcga tgtttggcta cgccgcggcg    900
acggcgacgg cgacggcgac gttgctgccg ttcgaggagg cgccggagat gaccagcgcg    960
ggtgggctcc tcgagcaggc cgccgcggtc gaggaggcct ccgacaccgc cgcggcgaac   1020
cagttgatga acaatgtgcc ccaggcgctg caacagctgg cccagcccac gcagggcacc   1080
acgccttctt ccaagctggg tggcctgtgg aagacggtct cgccgcatcg gtcgccgatc   1140
agcaacatgg tgtcgatggc caacaaccac atgtcgatga ccaactcggg tgtgtcgatg   1200
accaacacct tgagctcgat gttgaagggc tttgctccgg cggcggccgc ccaggccgtg   1260
caaaccgcgg cgcaaaacgg ggtccgggcg atgagctcgc tgggcagctc gctgggttct   1320
tcgggtctgg gcggtggggt ggccgccaac ttgggtcggg cggcctcggt cggttcgttg   1380
tcggtgccgc aggcctgggc cgcggccaac caggcagtca ccccggcggc gcgggcgctg   1440
ccgctgacca gcctgaccag cgccgcggaa agagggcccg ggcagatgct gggcgggctg   1500
ccggtggggc agatgggcgc cagggccggt ggtgggctca gtggtgtgct gcgtgttccg   1560
ccgcgaccct atgtgatgcc gcattctccg gcagccggcg atatcgcccc gccggccttg   1620
tcgcaggacc ggttcgccga cttccccgcg ctgcccctcg acccgtccgc gatggtcgcc   1680
caagtggggc cacaggtggt caacatcaac accaaactgg gctacaacaa cgccgtgggc   1740
gccgggaccg gcatcgtcat cgatcccaac ggtgtcgtgc tgaccaacaa ccacgtgatc   1800
gcgggcgcca ccgacatcaa tgcgttcagc gtcggctccg gccaaaccta cggcgtcgat   1860
gtggtcgggt atgaccgcac ccaggatgtc gcggtgctgc agctgcgcgg tgccggtggc   1920
ctgccgtcgg cggcgatcgg tggcggcgtc gcggttggtg agcccgtcgt cgcgatgggc   1980
aacagcggtg ggcagggcgg aacgccccgt gcggtgcctg gcagggtggt cgcgctcggc   2040
caaaccgtgc aggcgtcgga ttcgctgacc ggtgccgaag agacattgaa cgggttgatc   2100
cagttcgatg ccgcgatcca gcccggtgat tcgggcgggc ccgtcgtcaa cggcctagga   2160
caggtggtcg gtatgaacac ggccgcgtcc ggtaccatgg atttcgggct tttacctccg   2220
gaagtgaatt caagccgaat gtattccggt ccggggccgg agtcgatgct agccgccgcg   2280
gccgcctggg acggtgtggc cgcggagttg acttccgccg cggtctcgta tggatcggtg   2340
gtgtcgacgc tgatcgttga gccgtggatg gggccggcgg cggccgcgat ggcggccgcg   2400
gcaacgccgt atgtggggtg gctggccgcc acggcggcgc tggcgaagga gacggccaca   2460
caggcgaggg cagcggcgga agcgtttggg acggcgttcg cgatgacggt gccaccatcc   2520
ctcgtcgcgg ccaaccgcag ccggttgatg tcgctggtcg cggcgaacat tctggggcaa   2580
aacagtgcgg cgatcgcggc tacccaggcc gagtatgccg aaatgtgggc ccaagacgct   2640
gccgtgatgt acagctatga gggggcatct gcggccgcgt cggcgttgcc gccgttcact   2700
ccacccgtgc aaggcaccgg cccggccggg cccgcggccg cagccgcggc gacccaagcc   2760
gccggtgcgg gcgccgttgc ggatgcacag gcgacactgg cccagctgcc cccggggatc   2820
ctgagcgaca ttctgtccgc attggccgcc aacgctgatc cgctgacatc gggactgttg   2880
gggatcgcgt cgaccctcaa cccgcaagtc ggatccgctc agccgatagt gatccccacc   2940
ccgatagggg aattggacgt gatcgcgctc tacattgcat ccatcgcgac cggcagcatt   3000
```

-continued

```
gcgctcgcga tcacgaacac ggccagaccc tggcacatcg gcctatacgg gaacgccggc   3060

gggctgggac cgacgcaggg ccatccactg agttcggcga ccgacgagcc ggagccgcac   3120

tggggcccct tcgggggcgc ggcgccggtg tccgcgggcg tcggccacgc agcattagtc   3180

ggagcgttgt cggtgccgca cagctggacc acggccgccc cggagatcca gctcgccgtt   3240

caggcaacac ccaccttcag ctccagcgcc ggcgccgacc cgacggccct aaacgggatg   3300

ccggcaggcc tgctcagcgg gatggctttg gcgagcctgg ccgcacgcgg cacgacgggc   3360

ggtggcggca cccgtagcgg caccagcact gacggccaag aggacggccg caaacccccg   3420

gtagttgtga ttagagagca gccgccgccc ggaaaccccc cgcggtaaac tagt         3474
```

<210> SEQ ID NO 10
<211> LENGTH: 3104
<212> TYPE: DNA
<213> ORGANISM: Artificial Sequence
<220> FEATURE:
<223> OTHER INFORMATION: Description of Artificial Sequence:fusion
protein MTB102tm2F (MTB102FTM, MTB72F-hTCC#1)

<400> SEQUENCE: 10

```
catatgcatc accatcacca tcacacggcc gcgtccgata acttccagct gtcccagggt     60

gggcagggat tcgccattcc gatcgggcag gcgatggcga tcgcgggcca gatccgatcg    120

ggtgggggt cacccaccgt tcatatcggg cctaccgcct tcctcggctt gggtgttgtc     180

gacaacaacg gcaacggcgc acgagtccaa cgcgtggtcg ggagcgctcc ggcggcaagt    240

ctcggcatct ccaccggcga cgtgatcacc gcggtcgacg gcgctccgat caactcggcc    300

accgcgatgg cggacgcgct taacgggcat catcccggtg acgtcatctc ggtgacctgg    360

caaaccaagt cgggcggcac gcgtacaggg aacgtgacat tggccgaggg acccccggcc    420

gaattcatgg tggatttcgg ggcgttacca ccggagatca actccgcgag gatgtacgcc    480

ggcccgggtt cggcctcgct ggtggccgcg gctcagatgt gggacagcgt ggcgagtgac    540

ctgttttcgg ccgcgtcggc gtttcagtcg gtggtctggg gtctgacggt ggggtcgtgg    600

ataggttcgt cggcgggtct gatggtggcg gcggcctcgc cgtatgtggc gtggatgagc    660

gtcaccgcgg ggcaggccga gctgaccgcc gcccaggtcc gggttgctgc ggcggcctac    720

gagacggcgt atgggctgac ggtgcccccg ccggtgatcg ccgagaaccg tgctgaactg    780

atgattctga tagcgaccaa cctcttgggg caaaacaccc cggcgatcgc ggtcaacgag    840

gccgaatacg gcgagatgtg ggcccaagac gccgccgcga tgtttggcta cgccgcggcg    900

acggcgacgg cgacggcgac gttgctgccg ttcgaggagg cgccggagat gaccagcgcg    960

ggtgggctcc tcgagcaggc cgccgcggtc gaggaggcct ccgacaccgc cgcggcgaac   1020

cagttgatga acaatgtgcc ccaggcgctg caacagctgg cccagcccac gcagggcacc   1080

acgccttctt ccaagctggg tggcctgtgg aagacggtct cgccgcatcg gtcgccgatc   1140

agcaacatgg tgtcgatggc caacaaccac atgtcgatga ccaactcggg tgtgtcgatg   1200

accaacacct tgagctcgat gttgaagggc tttgctccgg cggcggccgc ccaggccgtg   1260

caaaccgcgg cgcaaaacgg ggtccgggcg atgagctcgc tgggcagctc gctgggttct   1320

tcgggtctgg gcggtggggt ggccgccaac ttgggtcggg cggcctcggt cggttcgttg   1380

tcggtgccgc aggcctgggc cgcggccaac caggcagtca ccccggcggc gcgggcgctg   1440

ccgctgacca gcctgaccag cgccgcggaa agagggcccg ggcagatgct gggcgggctg   1500

ccggtggggc agatgggcgc cagggccggt ggtgggctca gtggtgtgct gcgtgttccg   1560
```

-continued ccgcgaccct atgtgatgcc gcattctccg gcagccggcg atatcgcccc gccggccttg 1620
tcgcaggacc ggttcgccga cttccccgcg ctgcccctcg acccgtccgc gatggtcgcc 1680
caagtggggc cacaggtggt caacatcaac accaaactgg gctacaacaa cgccgtgggc 1740
gccgggaccg gcatcgtcat cgatcccaac ggtgtcgtgc tgaccaacaa ccacgtgatc 1800
gcgggcgcca ccgacatcaa tgcgttcagc gtcggctccg gccaaaccta cggcgtcgat 1860
gtggtcgggt atgaccgcac ccaggatgtc gcggtgctgc agctgcgcgg tgccggtggc 1920
ctgccgtcgg cggcgatcgg tggcggcgtc gcggttggtg agcccgtcgt cgcgatgggc 1980
aacagcggtg ggcagggcgg aacgccccgt gcggtgcctg gcagggtggt cgcgctcggc 2040
caaaccgtgc aggcgtcgga ttcgctgacc ggtgccgaag agacattgaa cgggttgatc 2100
cagttcgatg ccgcgatcca gcccggtgat tcgggcgggc ccgtcgtcaa cggcctagga 2160
caggtggtcg gtatgaacac ggccgcgtcc ggtaccatga gcagagcgtt catcatcgat 2220
ccaacgatca gtgccattga cggcttgtac gaccttctgg ggattggaat acccaaccaa 2280
gggggtatcc tttactcctc actagagtac ttcgaaaaag ccctggagga gctggcagca 2340
gcgtttccgg gtgatggctg gttaggttcg gccgcggaca aatacgccgg caaaaaccgc 2400
aaccacgtga attttttcca ggaactggca gacctcgatc gtcagctcat cagcctgatc 2460
cacgaccagg ccaacgcggt ccagacgacc cgcgacaagc ttctcaacgg cctgaaagag 2520
ctttgggaca agctcacggg gtgggtgacc ggactgttct ctcgagggtg gtcgaacctg 2580
gagtccttct ttgcgggcgt ccccggcttg accggcgcga ccagcggctt gtcgcaagtg 2640
actggcttgt tcggtgcggc cggtctgtcc gcatcgtcgg gcttggctca cgcggatagc 2700
ctggcgagct cagccagctt gcccgccctg gccggcattg gggcgggtc cggttttggg 2760 ggcttgccga gcctggctca ggtccatgcc gcctcaactc ggcaggcgct acggccccga 2820
gctgatggcc cggtcggcgc cgctgccgag caggtcggcg ggcagtcgca gctggtctcc 2880
gcgcagggtt cccaaggtat gggcggaccc gtaggcatgg gcggcatgca cccctcttcg 2940
ggggcgtcga aagggacgac gacgaagaag tactcggaag gcgcggcggc gggcactgaa 3000
gacgccgagc gcgcgccagt cgaagctgac gcgggcggtg ggcaaaaggt gctggtacga 3060
aacgtcgtct aaactagtaa cggccgccag tgaagctgga attc 3104

<210> SEQ ID NO 11
<211> LENGTH: 3060
<212> TYPE: DNA
<213> ORGANISM: Artificial Sequence
<220> FEATURE:
<223> OTHER INFORMATION: Description of Artificial Sequence:fusion
protein MTB103F (MTB72F-85b)

<400> SEQUENCE: 11
catatgcatc accatcacca tcacacggcc gcgtccgata acttccagct gtcccagggt 60
gggcagggat tcgccattcc gatcgggcag gcgatggcga tcgcgggcca gatccgatcg 120 ggtgggggt cacccaccgt tcatatcggg cctaccgcct tcctcggctt gggtgttgtc 180
gacaacaacg gcaacggcgc acgagtccaa cgcgtggtcg ggagcgctcc ggcggcaagt 240
ctcggcatct ccaccggcga cgtgatcacc gcggtcgacg gcgctccgat caactcggcc 300
accgcgatgg cggacgcgct taacgggcat catcccggtg acgtcatctc ggtgacctgg 360
caaaccaagt cgggcggcac gcgtacaggg aacgtgacat tggccgaggg acccccggcc 420
gaattcatgg tggatttcgg ggcgttacca ccggagatca actccgcgag gatgtacgcc 480
ggcccgggtt cggcctcgct ggtggccgcg gctcagatgt gggacagcgt ggcgagtgac 540

-continued

```
ctgttttcgg ccgcgtcggc gtttcagtcg gtggtctggg gtctgacggt ggggtcgtgg    600
ataggttcgt cggcgggtct gatggtggcg gcggcctcgc cgtatgtggc gtggatgagc    660
gtcaccgcgg ggcaggccga gctgaccgcc gcccaggtcc gggttgctgc ggcggcctac    720
gagacggcgt atgggctgac ggtgccccg ccggtgatcg ccgagaaccg tgctgaactg    780
atgattctga tagcgaccaa cctcttgggg caaaacaccc cggcgatcgc ggtcaacgag    840
gccgaatacg gcgagatgtg ggcccaagac gccgccgcga tgtttggcta cgccgcggcg    900
acggcgacgg cgacggcgac gttgctgccg ttcgaggagg cgccggagat gaccagcgcg    960
ggtgggctcc tcgagcaggc cgccgcggtc gaggaggcct ccgacaccgc cgcggcgaac   1020
cagttgatga acaatgtgcc ccaggcgctg caacagctgg cccagcccac gcagggcacc   1080
acgccttctt ccaagctggg tggcctgtgg aagacggtct cgccgcatcg gtcgccgatc   1140
agcaacatgg tgtcgatggc caacaaccac atgtcgatga ccaactcggg tgtgtcgatg   1200
accaacacct tgagctcgat gttgaagggc tttgctccgg cggcggccgc ccaggccgtg   1260
caaaccgcgg cgcaaaacgg ggtccgggcg atgagctcgc tgggcagctc gctgggttct   1320
tcgggtctgg gcggtggggt ggccgccaac ttgggtcggg cggcctcggt cggttcgttg   1380
tcggtgccgc aggcctgggc cgcggccaac caggcagtca ccccggcggc gcgggcgctg   1440
ccgctgacca gcctgaccag cgccgcggaa agagggcccg ggcagatgct gggcgggctg   1500
ccggtggggc agatgggcgc cagggccggt ggtgggctca gtggtgtgct gcgtgttccg   1560
ccgcgaccct atgtgatgcc gcattctccg gcagccggcg atatcgcccc gccggccttg   1620
tcgcaggacc ggttcgccga cttccccgcg ctgcccctcg acccgtccgc gatggtcgcc   1680
caagtggggc cacaggtggt caacatcaac accaaactgg gctacaacaa cgccgtgggc   1740
gccgggaccg gcatcgtcat cgatcccaac ggtgtcgtgc tgaccaacaa ccacgtgatc   1800
gcgggcgcca ccgacatcaa tgcgttcagc gtcggctccg gccaaaccta cggcgtcgat   1860
gtggtcgggt atgaccgcac ccaggatgtc gcggtgctgc agctgcgcgg tgccggtggc   1920
ctgccgtcgg cggcgatcgg tggcggcgtc gcggttggtg agcccgtcgt cgcgatgggc   1980
aacagcggtg ggcagggcgg aacgccccgt gcggtgcctg gcagggtggt cgcgctcggc   2040
caaaccgtgc aggcgtcgga ttcgctgacc ggtgccgaag agacattgaa cgggttgatc   2100
cagttcgatg ccgcgatcca gcccggtgat tcgggcgggc ccgtcgtcaa cggcctagga   2160
caggtggtcg gtatgaacac ggccgcgtcc ggtaccttct cccggccggg gctgccggtc   2220
gagtacctgc aggtgccgtc gccgtcgatg ggccgcgaca tcaaggttca gttccagagc   2280
ggtgggaaca actcacctgc ggtttatctg ctcgacggcc tgcgcgccca agacgactac   2340
aacggctggg atatcaacac cccggcgttc gagtggtact accagtcggg actgtcgata   2400
gtcatgccgg tcggcgggca gtccagcttc tacagcgact ggtacagccc ggcctgcggt   2460
aaggctggct gccagactta caagtgggaa accttcctga ccagcgagct gccgcaatgg   2520
ttgtccgcca acagggccgt gaagcccacc ggcagcgctg caatcggctt gtcgatggcc   2580
ggctcgtcgg caatgatctt ggccgcctac catccccagc agttcatcta cgccggctcg   2640
ctgtcggccc tgctggaccc ctctcagggg atggggccta gcctgatcgg cctcgcgatg   2700
ggtgacgccg gcggttacaa ggccgcagac atgtggggtc cctcgagtga cccggcatgg   2760
gagcgcaacg accctacgca gcagatcccc aagctggtcg caaacaacac ccggctatgg   2820
gtttattgcg ggaacggcac cccgaacgag ttgggcggtg ccaacatacc cgccgagttc   2880
ttggagaact tcgttcgtag cagcaacctg aagttccagg atgcgtacaa cgccgcgggc   2940
```

gggcacaacg ccgtgttcaa cttcccgccc aacggcacgc acagctggga gtactggggc 3000
gctcagctca acgccatgaa gggtgacctg cagagttcgt taggcgccgg ctgaggatcc 3060

<210> SEQ ID NO 12
<211> LENGTH: 930
<212> TYPE: PRT
<213> ORGANISM: Artificial Sequence
<220> FEATURE:
<223> OTHER INFORMATION: Description of Artificial Sequence:fusion
protein R95F (MTB72F-MAPS)

<400> SEQUENCE: 12

```
Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Gly Ser Pro Thr Val His Ile
         35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
```

-continued

```
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Ser Cys Gly Asn
                725                 730                 735

Ala Lys Ile Asn Ser Pro Ala Pro Ser Phe Glu Glu Val Ala Leu Met
            740                 745                 750

Pro Asn Gly Ser Phe Lys Lys Ile Ser Leu Ser Ser Tyr Lys Gly Lys
        755                 760                 765
```

Trp Val Val Leu Phe Phe Tyr Pro Leu Asp Phe Thr Phe Val Cys Pro
770 775 780

Thr Glu Val Ile Ala Phe Ser Asp Ser Val Ser Arg Phe Asn Glu Leu
785 790 795 800

Asn Cys Glu Val Leu Ala Cys Ser Ile Asp Ser Glu Tyr Ala His Leu
805 810 815

Gln Trp Thr Leu Gln Asp Arg Lys Lys Gly Gly Leu Gly Thr Met Ala
820 825 830

Ile Pro Met Leu Ala Asp Lys Thr Lys Ser Ile Ala Arg Ser Tyr Gly
835 840 845

Val Leu Glu Glu Ser Gln Gly Val Ala Tyr Arg Gly Leu Phe Ile Ile
850 855 860

Asp Pro His Gly Met Leu Arg Gln Ile Thr Val Asn Asp Met Pro Val
865 870 875 880

Gly Arg Ser Val Glu Glu Val Leu Arg Leu Leu Glu Ala Phe Gln Phe
885 890 895

Val Glu Lys His Gly Glu Val Cys Pro Ala Asn Trp Lys Lys Gly Ala
900 905 910

Pro Thr Met Lys Pro Glu Pro Asn Ala Ser Val Glu Gly Tyr Phe Ser
915 920 925

Lys Gln
930

<210> SEQ ID NO 13
<211> LENGTH: 875
<212> TYPE: PRT
<213> ORGANISM: Artificial Sequence
<220> FEATURE:
<223> OTHER INFORMATION: Description of Artificial Sequence:fusion
protein MTB89F (MTB72F-Erd14)

<400> SEQUENCE: 13

Met His His His His His His Thr Ala Ala Ser Asp Asn Phe Gln Leu
1 5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

Asp Val Ile Ser Val Thr Trp Gln Thr Lys Ser Gly Gly Thr Arg Thr
115 120 125

Gly Asn Val Thr Leu Ala Glu Gly Pro Pro Ala Glu Phe Met Val Asp
130 135 140

Phe Gly Ala Leu Pro Pro Glu Ile Asn Ser Ala Arg Met Tyr Ala Gly
145 150 155 160

Pro Gly Ser Ala Ser Leu Val Ala Ala Ala Gln Met Trp Asp Ser Val
165 170 175

Ala Ser Asp Leu Phe Ser Ala Ala Ser Ala Phe Gln Ser Val Val Trp
180 185 190

-continued

```
Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620
```

Arg Thr Gln Asp Val Ala Val Leu Gln Leu Arg Gly Ala Gly Gly Leu
625 630 635 640

Pro Ser Ala Ala Ile Gly Gly Gly Val Ala Val Gly Glu Pro Val Val
645 650 655

Ala Met Gly Asn Ser Gly Gly Gln Gly Gly Thr Pro Arg Ala Val Pro
660 665 670

Gly Arg Val Val Ala Leu Gly Gln Thr Val Gln Ala Ser Asp Ser Leu
675 680 685

Thr Gly Ala Glu Glu Thr Leu Asn Gly Leu Ile Gln Phe Asp Ala Ala
690 695 700

Ile Gln Pro Gly Asp Ser Gly Gly Pro Val Val Asn Gly Leu Gly Gln
705 710 715 720

Val Val Gly Met Asn Thr Ala Ala Ser Gly Thr Met Ala Thr Thr Leu
725 730 735

Pro Val Gln Arg His Pro Arg Ser Leu Phe Pro Glu Phe Ser Glu Leu
740 745 750

Phe Ala Ala Phe Pro Ser Phe Ala Gly Leu Arg Pro Thr Phe Asp Thr
755 760 765

Arg Leu Met Arg Leu Glu Asp Glu Met Lys Glu Gly Arg Tyr Glu Val
770 775 780

Arg Ala Glu Leu Pro Gly Val Asp Pro Asp Lys Asp Val Asp Ile Met
785 790 795 800

Val Arg Asp Gly Gln Leu Thr Ile Lys Ala Glu Arg Thr Glu Gln Lys
805 810 815

Asp Phe Asp Gly Arg Ser Glu Phe Ala Tyr Gly Ser Phe Val Arg Thr
820 825 830

Val Ser Leu Pro Val Gly Ala Asp Glu Asp Asp Ile Lys Ala Thr Tyr
835 840 845

Asp Lys Gly Ile Leu Thr Val Ser Val Ala Val Ser Glu Gly Lys Pro
850 855 860

Thr Glu Lys His Ile Gln Ile Arg Ser Thr Asn
865 870 875

<210> SEQ ID NO 14
<211> LENGTH: 825
<212> TYPE: PRT
<213> ORGANISM: Artificial Sequence
<220> FEATURE:
<223> OTHER INFORMATION: Description of Artificial Sequence:fusion
protein MTB83F (MTB72F-MTI)

<400> SEQUENCE: 14

Met His His His His His His Thr Ala Ala Ser Asp Asn Phe Gln Leu
1 5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

-continued

```
Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
```

```
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Thr Ile Asn Tyr
                725                 730                 735

Gln Phe Gly Asp Val Asp Ala His Gly Ala Met Ile Arg Ala Gln Ala
            740                 745                 750

Ala Ser Leu Glu Ala Glu His Gln Ala Ile Val Arg Asp Val Leu Ala
        755                 760                 765

Ala Gly Asp Phe Trp Gly Gly Ala Gly Ser Val Ala Cys Gln Glu Phe
    770                 775                 780

Ile Thr Gln Leu Gly Arg Asn Phe Gln Val Ile Tyr Glu Gln Ala Asn
785                 790                 795                 800

Ala His Gly Gln Lys Val Gln Ala Ala Gly Asn Asn Met Ala Gln Thr
                805                 810                 815

Asp Ser Ala Val Gly Ser Ser Trp Ala
            820                 825


<210> SEQ ID NO 15
<211> LENGTH: 813
<212> TYPE: PRT
<213> ORGANISM: Artificial Sequence
<220> FEATURE:
<223> OTHER INFORMATION: Description of Artificial Sequence:fusion
      protein MTB81F (MTB72F-DPV)

<400> SEQUENCE: 15

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
```

-continued

```
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495
```

```
Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Asp Pro Val Asp Ala
                725                 730                 735

Val Ile Asn Thr Thr Cys Asn Tyr Gly Gln Val Val Ala Ala Leu Asn
            740                 745                 750

Ala Thr Asp Pro Gly Ala Ala Ala Gln Phe Asn Ala Ser Pro Val Ala
        755                 760                 765

Gln Ser Tyr Leu Arg Asn Phe Leu Ala Ala Pro Pro Pro Gln Arg Ala
    770                 775                 780

Ala Met Ala Ala Gln Leu Gln Ala Val Pro Gly Ala Ala Gln Tyr Ile
785                 790                 795                 800

Gly Leu Val Glu Ser Val Ala Gly Ser Cys Asn Asn Tyr
                805                 810


<210> SEQ ID NO 16
<211> LENGTH: 1154
<212> TYPE: PRT
<213> ORGANISM: Artificial Sequence
<220> FEATURE:
<223> OTHER INFORMATION: Description of Artificial Sequence:fusion
      protein MTB114F (MTB72F-mTCC#2)

<400> SEQUENCE: 16

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Gly Ser Pro Thr Val His Ile
         35                  40                  45
```

-continued

```
Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480
```

-continued

```
Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Asp Phe Gly Leu
                725                 730                 735

Leu Pro Pro Glu Val Asn Ser Ser Arg Met Tyr Ser Gly Pro Gly Pro
            740                 745                 750

Glu Ser Met Leu Ala Ala Ala Ala Ala Trp Asp Gly Val Ala Ala Glu
        755                 760                 765

Leu Thr Ser Ala Ala Val Ser Tyr Gly Ser Val Val Ser Thr Leu Ile
    770                 775                 780

Val Glu Pro Trp Met Gly Pro Ala Ala Ala Ala Met Ala Ala Ala Ala
785                 790                 795                 800

Thr Pro Tyr Val Gly Trp Leu Ala Ala Thr Ala Ala Leu Ala Lys Glu
                805                 810                 815

Thr Ala Thr Gln Ala Arg Ala Ala Ala Glu Ala Phe Gly Thr Ala Phe
            820                 825                 830

Ala Met Thr Val Pro Pro Ser Leu Val Ala Ala Asn Arg Ser Arg Leu
        835                 840                 845

Met Ser Leu Val Ala Ala Asn Ile Leu Gly Gln Asn Ser Ala Ala Ile
    850                 855                 860

Ala Ala Thr Gln Ala Glu Tyr Ala Glu Met Trp Ala Gln Asp Ala Ala
865                 870                 875                 880

Val Met Tyr Ser Tyr Glu Gly Ala Ser Ala Ala Ala Ser Ala Leu Pro
                885                 890                 895

Pro Phe Thr Pro Pro Val Gln Gly Thr Gly Pro Ala Gly Pro Ala Ala
```

900 905 910

Ala Ala Ala Ala Thr Gln Ala Ala Gly Ala Gly Ala Val Ala Asp Ala
915 920 925

Gln Ala Thr Leu Ala Gln Leu Pro Pro Gly Ile Leu Ser Asp Ile Leu
930 935 940

Ser Ala Leu Ala Ala Asn Ala Asp Pro Leu Thr Ser Gly Leu Leu Gly
945 950 955 960

Ile Ala Ser Thr Leu Asn Pro Gln Val Gly Ser Ala Gln Pro Ile Val
965 970 975

Ile Pro Thr Pro Ile Gly Glu Leu Asp Val Ile Ala Leu Tyr Ile Ala
980 985 990

Ser Ile Ala Thr Gly Ser Ile Ala Leu Ala Ile Thr Asn Thr Ala Arg
995 1000 1005

Pro Trp His Ile Gly Leu Tyr Gly Asn Ala Gly Gly Leu Gly Pro Thr
1010 1015 1020

Gln Gly His Pro Leu Ser Ser Ala Thr Asp Glu Pro Glu Pro His Trp
1025 1030 1035 1040

Gly Pro Phe Gly Gly Ala Ala Pro Val Ser Ala Gly Val Gly His Ala
1045 1050 1055

Ala Leu Val Gly Ala Leu Ser Val Pro His Ser Trp Thr Thr Ala Ala
1060 1065 1070

Pro Glu Ile Gln Leu Ala Val Gln Ala Thr Pro Thr Phe Ser Ser Ser
1075 1080 1085

Ala Gly Ala Asp Pro Thr Ala Leu Asn Gly Met Pro Ala Gly Leu Leu
1090 1095 1100

Ser Gly Met Ala Leu Ala Ser Leu Ala Ala Arg Gly Thr Thr Gly Gly
1105 1110 1115 1120

Gly Gly Thr Arg Ser Gly Thr Ser Thr Asp Gly Gln Glu Asp Gly Arg
1125 1130 1135

Lys Pro Pro Val Val Val Ile Arg Glu Gln Pro Pro Pro Gly Asn Pro
1140 1145 1150

Pro Arg

<210> SEQ ID NO 17
<211> LENGTH: 1022
<212> TYPE: PRT
<213> ORGANISM: Artificial Sequence
<220> FEATURE:
<223> OTHER INFORMATION: Description of Artificial Sequence:fusion protein MTB102tm2F (MTB102FTM2, MTB72F-hTCC#1)

<400> SEQUENCE: 17

Met His His His His His His Thr Ala Ala Ser Asp Asn Phe Gln Leu
1 5 10 15

Ser Gln Gly Gly Gln Gly Phe Ala Ile Pro Ile Gly Gln Ala Met Ala
20 25 30

Ile Ala Gly Gln Ile Arg Ser Gly Gly Gly Ser Pro Thr Val His Ile
35 40 45

Gly Pro Thr Ala Phe Leu Gly Leu Gly Val Val Asp Asn Asn Gly Asn
50 55 60

Gly Ala Arg Val Gln Arg Val Val Gly Ser Ala Pro Ala Ala Ser Leu
65 70 75 80

Gly Ile Ser Thr Gly Asp Val Ile Thr Ala Val Asp Gly Ala Pro Ile
85 90 95

Asn Ser Ala Thr Ala Met Ala Asp Ala Leu Asn Gly His His Pro Gly
100 105 110

-continued

```
Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
```

-continued

```
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Met Ser Arg Ala Phe
                725                 730                 735

Ile Ile Asp Pro Thr Ile Ser Ala Ile Asp Gly Leu Tyr Asp Leu Leu
            740                 745                 750

Gly Ile Gly Ile Pro Asn Gln Gly Gly Ile Leu Tyr Ser Ser Leu Glu
        755                 760                 765

Tyr Phe Glu Lys Ala Leu Glu Glu Leu Ala Ala Ala Phe Pro Gly Asp
    770                 775                 780

Gly Trp Leu Gly Ser Ala Ala Asp Lys Tyr Ala Gly Lys Asn Arg Asn
785                 790                 795                 800

His Val Asn Phe Phe Gln Glu Leu Ala Asp Leu Asp Arg Gln Leu Ile
                805                 810                 815

Ser Leu Ile His Asp Gln Ala Asn Ala Val Gln Thr Thr Arg Asp Lys
            820                 825                 830

Leu Leu Asn Gly Leu Lys Glu Leu Trp Asp Lys Leu Thr Gly Trp Val
        835                 840                 845

Thr Gly Leu Phe Ser Arg Gly Trp Ser Asn Leu Glu Ser Phe Phe Ala
    850                 855                 860

Gly Val Pro Gly Leu Thr Gly Ala Thr Ser Gly Leu Ser Gln Val Thr
865                 870                 875                 880

Gly Leu Phe Gly Ala Ala Gly Leu Ser Ala Ser Ser Gly Leu Ala His
                885                 890                 895

Ala Asp Ser Leu Ala Ser Ser Ala Ser Leu Pro Ala Leu Ala Gly Ile
            900                 905                 910

Gly Gly Gly Ser Gly Phe Gly Gly Leu Pro Ser Leu Ala Gln Val His
        915                 920                 925

Ala Ala Ser Thr Arg Gln Ala Leu Arg Pro Arg Ala Asp Gly Pro Val
    930                 935                 940

Gly Ala Ala Ala Glu Gln Val Gly Gly Gln Ser Gln Leu Val Ser Ala
945                 950                 955                 960
```

-continued

```
Gln Gly Ser Gln Gly Met Gly Gly Pro Val Gly Met Gly Gly Met His
                965                 970                 975

Pro Ser Ser Gly Ala Ser Lys Gly Thr Thr Thr Lys Lys Tyr Ser Glu
            980                 985                 990

Gly Ala Ala Ala Gly Thr Glu Asp Ala Glu Arg Ala Pro Val Glu Ala
        995                1000                1005

Asp Ala Gly Gly Gly Gln Lys Val Leu Val Arg Asn Val Val
   1010                1015                1020


<210> SEQ ID NO 18
<211> LENGTH: 1016
<212> TYPE: PRT
<213> ORGANISM: Artificial Sequence
<220> FEATURE:
<223> OTHER INFORMATION: Description of Artificial Sequence:fusion
      protein MTB103F (MTB72F-85b)

<400> SEQUENCE: 18

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Gly Ser Pro Thr Val His Ile
         35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300
```

```
Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser Gly Thr Phe Ser Arg Pro Gly
                725                 730                 735
```

```
Leu Pro Val Glu Tyr Leu Gln Val Pro Ser Pro Ser Met Gly Arg Asp
            740                 745                 750

Ile Lys Val Gln Phe Gln Ser Gly Gly Asn Asn Ser Pro Ala Val Tyr
        755                 760                 765

Leu Leu Asp Gly Leu Arg Ala Gln Asp Asp Tyr Asn Gly Trp Asp Ile
    770                 775                 780

Asn Thr Pro Ala Phe Glu Trp Tyr Tyr Gln Ser Gly Leu Ser Ile Val
785                 790                 795                 800

Met Pro Val Gly Gly Gln Ser Ser Phe Tyr Ser Asp Trp Tyr Ser Pro
                805                 810                 815

Ala Cys Gly Lys Ala Gly Cys Gln Thr Tyr Lys Trp Glu Thr Phe Leu
            820                 825                 830

Thr Ser Glu Leu Pro Gln Trp Leu Ser Ala Asn Arg Ala Val Lys Pro
        835                 840                 845

Thr Gly Ser Ala Ala Ile Gly Leu Ser Met Ala Gly Ser Ser Ala Met
    850                 855                 860

Ile Leu Ala Ala Tyr His Pro Gln Gln Phe Ile Tyr Ala Gly Ser Leu
865                 870                 875                 880

Ser Ala Leu Leu Asp Pro Ser Gln Gly Met Gly Pro Ser Leu Ile Gly
                885                 890                 895

Leu Ala Met Gly Asp Ala Gly Gly Tyr Lys Ala Ala Asp Met Trp Gly
            900                 905                 910

Pro Ser Ser Asp Pro Ala Trp Glu Arg Asn Asp Pro Thr Gln Gln Ile
        915                 920                 925

Pro Lys Leu Val Ala Asn Asn Thr Arg Leu Trp Val Tyr Cys Gly Asn
    930                 935                 940

Gly Thr Pro Asn Glu Leu Gly Gly Ala Asn Ile Pro Ala Glu Phe Leu
945                 950                 955                 960

Glu Asn Phe Val Arg Ser Ser Asn Leu Lys Phe Gln Asp Ala Tyr Asn
                965                 970                 975

Ala Ala Gly Gly His Asn Ala Val Phe Asn Phe Pro Pro Asn Gly Thr
            980                 985                 990

His Ser Trp Glu Tyr Trp Gly Ala Gln Leu Asn Ala Met Lys Gly Asp
        995                 1000                1005

Leu Gln Ser Ser Leu Gly Ala Gly
   1010                1015


<210> SEQ ID NO 19
<211> LENGTH: 330
<212> TYPE: PRT
<213> ORGANISM: Artificial Sequence
<220> FEATURE:
<223> OTHER INFORMATION: Description of Artificial Sequence:wild-type
      mature MTB32A (Ra35)

<400> SEQUENCE: 19

Met His His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
             20                  25                  30

Gln Val Gly Pro Gln Val Val Asn Ile Asn Thr Lys Leu Gly Tyr Asn
         35                  40                  45

Asn Ala Val Gly Ala Gly Thr Gly Ile Val Ile Asp Pro Asn Gly Val
     50                  55                  60

Val Leu Thr Asn Asn His Val Ile Ala Gly Ala Thr Asp Ile Asn Ala
 65                  70                  75                  80
```

```
Phe Ser Val Gly Ser Gly Gln Thr Tyr Gly Val Asp Val Val Gly Tyr
                 85                  90                  95

Asp Arg Thr Gln Asp Val Ala Val Leu Gln Leu Arg Gly Ala Gly Gly
            100                 105                 110

Leu Pro Ser Ala Ala Ile Gly Gly Gly Val Ala Val Gly Glu Pro Val
        115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ser Gly Gly Pro Val Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255

Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285

Ser Ala Thr Ala Met Ala Asp Ala Leu Asn Gly His His Pro Gly Asp
    290                 295                 300

Val Ile Ser Val Thr Trp Gln Thr Lys Ser Gly Gly Thr Arg Thr Gly
305                 310                 315                 320

Asn Val Thr Leu Ala Glu Gly Pro Pro Ala
                325                 330


<210> SEQ ID NO 20
<211> LENGTH: 330
<212> TYPE: PRT
<213> ORGANISM: Artificial Sequence
<220> FEATURE:
<223> OTHER INFORMATION: Description of Artificial Sequence:mutated
      MTB32AMutSA (Ra35 mutSA)

<400> SEQUENCE: 20

Met His His His His His His Ala Pro Pro Ala Leu Ser Gln Asp Arg
  1               5                  10                  15

Phe Ala Asp Phe Pro Ala Leu Pro Leu Asp Pro Ser Ala Met Val Ala
             20                  25                  30

Gln Val Gly Pro Gln Val Val Asn Ile Asn Thr Lys Leu Gly Tyr Asn
         35                  40                  45

Asn Ala Val Gly Ala Gly Thr Gly Ile Val Ile Asp Pro Asn Gly Val
     50                  55                  60

Val Leu Thr Asn Asn His Val Ile Ala Gly Ala Thr Asp Ile Asn Ala
 65                  70                  75                  80

Phe Ser Val Gly Ser Gly Gln Thr Tyr Gly Val Asp Val Val Gly Tyr
                 85                  90                  95

Asp Arg Thr Gln Asp Val Ala Val Leu Gln Leu Arg Gly Ala Gly Gly
            100                 105                 110
```

```
Leu Pro Ser Ala Ala Ile Gly Gly Gly Val Ala Val Gly Glu Pro Val
        115                 120                 125

Val Ala Met Gly Asn Ser Gly Gly Gln Gly Gly Thr Pro Arg Ala Val
    130                 135                 140

Pro Gly Arg Val Val Ala Leu Gly Gln Thr Val Gln Ala Ser Asp Ser
145                 150                 155                 160

Leu Thr Gly Ala Glu Glu Thr Leu Asn Gly Leu Ile Gln Phe Asp Ala
                165                 170                 175

Ala Ile Gln Pro Gly Asp Ala Gly Gly Pro Val Val Asn Gly Leu Gly
            180                 185                 190

Gln Val Val Gly Met Asn Thr Ala Ala Ser Asp Asn Phe Gln Leu Ser
        195                 200                 205

Gln Gly Gly Gln Gly Phe Ala Ile Pro Ile Gly Gln Ala Met Ala Ile
    210                 215                 220

Ala Gly Gln Ile Arg Ser Gly Gly Gly Ser Pro Thr Val His Ile Gly
225                 230                 235                 240

Pro Thr Ala Phe Leu Gly Leu Gly Val Val Asp Asn Asn Gly Asn Gly
                245                 250                 255

Ala Arg Val Gln Arg Val Val Gly Ser Ala Pro Ala Ala Ser Leu Gly
            260                 265                 270

Ile Ser Thr Gly Asp Val Ile Thr Ala Val Asp Gly Ala Pro Ile Asn
        275                 280                 285

Ser Ala Thr Ala Met Ala Asp Ala Leu Asn Gly His His Pro Gly Asp
    290                 295                 300

Val Ile Ser Val Thr Trp Gln Thr Lys Ser Gly Gly Thr Arg Thr Gly
305                 310                 315                 320

Asn Val Thr Leu Ala Glu Gly Pro Pro Ala
                325                 330


<210> SEQ ID NO 21
<211> LENGTH: 729
<212> TYPE: PRT
<213> ORGANISM: Artificial Sequence
<220> FEATURE:
<223> OTHER INFORMATION: Description of Artificial Sequence:MTB72F

<400> SEQUENCE: 21

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Arg Ser Gly Gly Gly Ser Pro Thr Val His Ile
         35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140
```

-continued

```
Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205

Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575
```

```
Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725


<210> SEQ ID NO 22
<211> LENGTH: 729
<212> TYPE: PRT
<213> ORGANISM: Artificial Sequence
<220> FEATURE:
<223> OTHER INFORMATION: Description of Artificial Sequence:mutated
      MTB72FMutSA (Mtb72f-mutSA)

<400> SEQUENCE: 22

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Gly Ser Pro Thr Val His Ile
        35                  40                  45

Gly Pro Thr Ala Phe Leu Gly Leu Gly Val Val Asp Asn Asn Gly Asn
     50                  55                  60

Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Ala Gln Met Trp Asp Ser Val
                165                 170                 175

Ala Ser Asp Leu Phe Ser Ala Ala Ser Ala Phe Gln Ser Val Val Trp
            180                 185                 190

Gly Leu Thr Val Gly Ser Trp Ile Gly Ser Ser Ala Gly Leu Met Val
        195                 200                 205
```

```
Ala Ala Ala Ser Pro Tyr Val Ala Trp Met Ser Val Thr Ala Gly Gln
    210                 215                 220

Ala Glu Leu Thr Ala Ala Gln Val Arg Val Ala Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
            260                 265                 270

Pro Ala Ile Ala Val Asn Glu Ala Glu Tyr Gly Glu Met Trp Ala Gln
        275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Ala Val Glu Glu Ala Ser Asp Thr Ala
                325                 330                 335

Ala Ala Asn Gln Leu Met Asn Asn Val Pro Gln Ala Leu Gln Gln Leu
            340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala Ala
                405                 410                 415

Gln Ala Val Gln Thr Ala Ala Gln Asn Gly Val Arg Ala Met Ser Ser
            420                 425                 430

Leu Gly Ser Ser Leu Gly Ser Ser Gly Leu Gly Gly Gly Val Ala Ala
        435                 440                 445

Asn Leu Gly Arg Ala Ala Ser Val Gly Ser Leu Ser Val Pro Gln Ala
    450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
                485                 490                 495

Gly Gly Leu Pro Val Gly Gln Met Gly Ala Arg Ala Gly Gly Gly Leu
            500                 505                 510

Ser Gly Val Leu Arg Val Pro Pro Arg Pro Tyr Val Met Pro His Ser
        515                 520                 525

Pro Ala Ala Gly Asp Ile Ala Pro Pro Ala Leu Ser Gln Asp Arg Phe
    530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
                565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
```

-continued

```
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
        675                 680                 685

Thr Gly Ala Glu Glu Thr Leu Asn Gly Leu Ile Gln Phe Asp Ala Ala
    690                 695                 700

Ile Gln Pro Gly Asp Ala Gly Gly Pro Val Val Asn Gly Leu Gly Gln
705                 710                 715                 720

Val Val Gly Met Asn Thr Ala Ala Ser
                725
```